(12) United States Patent
Owa et al.

(10) Patent No.: US 8,772,269 B2
(45) Date of Patent: Jul. 8, 2014

(54) USE OF SULFONAMIDE-INCLUDING COMPOUNDS IN COMBINATION WITH ANGIOGENESIS INHIBITORS

(75) Inventors: Takashi Owa, Tsukuba (JP); Yoichi Ozawa, Tsukuba (JP); Taro Semba, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 997 days.

(21) Appl. No.: 11/226,655

(22) Filed: Sep. 13, 2005

(65) Prior Publication Data

US 2006/0135486 A1    Jun. 22, 2006

Related U.S. Application Data

(60) Provisional application No. 60/609,452, filed on Sep. 13, 2004.

(30) Foreign Application Priority Data

Feb. 28, 2005   (JP) ................................... 2005-54150
Feb. 28, 2005   (JP) ................................... 2005-54475

(51) Int. Cl.
   *A61K 31/655*   (2006.01)
   *A61K 31/47*    (2006.01)

(52) U.S. Cl.
   USPC .......................................... 514/151; 514/357

(58) Field of Classification Search
   None
   See application file for complete search history.

(56) References Cited

U.S. PATENT DOCUMENTS

| | | | |
|---|---|---|---|
| 4,960,908 A | 10/1990 | Ito et al. | |
| 5,409,949 A | 4/1995 | Buzzetti et al. | |
| 5,436,235 A | 7/1995 | Buzzetti et al. | |
| 5,594,028 A | 1/1997 | Harper et al. | |
| 5,747,651 A | 5/1998 | Lemischka | |
| 5,792,783 A | 8/1998 | Tang et al. | |
| 6,054,297 A | 4/2000 | Carter et al. | |
| 6,217,866 B1 | 4/2001 | Schlessinger et al. | |
| 6,469,043 B1* | 10/2002 | Haneda et al. ................. | 514/414 |
| 6,524,583 B1 | 2/2003 | Thorpe et al. | |
| 6,524,832 B1 | 2/2003 | Kufe et al. | |
| 6,676,941 B2 | 1/2004 | Thorpe et al. | |
| 6,762,180 B1 | 7/2004 | Roth et al. | |
| 6,811,779 B2 | 11/2004 | Rockwell et al. | |
| 7,070,968 B2 | 7/2006 | Kufe et al. | |
| 2002/0032313 A1 | 3/2002 | Ferrara et al. | |
| 2004/0009965 A1 | 1/2004 | Collins et al. | |
| 2004/0053908 A1* | 3/2004 | Funahashi et al. ............. | 514/183 |
| 2005/0119303 A1 | 6/2005 | Wakabayashi et al. | |
| 2006/0251734 A1 | 11/2006 | Kufe et al. | |
| 2007/0078159 A1 | 4/2007 | Matsushima | |

FOREIGN PATENT DOCUMENTS

| | | |
|---|---|---|
| EP | 0222475 A1 | 5/1987 |
| EP | 0673937 A1 | 9/1995 |
| EP | 0520722 | 12/1996 |
| EP | 1074542 A1 | 2/2001 |
| EP | 1415987 A1 | 5/2004 |
| EP | 1481678 A1 | 12/2004 |
| EP | 1522540 A1 | 4/2005 |
| JP | 62-96459 A | 5/1987 |
| JP | H05-306277 A | 11/1993 |
| JP | 7-165708 A | 8/1994 |
| WO | 0555036 A2 | 8/1993 |
| WO | 95/07276 A1 | 3/1995 |
| WO | 98/35958 A1 | 8/1998 |
| WO | 99/62890 A1 | 12/1999 |
| WO | 00/47212 A1 | 8/2000 |
| WO | 00/50395 A1 | 8/2000 |
| WO | 01/23375 A2 | 4/2001 |
| WO | 01/27081 A1 | 4/2001 |
| WO | 02/32872 A1 | 4/2002 |
| WO | 02/098848 A1 | 12/2002 |
| WO | 03/006462 A1 | 1/2003 |
| WO | 03/035629 A1 | 5/2003 |
| WO | WO 03/074045 A1 | 9/2003 |
| WO | 2004/020434 A1 | 3/2004 |
| WO | WO 2005/063713 A1 | 7/2005 |

OTHER PUBLICATIONS

European Search Report for corresponding European Patent Application No. 05785820.
Fossella F V et al., Hypoprothrombinemia from Coadministration of Sulofenur (LY 186641) and Warfarin: Report of Three Cases—Investigation New Drugs 1991 US, vol. 9, No. 4, 1991, pp. 357-359.
Mousa Shaker A., Anticoagulants in Thrombosis and Cancer: The Missing Link—Seminars in Thrombosis and Hemostasis, vol. 28, No. 1, Feb. 2002.
Ono Naoto et al., Angiogenesis Inhibitor, E7820; Enhancement of Anti-Angiogenic Activity Through the Combination With Receptor Kinase Inhibitors of VEGF or bFGF—Proceeding of the Annual Meeting of the American Association for Cancer Research, vol. 43, Mar. 1, 2002, p. 182
Uckun et al., Ionizing radiation stimulates unidentified tyrosine-specific protein kinases in human B-lymphocyte precursors, triggering apoptosis and clonogenic cell death, Proceedings of the National Academy of Sciences, vol. 89, pp. 9005-9009, Oct. 1992.
Uckun et al., Tyrosine phosophorylation is a mandatory proximal step in radiation-induced activation of he protein kinase C signaling pathway in human B-lymphocyte precursors, Proceedings of the National Academy of Sciences, vol. 90, pp. 252-256, Jan. 1993.
Hofmann et al., Enhancement of the Antiproliferative Effect of cis-Diamminedichloroplatinum(II) and Nitrogen Mustard by Inhibitors of Protein Kinase C, Int. J. Cancer, vol. 42, pp. 382-388, 1988.
Aboud-Pirak et al., Efficacy of Antibodies to Epidermal Growth Factor Receptor Against KB Carcinoma In Vitro and in Nude Mice, Journal of the National Cancer Institute, vol. 80:20, pp. 1605-1611, Dec. 1988.

(Continued)

Primary Examiner — Frederick Krass
Assistant Examiner — Celeste A Roney
(74) Attorney, Agent, or Firm — Birch, Stewart, Kolasch & Birch, LLP

(57) ABSTRACT

The present invention relates to pharmaceutical compositions comprising a sulfonamide-including compound in combination with an angiogenesis inhibitor.

6 Claims, 10 Drawing Sheets

(56) References Cited

OTHER PUBLICATIONS

Extended European Search Report dated Aug. 17, 2011, for Application No. 11169343.8.
Marmé, "The impact of anti-angiogenic agents on cancer therapy", J. Cancer Res. Clin. Oncol., vol. 129, XP-002656444, 2003, pp. 607-620.
Asano, Makoto et al., "Inhibition of Tumor Growth and Metastasis by an Immunoneutralizing Monoclonal Antibody . . . " Cancer Research, vol. 55, pp. 5296-5301, Nov. 15, 1995.
Bankston, Donald et al., "A Scaleable Synthesis of BAY 43/9006: A Potent Raf Kinase . . . ", Organic Process Res. & Dev., vol. 6, pp. 777-781, 2002.
Beebe, Jean S. et al., "Pharmacological Characterization of CP-547,632, a Novel Vascular Endothelial . . . " Cancer Research, vol. 63, pp. 7301-7309, Nov. 1, 2003.
Bergers, Gabriele et al., "Benefits of Targeting Both Pericytes and Endothelial Cells in the Tumor . . . " J. Clinical Investigation, vol. 111, No. 9, pp. 1287-1295, May 2003.
Bold, Guido et al., "New Anilinophthalazines as Potent and Orally Well . . . " J. Med. Chem., vol. 43, pp. 2310-2323, 2000.
Bramhall, Simon R., "The Matrix Metalloproteinases and Their Inhibitors in Pancreatic Cancer" International J. Of Pancreatology, vol. 21, No. 1, pp. 1-12, Feb. 1997.
Brueggen, J. et al., "Preclinical Profile of ABP309, a Potent 2nd Generation . . . ", Poster Session-Angiogenesis and Metastasis Inhibitors, pp. 54-55, 2004.
Certified Experiment Results for Japanese Application No. 2006-535245 dated Mar. 2, 2012 with English Translation.
Cheung, Mui et al., "Discovery of Indazolylpyrimidines as Potent Inhibitors . . . ", Proceedings of the American Association for Cancer Research, vol. 44, p. 9, Mar. 2003.
Chou, Ting-Chao, and Paul Talalay, "Quantitative Analysis of Dose-Effect Relationships: The Combined Effects of Multiple Drugs or Enzyme Inhibitors," Adv. Enzyme Regul., vol. 22, pp. 27-55, 1984.
Dias, Sergio et al., "IL-12 Regulates VEGF and MMPs in a Murine Breast Cancer Model" Int. J. Cancer, vol. 78, pp. 361-365, 1998.
Emanuel, Stuart et al., "A Vascular Endothelial Growth Factor Receptor-2 Kinase . . . ", Molecular Pharmacology, vol. 66, No. 3, pp. 635-647, 2004.
English translation of IPRP of PCT/JP2005/017228 issued on Mar. 20, 2007.
English translation of IPRP of PCT/JP2005/017238 issued on Mar. 20, 2007.
Fargnoli, Joseph et al., "Preclinical Studies of BMS-582664 . . . ", Proceedings of the American Association for Cancer Research, vol. 46, p. 713, Apr. 2005.
Fong, T. A. T. et al., "SU5416 Is a Potent and Selective Inhibitor of the Vascular Endothelial Growth Factor Receptor . . . " Cancer Research, vol. 59, pp. 99-106, Jan. 1, 1999.
Gingrich, Diane E. et al., "A New Class of Potent Vascular Endothelial Growth Factor Receptor Tyrosine Kinase Inhibitors: Structure—Activity . . . " J. Med. Chem. vol. 46, pp. 5375-5388, 2003.
Guo, Xiao-Ning et al., "In Vitro Pharmacological Characterization of TKI-28 . . . " Cancer Biology & Therapy, vol. 4., No. 10, pp. 1125-1132, Oct. 2005.
Gutheil, John C. et al., "Targeted Antiangiogenic Therapy for Cancer Using Vitaxin: Aw Humanized Monoclonal Antibody . . . " Clinical Cancer Research, vol. 6, pp. 3056-3061, Aug. 2000.
Hamby, James M. et al., "Structure—Activity Relationships for a Novel Series of Pyrido . . . ", J. Med. Chem., vol. 40, pp. 2296-2303, 1997.
Harlow, E. And D. Lane, "Antibodies: A Laboratory Manual", Cold Spring Harbor Laboratory, pp. 55-243, Cold Spring Harbor, NY, 1988.
Hennequin, Laurent F. et al., "Design and Structure—Activity Relationship of a New Class of Potent VEGF Receptor . . . " J. Med. Chem., vol. 42, pp. 5369-5389, 1999.
Hennequin, Laurent F. et al., "Novel 4-Anilinoquinazolines With C-7 Basic Side Chains: Design and Structure . . . " J. Med. Chem., vol. 45, pp. 1300-1312, 2002.
Herbst, R., "AMG 706 First in Human, Open-label, Dose-finding . . . ", Poster Session—Angiogenesis and Metastasis Inhibitors, p. 48, 2004.
Hori, Akira et al., "Suppression of Solid Tumor Growth by Immunoneutralizing Monoclonal Antibody Against Human Basic . . . " Cancer Research, vol. 51, pp. 6180-6184, Nov. 15, 1991.
Hu-Lowe, Diana D. et al., "SU014813 is a Novel Multireceptor Tyrosine Kinase . . . ", Proceedings of the American Association for Cancer Research, vol. 46, p. 475, Apr. 2005.
Inai, Tetsuichiro et al., "Inhibition of Vascular Endothelial Growth Factor (VEGF) Signaling . . . " American J. Of Pathology, vol. 165, No. 1, pp. 35-52, Jul. 2004.
International Search Report of PCT/JP2005/017228 issued on Nov. 8, 2005 with English translation.
International Search Report of PCT/JP2005/017238 issued on Nov. 1, 2005 with English translation.
Irizarry, Rafael a. et al., "Exploration, Normalization, and Summaries of High Density Oligonucleotide . . . ", Biostatistics, vol. 4, No. 2, pp. 249-264, 2003.
Japanese Decision of Rejection for Application No. 2006-535245 dated Apr. 24, 2012 with English translation.
Japanese Decision to Dismiss the Amendment for Application No. 2006-535245 dated Apr. 24, 2012 with English translation.
Japanese Extension of Time to Office Action for Application No. 2006-535245 dated Dec. 22, 2011 with English translation.
Japanese Office Action for Application No. 2006-535245 dated Feb. 15, 2011 with English translation.
Japanese Office Action for Application No. 2006-535245 dated Nov. 1, 2011 with English translation.
Japanese Written Amendment for Application No. 2006-535245 dated Sep. 4, 2012 with English translation.
Japanese Written Amendment to Decision of Rejection for Application No. 2006-535245 dated Jul. 24, 2012 with English translation.
Japanese Written Amendment to Office Action for Application No. 2006-535245 dated Apr. 13, 2011 with English translation.
Japanese Written Amendment to Office Action for Application No. 2006-535245 dated Dec. 22, 2011 with English translation.
Japanese Written Appeal to Decision of Rejection for Application No. 2006-535245 dated Jul. 24, 2012 with English translation.
Japanese Written Opinion to Office Action for Application No. 2006-535245 dated Apr. 13, 2011 with English translation.
Japanese Written Opinion to Office Action for Application No. 2006-535245 dated Dec. 22, 2011 with English translation.
Joly, A., "In Vitro and In Vivo Characterization of Exel-7647, a Novel . . . ", Poster Session—Angiogenesis and Metastasis Inhibitors, p. 43, 2004.
Kubo, Kazuo et al., "Novel Potent Orally Active Selective VEGFR-2 Tyrosine Kinase . . . ", J. Med. Chem., vol. 48, pp. 1359-1366, 2005.
Kudoh, Kazuya et al., "Monitoring the Expression Profiles of Doxorubicin-induced and Doxorubicin-resistant Cancer Cells by cDNA Microarray," Cancer Research, vol. 60, pp. 4161-4166, Aug. 1, 2000.
Kumar, Rakesh et al., "Discovery and Biological Evaluation of GW654652 . . . ", Proceedings of the American Association for Cancer Research, vol. 44, p. 9, Mar. 2003.
Laird, Douglas A. et al., "SU6668 Is a Potent Antiangiogenic and Antitumor Agent That Induces Regression of Established Tumors", Cancer Research, vol. 60, pp. 4152-4160, Aug. 1, 2000.
Lee, Sang Hoon et al., "In Vivo Target Modulation and Biological Activity of Chir-258 . . . ", Clin. Cancer Res., vol. 11, pp. 3633-3641, May 15, 2005.
Li, Junling et al., "ABT-869 a Novel Multi-targeted Receptor . . . ", Proceedings of the American Association for Cancer Research, vol. 46, p. 1407, Apr. 2005.
Liu, Shenping et al., "Structure of Human Methionine Aminopeptidase-2 Complexed with Fumagillin" Science, vol. 282, pp. 1324-1327, Nov. 13, 1998.
Lockhart, David J., et al., "Expression Monitoring by Hybridization to High-Density Oligonucleotide Arrays" Nature Biotechnology, vol. 14, pp. 1675-1680, Dec. 1996.

(56) References Cited

OTHER PUBLICATIONS

Masferrer, Jaime L. et al., "COX-2 Inhibitors: A New Class of Antiangiogenic Agents" Annals of N.Y. Acad. of Sciences, pp. 84-86, 1999.
Mendel, Dirk B. et at "In vivo Antitumor Activity of SU11248, a Novel Tyrosine Kinase Inhibitor . . . " Clinical Cancer Research, vol. 9, pp. 327-337, Jan. 2003.
Mohammadi, Moosa et al., "Crystal Structure of an Angiogenesis Inhibitor . . . ", The EMBO Journal, vol. 17, No. 20, pp. 5896-5904, 1998.
Monks, A. et al., "Feasibility of a High-Flux Anticancer Drug Screen Using a Diverse Panel . . . ", J. of the Natl. Cancer Inst., vol. 83, No. 11, pp. 757-766, Jun. 5, 1991.
Mosmann, Tim, "Rapid Colorimetric Assay for Cellular Growth and Survival: Application to Proliferation and Cytotoxicity Assays", Elsevier, Journal of Immunological Methods, vol. 65, pp. 55-63, 1983. 1.
Mousa, Shaker A., "Anticoagulants in Thrombosis and Cancer: The Missing Link," Seminars in Thrombosis and Hemostasis, vol. 28, No. 1, pp. 45-52, 2002.
Nakamura, Kazuhide et al., "In Vitro Selectivity and Potency of KRN951 . . . ," Proceedings of the American Association for Cancer Research, vol. 45, p. 594, Mar. 2004.
Nakamura, Kazuhide et al., "KRN633: A Selective Inhibitor of Vascular Endothelial Growth Factor Receptor-2 Tyrosine Kinase . . . " Molecular Cancer Therapeutics, vol. 3, No. 12, pp. 1639-1649, Dec. 2004.
Paull, K. D. et al., "Display and Analysis of Patterns of Differential Activity of Drugs . . . ", J. of the Natl. Cancer Inst., pp. 1088-1092, 1989.
Petti, Filippo et al., "Temporal Quantitation of Mutant Kit Tyrosine . . . " Molecular Cancer Therapeutics, vol. 4, No. 8, pp. 1186-1197, 2005.
Podar, Klaus et al., "GW654652, the Pan-inhibitor of VEGF Receptors . . . ", Blood Journal, vol. 103, pp. 3474-3479, 2004.
Proceedings of the American Assoc. for Cancer Research, vol. 42, p. 583, 2001.
Proceedings of the American Association for Cancer Research, vol. 43, p. 1080, Mar. 2002.
Proceedings of the American Association for Cancer Research, vol. 43, p. 175, Mar. 2002.
Response to European Search Report for Application No. 11169343.8 dated Mar. 14, 2012.
Rhee, Chang H. et al., "Characterization of Cellular Pathways Involved in Glioblastoma Response to the Chemotherapeutic Agent . . . " Oncology Reports, vol. 6, pp. 393-401, 1999.
Ross, Douglas T. et al., "Systematic Variation in Gene Expression Patterns in Human Cancer Cell Lines" Nature Genetics, vol. 24, pp. 227-235, 2000.
Ruggeri, Bruce et al., "CEP-7055: A Novel, Orally Active Pan Inhibitor of Vascular Endothelial Growth . . . ", Cancer Research, vol. 63, pp. 5978-5991, Sep. 15, 2003.
Schena, Mark et al., "Quantitative Monitoring of Gene Expression Patterns with a Complementary DNA Microarray" Science, vol. 270, pp. 467-470, Oct. 20, 1995.
Scherf, Uwe et al., "A Gene Expression Database for the Molecular Pharmacology of Cancer" Nature Genetics, vol. 24, pp. 236-244, Mar. 2000.
Siemeister, Gerhard et al., "ZK-304709, the Oral Multitarget Tumor Growth . . . ", Proceedings of the American Association for Cancer Research, vol. 46, pp. 1374-1375, Apr. 2005.
Sun, Li et al., "Design, Synthesis, and Evaluations of Substituted 3-{(3- or 4-Carboxyethylpyrrol-2-yl)methylideny} . . . " J. Med. Chem., vol. 42, pp. 5120-5130, 1999.
Sun, Li et al., "Discovery of 5-[5-Fluoro-2-oxo-1,2-dihydroindol-(3Z)-ylidenemethy1]-2,4-dimethyl-1H-pyrrole-3-carboxylic Acid . . . " J. Med. Chem, vol. 46, pp. 1116-1119, 2003.
Sun, Li et al., "Synthesis and Biological Evaluations of 3-Substituted Indolin-2-ones: A Novel Class of Tyrosine . . . " J. Med. Chem., vol. 41, pp. 2588-2603, 1998.
Suttle, A. B. et al., "Pharmacokinetics (PK) and Tolerability of GVV786034 . . . ", American Soc. of Clin. Oncology, 2004.
Taguchi, Eri et al., "A Novel Orally Active Inhibitor of VEGF Receptor . . . " Proceedings of the American Association for Cancer Research, vol. 45, p. 595, Mar. 2004.
Tajima et al., "Antibody Treatment of Breast Cancer," Biotherapy, vol. 17(5), pp. 437-446, 2003.
Traxler, Peter et al., "AEE788: A Dual Family Epidermal Growth Factor Receptor/ErbB2 . . . ", Cancer Research, vol. 64, pp. 4931-4941, Jul. 15, 2004.
Ueda, Yasuji et al., "VGA1155, a Novel Binding Antagonist of VEGF . . . ", Anticancer Research, vol. 24, pp. 3009-3018, 2004.
Wedge, Stephen R. et al., "AZD2171: A Highly Potent, Orally Bioavailable, Vascular . . . " Cancer Research, vol. 65, No. 10, pp. 4389-4400, May 15, 2005.
Wedge, Stephen R. et al., "ZD4190: An Orally Active Inhibitor of Vascular Endothelial Growth Factor . . . " Cancer Research, vol. 60., pp. 970-975, Feb. 15, 2000.
Weisberg, E. et al., "Inhibition of Mutant FLT3 Receptors in Leukemia Cells by a Small Molecule Tyrosine Kinase Inhibitor" Proceedings of Am. Soc. Clin. Oncology, vol. 21, p. 41, 2002.
Wilhelm, Scott M. et al., "Bay 43/9006 Exhibits Broad Spectrum Oral Antitumor Activity . . . ", Cancer Research, vol. 64, pp. 7099-7109, Oct. 1, 2004.
Willett, Christopher G. et al., "Direct Evidence that the VEGF-specific antibody bevacizumab has antivascular effects in human rectal cancer" Nature Medicine vol. 10, No. 2, pp. 145-147, Feb. 2004.
Wolf, F. J. et al., "Substituted Sulfaquinoxalines. III Extension of the Glyoxalate Synthesis of 2-Aminoquinoxaline" J. Am. Chem. Soc., vol. 71, pp. 6-10, 1947.
Wood, Jeanette M. et al., "PTK787/ZK 222584, a Novel and Potent Inhibitor of Vascular Endothelial Growth . . . " Cancer Research, vol. 60, 2178-2189, Apr. 15, 2000.
Wu, Yan et al., "A Fully Human Monoclonal Antibody Against VEGFR-1 . . .", Proceedings of the American Association for Cancer Research, vol. 45, pp. 694-695, Mar. 2004.
Yigitbasi, Orhan G. et al., "Tumor Cell and Endothelial Cell Therapy of Oral Cancer . . . ", Cancer Research, vol. 64, pp. 7977-7984, Nov. 1, 2004.
Yokoi, Akira et al., "Profiling Novel Sulfonamide Antitumor Agents with Cell-based Phenotypic Screens and Array-based Gene Expression Analysis", Molecular Cancer Therapeutics, vol. 1, pp. 275-286, Feb. 2002.
Zhang, Haifan et al., "Inhibition of Both Autocrine and Paracine Growth . . . ", Proceedings of the American Association for Cancer Research, vol. 44, p. 1479, Mar. 2003.
Zimmermann, Johann et al., "Protease Inhibitor Induced Gene Expression Profiles Reveal Overexpression . . . " Oncogene, vol. 19, pp. 2913-2920, 2000.
Office Action for European Application No. 11169343.8, dated Jun. 10, 2013.
Reply to Examination Report with Amendment for European Application No. 11169343.8, dated Sep. 26, 2013.

\* cited by examiner

USE OF SULFONAMIDE-INCLUDING COMPOUNDS IN COMBINATION WITH ANGIOGENESIS INHIBITORS

INCORPORATION BY REFERENCE

The present application claims priority under 35 U.S.C. §119 to Japanese Patent Application Nos. 2005-054150 filed Feb. 28, 2005 and 2005-054475 filed Feb. 28, 2005. The contents of the applications are incorporated herein by reference in their entireties.

FIELD OF THE INVENTION

The present invention relates to novel pharmaceutical compositions and kits, which are characterized by comprising a sulfonamide-including compound in combination with an angiogenesis inhibitor, more specifically with a VEGF inhibitor or a FGF inhibitor.

BACKGROUND OF THE INVENTION

Cancer chemotherapeutics conventionally used include alkylating agents such as cyclophosphamide, antimetabolites such as methotrexate and fluorouracil, antibiotics such as adriamycin, mitomycin and bleomycin, plant-derived agents such as taxol, vincristine and etoposide, as well as metal complexes such as cisplatin. However, none of these substances can be regarded as having a sufficient anti-tumor effect; there has been a strong demand for the development of new anti-tumor agents.

In recent years, sulfonamide-including compounds have been reported as useful anti-tumor agents[1-4]. Among them, N-(3-chloro-1H-indol-7-yl)-4-sulfamoylbenzenesulfonamide (hereinafter also referred to as E7070), N-(3-cyano-4-methyl-1H-indol-7-yl)-3-cyanobenzenesulfonamide (hereinafter also referred to as E7820), N-[[(4-chlorophenyl)-amino]carbonyl]-2,3-dihydro-1H-indene-5-sulfonamide (hereinafter also referred to as LY186641), N-[[(3,4-dichlorophenyl)amino]carbonyl]-2,3-dihydrobenzofuran-5-sulfonamide (hereinafter also referred to as LY295501), N-(2,4-dichlorobenzoyl)-4-chlorophenyl-sulfonamide (hereinafter also referred to as LY-ASAP), N-(2,4-dichlorobenzoyl)-5-bromothiophene-2-sulfonamide (hereinafter also referred to as LY573636), 2-sulfanylamido-5-chloroquinoxaline (hereinafter also referred to as CQS) and the like are found to be active against various types of tumors and hence very useful.

Likewise, the anti-VEGF antibody bevacizumab has been reported as an antibody inhibiting angiogenesis[5].

Previous studies have reported that the combined use of a sulfonamide-including compound and an angiogenesis inhibitor produces excellent angiogenesis inhibitory activity and anti-tumor activity[6]. However, there has been no report on whether a combination of a sulfonamide-including compound and bevacizumab produces any effect; various documents say nothing about this combination[6].

In recent years, methods have been established for simultaneously detecting the expression levels of many genes using various DNA microarrays, and DNA microarrays are applied to a wide range of purposes[7-8]. Likewise, several reports have been made on studies in which DNA microarrays (In part, there is macroarray which uses membrane filters) are used to detect changes in gene expression caused when tumor cells are treated with anti-cancer agents[9-11]. These reports indicate that the analysis of gene expression changes is very useful in comprehensively studying, at the molecular level, property comparison of a plurality of cell populations and biological changes in cells caused by treatment with drugs, etc.

In addition, there are other reports in which 60 types of cancer cell line panels from the US National Cancer Institute are reclassified and examined for their properties based on the analysis of their gene expression profiles[12] and in which these 60 types of cancer cell line panels are further studied for the relationship between their gene expression profiles and the susceptibility of each cell line to various anti-cancer agents[13].

REFERENCES (1) JP 7-165708 A
(2) International Publication No. WO00/50395
(3) European Patent Publication No. 0222475
(4) International Publication No. WO02/098848
(5) Direct evidence that the VEGF-specific antibody bevacizumab has antivascular effects in human rectal cancer. Nat Med. 2004 February; 10 (2):145-7.
(6) International Publication No. WO03/074045
(7) Schena M, Shalon D, Davis R W, Brown P O. Science, 1995, 270, 467-70.
(8) Lockhart, D. J., Dong, H., Byrne, M. C., Follettie, M. T., Gallo, M. V., Chee, M. S., Mittmann, M., Wang C., Kobayashi, M., Horton, H. Brown, E. L., Nature Biotechnology, 1996, 14, 1675-1680.
(9) Rhee C H, Ruan S, Chen S, Chenchik A, Levin V A, Yung A W, Fuller G N, Zhang W. Oncol Rep, 1999, 6, 393-401.
(10) Zimmermann J, Erdmann D, Lalande I, Grossenbacher R, Noorani M, Furst P, Oncogene, 2000, 19, 2913-20.
(11) Kudoh K, Ramanna M, Ravatn R, Elkahloun A G, Bittner M L, Meltzer P S, Trent J M, Dalton W S, Chin K V, Cancer Res, 2000, 4161-6.
(12) Ross D T, Scherf U, Eisen M B, Perou C M, Rees C, Spellman P, Iyer V, Jeffrey S S, Van de Rijn M, Waltham M, Pergamenschikov A, Lee J C, Lashkari D, Shalon D, Myers T G, Weinstein J N, Botstein D, Brown P O, Nat Genet, 2000, 24, 227-35.
(13) Scherf U, Ross D T, Waltham M, Smith L H, Lee J K, Tanabe L, Kohn K W, Reinhold W C, Myers T G, Andrews D T, Scudiero D A, Eisen M B, Sausville E A, Pommier Y. Botstein D, Brown P O, Weinstein J N, Nat Genet, 2000, 24, 236-44.

SUMMARY OF THE INVENTION

The present invention was made under such circumstances, and the problem to be solved by the invention is to find out pharmaceutical compositions and kits having excellent angiogenesis inhibitory activity and/or anti-tumor activity.

As a result of extensive and intensive efforts made to solve the problem stated above, the inventors of the present invention have found that there is a high correlation between the pattern of gene expression changes and cell growth inhibitory activity provided by E7820, E7070, LY186641, LY295501, LY573636 or CQS or combinations thereof in experiments using DNA microarrays and cancer cell line panels. Likewise, in cell growth inhibition assays, the inventors have also found that cancer cell lines resistant to E7070 have cross resistance to E7820, LY186641, LY295501, LY-ASAP, LY573636 and CQS. Based on these results, the inventors of the present invention have obtained a finding that E7070, E7820, LY186641, LY295501, LY-ASAP, LY573636 or CQS or combinations thereof have the same or similar mechanism of action and produce the same or similar genetic changes and effects.

On the other hand, E7820 has been reported to show excellent angiogenesis inhibitory activity and anti-tumor activity when used in combination with an angiogenesis inhibitor (WO03/074045). Thus, based on the above finding, E7070, LY186641, LY295501, LY-ASAP, LY573636 or CQS or combinations thereof are also believed to show excellent angiogenesis inhibitory activity and anti-tumor activity when used in combination with an angiogenesis inhibitor; sulfonamide-including compounds, preferably E7070, LY186641, LY295501, LY-ASAP, LY573636 or CQS or combinations thereof, have now been found to provide useful pharmaceutical compositions and kits when combined with angiogenesis inhibitors.

Moreover, in a vascular endothelial cell proliferation assay (in vitro), E7820 was found to show a statistically (combination index) significant synergistic antiproliferative effect when used in combination with bevacizumab. Likewise, in a subcutaneous transplantation model (in vivo) of a colon cancer cell line, E7820 was found to show a statistically (two-way analysis of variance) significant synergistic anti-tumor effect when used in combination with bevacizumab. Further, the combined use of E7820 and bevacizumab was observed to produce an excellent anti-tumor effect that could not be achieved by bevacizumab alone. This combined use of E7820 and bevacizumab produced a significantly strong synergistic effect when compared to the combined use of E7820 and anti-VEGF antibody found in International Publication No. WO03/074045, and such a strong synergistic effect was completely unexpected. In view of the above findings, E7070, E7820, LY186641, LY295501, LY-ASAP, LY573636 or CQS or combinations thereof are believed to show excellent anti-tumor activity and angiogenesis inhibitory activity when used in combination with bevacizumab; sulfonamide-including compounds, preferably E7070, E7820, LY186641, LY295501, LY-ASAP, LY573636 or CQS or combinations thereof, have now been found to provide useful pharmaceutical compositions and kits when combined with bevacizumab.

Namely, the present invention is directed to the following.

(1) A pharmaceutical composition comprising a sulfonamide-including compound in combination with an angiogenesis inhibitor.

(2) A kit comprising:
(a) at least one selected from the group consisting of a packaging container, an instruction manual and an package insert, each of which describes the combined use of a sulfonamide-including compound and an angiogenesis inhibitor; and
(b) a pharmaceutical composition comprising the sulfonamide-including compound.

(3) A kit comprising a set of a formulation comprising a sulfonamide-including compound and a formulation comprising an angiogenesis inhibitor.

(4) A method for preventing or treating cancer and/or a method for inhibiting angiogenesis, which comprises administering a sulfonamide-including compound and an angiogenesis inhibitor to a patient.

The above sulfonamide-including compound includes at least one compound selected from the group consisting of:

a compound of Formula (I):

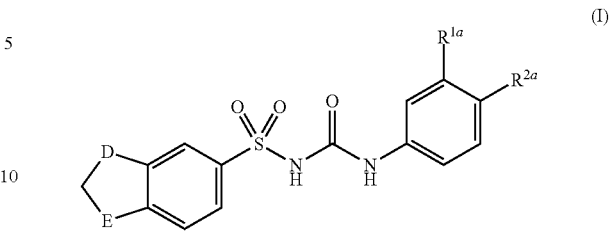

[wherein E represents —O—, —N(CH$_3$)—, —CH$_2$—, —CH$_2$CH$_2$— or —CH$_2$O—, D represents —CH$_2$— or —O—, R$^{1a}$ represents a hydrogen atom or a halogen atom, and R$^{2a}$ represents a halogen atom or a trifluoromethyl group], a compound of Formula (II):

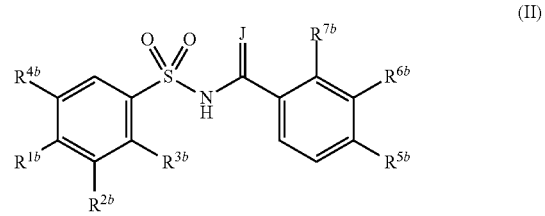

[wherein J represents —O— or —NH—, R$^{1b}$ represents a hydrogen atom, a halogen atom, an optionally substituted C$_{1-6}$ alkyl group, an optionally substituted C$_{1-4}$ alkoxy group, an optionally substituted C$_{1-4}$ alkylthio group, an optionally substituted C$_{2-5}$ alkoxycarbonyl group, a nitro group, an azido group, —O(SO$_2$)CH$_3$, —N(CH$_3$)$_2$, a hydroxyl group, a phenyl group, a substituted phenyl group, a pyridinyl group, a thienyl group, a furyl group, a quinolinyl group or a triazole group, R$^{2b}$ represents a hydrogen atom, a halogen atom, a cyano group, an optionally substituted C$_{1-6}$ alkyl group, an optionally substituted C$_{2-5}$ alkoxycarbonyl group, an optionally substituted C$_{1-4}$ alkoxy group, an optionally substituted phenyl group or an optionally substituted quinolinyl group, R$^{3b}$ represents a hydrogen atom or an optionally substituted C$_{1-4}$ alkoxy group, R$^{4b}$ represents a hydrogen atom or an optionally substituted C$_{1-6}$ alkyl group (provided that at least one of R$^{3b}$ and R$^{4b}$ is a hydrogen atom), R$^{5b}$ represents a hydrogen atom, a halogen atom, an optionally substituted C$_{1-4}$ alkyl group or a nitro group, R$^{6b}$ represents a hydrogen atom, a halogen atom or an optionally substituted C$_{1-6}$ alkyl group (provided that when R$^{6b}$ is an optionally substituted C$_{1-6}$ alkyl group, R$^{5b}$ is a hydrogen atom and R$^{7b}$ is a halogen atom), and R$^{7b}$ represents a halogen atom or an optionally substituted C$_{1-6}$ alkyl group (provided that when either R$^{5b}$ or R$^{7b}$ is an optionally substituted C$_{1-6}$ alkyl group or when R$^{7b}$ is a halogen atom or an optionally substituted C$_{1-6}$ alkyl group, either R$^{5b}$ or R$^{6b}$ is a hydrogen atom)], a compound of Formula (III):

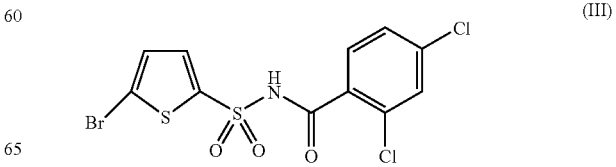

and
a compound of Formula (IV):

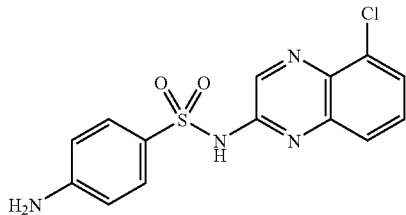

or a pharmacologically acceptable salt thereof or a solvate thereof.

Alternatively, the above sulfonamide-including compound may be a compound of Formula (IX):

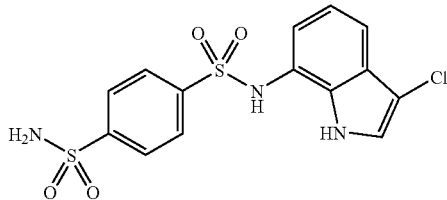

or a pharmacologically acceptable salt thereof or a solvate thereof.

The present invention is also directed to the following.
(5) A pharmaceutical composition comprising a sulfonamide-including compound in combination with a VEGF receptor kinase inhibitor.
(6) A kit comprising:
(a) at least one selected from the group consisting of a packaging container, an instruction manual and an package insert, each of which describes the combined use of a sulfonamide-including compound and a VEGF receptor kinase inhibitor; and
(b) a pharmaceutical composition comprising the sulfonamide-including compound.
(7) A kit comprising a set of a formulation comprising a sulfonamide-including compound and a formulation comprising a VEGF receptor kinase inhibitor.
(8) A method for preventing or treating cancer and/or a method for inhibiting angiogenesis, which comprises administering a sulfonamide-including compound and a VEGF receptor kinase inhibitor to a patient.

The above sulfonamide-including compound includes a compound of Formula (XIV):

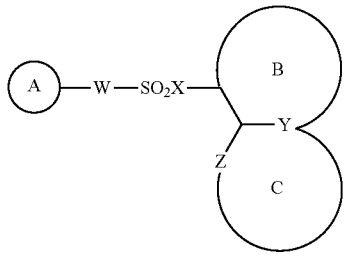

[wherein
the ring A represents an optionally substituted monocyclic or bicyclic aromatic ring,
the ring B represents an optionally substituted 6-membered cyclic unsaturated hydrocarbon or an optionally substituted unsaturated 6-membered heterocyclic ring containing one nitrogen atom as a heteroatom,
the ring C represents an optionally substituted 5-membered heterocyclic ring containing one or two nitrogen atoms,
W represents a single bond or —CH=CH—,
X represents —N($R^1$)— or an oxygen atom,
Y represents:

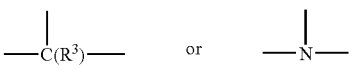

and
Z represents —N($R^2$)—,
wherein $R^1$, $R^2$ and $R^3$, which may be the same or different, each independently represent a hydrogen atom or a lower alkyl group]
or a pharmacologically acceptable salt thereof or a solvate thereof.

The above VEGF receptor kinase inhibitor may include at least one compound selected from the group consisting of:
(10) N-{2-chloro-4-[(6,7-dimethoxy-4-quinolyl)oxy]phenyl}-N'-(5-methyl-3-isoxazolyl)urea,
(11) 4-[(4-fluoro-2-methylindol-5-yl)oxy]-6-methoxy-7-[3-(pyrrolidin-1-yl)propoxy]quinazoline,
(12) 6-[2-(methylcarbamoyl)phenylsulfanyl]-3-E-[2-(pyridin-2-yl)ethenyl]indazole,
(13) 5-((Z)-(5-fluoro-2-oxo-1,2-dihydro-3H-indol-3-ylidene)methyl)-N-((2S)-2-hydroxy-3-morpholin-4-yl-propyl)-2,4-dimethyl-1H-pyrrole-3-carboxamide,
(14) 3-((quinolin-4-ylmethyl)amino)-N-(4-(trifluoromethoxy)phenyl)thiophene-2-carboxamide,
(15) 6-(2,6-dichlorophenyl)-8-methyl-2-phenylamino-8H-pyrido[2,3-d]pyrimidin-7-one,
(16) 2-((1,6-dihydro-6-oxo-pyridin-3-ylmethyl)amino)-N-(3-(trifluoromethyl)phenyl)-3-pyridine-carboxamide,
(17) 4-(4-(4-chloro-phenylamino)-furo[2,3-d]pyridazin-7-yloxymethyl)-pyridine-2-carboxylic acid methylamide,
(18) N-(3-trifluoromethyl-4-chlorophenyl)-N'-(4-(2-methylcarbamoylpyridin-4-yl)oxyphenyl)urea,
(19) 4-amino-5-fluoro-3-(6-(4-methyl-piperazin-1-yl)-1H-benzimidazol-2-yl)-1H-quinolin-2-one,
(20) 4-(4-(1-amino-1-methyl-ethyl)-phenyl)-2-(4-(2-morpholin-4-yl-ethyl)-phenylamino)-pyrimidine-5-carbonitrile,
(21) [6-[4-[(4-ethylpiperazin-1-yl)methyl]phenyl]-7H-pyrrolo[2,3-d]pyrimidin-4-yl]-((R)-1-phenylethyl)amine,
(22) 9-(1-methylethoxy)methyl-12-(3-hydroxypropyl)-6H,7H,13H-indeno[2,1-a]pyrrolo[3,4-c]carbazol-5-one,
(23) N-(2,4-difluorophenyl)-N'-{4-[(6,7-dimethoxy-4-quinolyl)-oxy]-2-fluorophenyl}urea,
(24) 5-[N-methyl-N-(4-octadecyloxyphenyl)acetyl]amino-2-methylthiobenzoic acid,
(25) N-[4-(3-amino-1H-indazol-4-yl)phenyl]-N'-(2-fluoro-5-methylphenyl)urea,
(26) 2-methyl-6-[2-(1-methyl-1H-imidazol-2-yl)-thieno[3,2-b]pyridin-7-yloxy]-benzo[b]thiophene-3-carboxylic acid methylamide,
(27) (R)-1-(4-(4-fluoro-2-methyl-1H-indol-5-yloxy)-5-methylpyrrolo[1,2-f][1,2,4]triazin-6-yloxy)propan-2-ol, and

(28) (S)—((R)-1-(4-(4-fluoro-2-methyl-1H-indol-5-yloxy)-5-methylpyrrolo[1,2-f][1,2,4]triazin-6-yloxy)propan-2-ol) 2-aminopropanonate or a pharmacologically acceptable salt thereof or a solvate thereof.

Alternatively, the above VEGF receptor kinase inhibitor may be 4-(3-chloro-4-(cyclopropylaminocarbonyl)aminophenoxy)-7-methoxy-6-quinolinecarboxamide, or a pharmacologically acceptable salt thereof or a solvate thereof.

The present invention provides pharmaceutical compositions and kits showing excellent angiogenesis inhibitory activity and/or anti-tumor activity.

More specifically, as a result of combining sulfonamide-including compounds, preferably E7070, LY186641, LY295501, LY-ASAP, LY573636 or CQS or combinations thereof, with angiogenesis inhibitors, the present invention provides pharmaceutical compositions and kits showing excellent angiogenesis inhibitory activity and/or anti-tumor activity and enables them to be used for cancer treatment or angiogenesis inhibition. Likewise, when combining sulfonamide-including compounds, preferably E7820, with VEGF receptor kinase inhibitors, the present invention provides pharmaceutical compositions and kits showing excellent angiogenesis inhibitory activity and/or anti-tumor activity and enables them to be used for cancer treatment or angiogenesis inhibition.

BRIEF DESCRIPTION OF THE DRAWINGS

FIG. 2 shows correlation coefficients in DNA microarrays in Example 2.

FIG. 4 shows correlation coefficients in DNA microarrays in Example 2.

In FIG. 8, "*" denotes a statistically significant synergistic effect at a significance level of less than 0.01. In FIG. 8, "#" denotes the number of days counted from the first day (Day 1) of administration.

In FIG. 10, Compound A denotes 4-(3-chloro-4-(cyclopropylaminocarbonyl)aminophenoxy)-7-methoxy-6-quinolinecarboxamide.

DETAILED DESCRIPTION OF THE INVENTION

Figure 1:
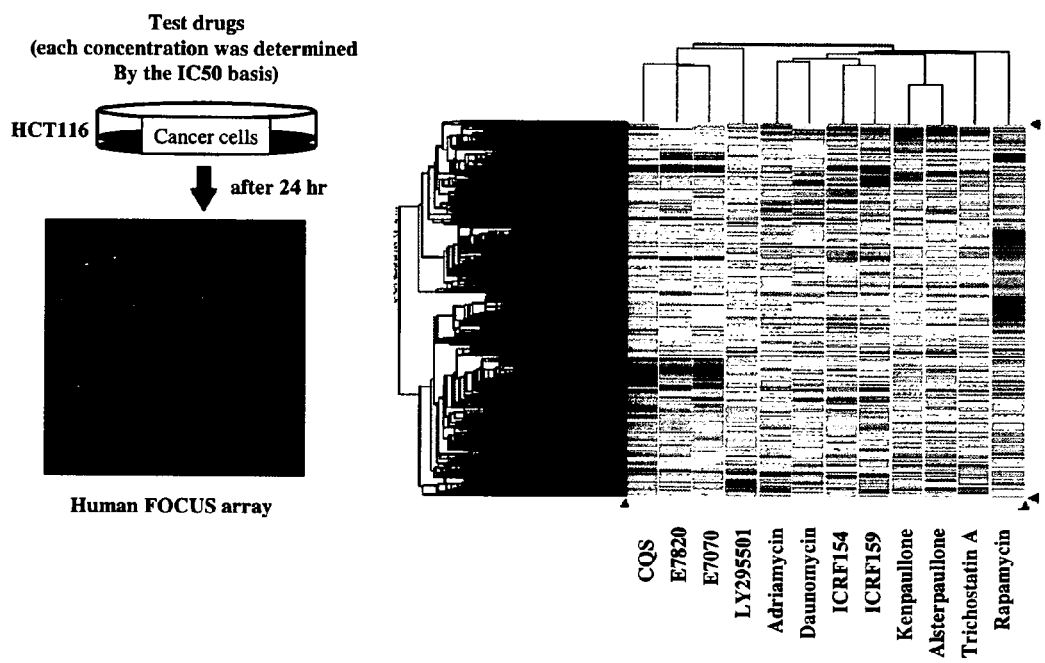
FIG. 1 shows the results of hierarchical clustering analysis in DNA microarrays in Example 1.

Embodiments of the present invention will be explained below. The following embodiments are provided for illustrative purposes only, and are not intended to limit the scope of the invention. The present invention can be embodied in various forms without departing from the spirit of the invention.

All documents cited herein, including journal articles, patent gazettes and other patent documents, are incorporated herein by reference.

As used herein, the term "halogen atom" refers to a fluorine atom, a chlorine atom, a bromine atom or an iodine atom.

As used herein, the term "$C_{1-6}$ alkyl group" refers to a linear or branched alkyl group containing 1 to 6 carbon atoms. Specific examples include a methyl group, an ethyl group, a 1-propyl group (i.e., a n-propyl group), a 2-propyl group (i.e., an i(iso)-propyl group or an isopropyl group), a 2-methyl-1-propyl group (i.e., an i-butyl group or an isobutyl group), a 2-methyl-2-propyl group (i.e., a t(tert)-butyl group), a 1-butyl group (i.e., a n-butyl group), a 2-butyl group (i.e., a s(sec)-butyl group), a 1-pentyl group (i.e., a n-pentyl group or an amyl group), a 2-pentyl group (i.e., a 1-methylbutyl group), a 3-pentyl group (i.e., a 1-ethylpropyl group), a 2-methyl-1-butyl group (i.e., a 2-methylbutyl group), a 3-methyl-1-butyl group (i.e., an isopentyl group), a 2-methyl-2-butyl group (i.e., a t(tert)-pentyl group), a 3-methyl-2-butyl group (i.e., a 1,2-dimethylpropyl group), a 2,2-dimethyl-1-propyl group (i.e., a neopentyl group), a 1-hexyl group (i.e., a n-hexyl group), a 2-hexyl group (i.e., a 1-methylpentyl group), a 3-hexyl group (i.e., a 1-ethylbutyl group), a 2-methyl-1-pentyl group (i.e., a 2-methylpentyl group), a 3-methyl-1-pentyl group (i.e., a 3-methylpentyl group), a 4-methyl-1-pentyl group (i.e., an isohexyl group), a 2-methyl-2-pentyl group (i.e., a 1,1-dimethylbutyl group), a 3-methyl-2-pentyl group (i.e., a 1,2-dimethylbutyl group), a 4-methyl-2-pentyl group (i.e., a 1,3-dimethylbutyl group), a 2-methyl-3-pentyl group (i.e., a 1-ethyl-2-methylpropyl group), a 3-methyl-3-pentyl group (i.e., a 1-ethyl-1-methylpropyl group), a 2,3-dimethyl-1-butyl group (i.e., a 2,3-dimethylbutyl group), a 3,3-dimethyl-1-butyl group (i.e., a 3,3-dimethylbutyl group), a 2,2-dimethyl-1-butyl group (i.e., a 2,2-dimethylbutyl group), a 2-ethyl-1-butyl group (i.e., a 2-ethylbutyl group), a 3,3-dimethyl-2-butyl group (i.e., a 1,2,2-trimethylpropyl group), and a 2,3-dimethyl-2-butyl group (i.e., a 1,1,2-trimethylpropyl group).

Preferred examples of the "$C_{1-6}$ alkyl group" may include a methyl group, an ethyl group, a 1-propyl group, a 2-propyl group, a 2-methyl-1-propyl group, a 2-methyl-2-propyl group, a 1-butyl group, and a 2-butyl group.

As used herein, the term "$C_{1-6}$ alkylene group" refers to a divalent group derived by removing any one hydrogen atom from the "$C_{1-6}$ alkyl group" defined above. Specific examples include a methylene group, a 1,2-ethylene group, a 1,1-ethylene group, a 1,3-propylene group, a tetramethylene group, a pentamethylene group, and a hexamethylene group.

As used herein, the term "$C_{2-6}$ alkenyl group" refers to a linear or branched alkenyl group having one double bond and containing 2 to 6 carbon atoms. Specific examples include an ethenyl group (i.e., a vinyl group), a 1-propenyl group, a 2-propenyl group (i.e., an allyl group), a 1-butenyl group, a 2-butenyl group, a 3-butenyl group, a pentenyl group, and a hexenyl group.

As used herein, the term "$C_{2-6}$ alkynyl group" refers to a linear or branched alkynyl group having one triple bond and containing 2 to 6 carbon atoms. Specific examples include an ethynyl group, a 1-propynyl group, a 2-propynyl group, a 1-butynyl group, a 2-butynyl group, a 3-butynyl group, a pentynyl group, and a hexynyl group.

As used herein, the term "$C_{3-8}$ cycloalkyl group" refers to a monocyclic or bicyclic saturated aliphatic hydrocarbon group containing 3 to 8 carbon atoms. Specific examples include a cyclopropyl group, a cyclobutyl group, a cyclopentyl group, a cyclohexyl group, a cycloheptyl group, a cyclooctyl group, a bicyclo[2.1.0]pentyl group, a bicyclo[3.1.0]hexyl group, a bicyclo[2.1.1]hexyl group, a bicyclo[4.1.0]heptyl group, a bicyclo[2.2.1]heptyl group (i.e., a norbornyl group), a bicyclo[3.3.0]octyl group, a bicyclo[3.2.1]octyl group, and a bicyclo[2.2.2]octyl group.

Preferred examples of the "$C_{3-8}$ cycloalkyl group" may include a cyclopropyl group, a cyclobutyl group, and a cyclopentyl group.

As used herein, the term "$C_{6-10}$ aryl group" refers to an aromatic cyclic hydrocarbon group containing 6 to 10 carbon atoms. Specific examples include a phenyl group, a 1-naphthyl group, a 2-naphthyl group, an indenyl group, and an azulenyl group.

Preferred examples of the "$C_{6-10}$ aryl group" may include a phenyl group.

As used herein, the term "heteroatom" refers to a nitrogen atom, an oxygen atom or a sulfur atom.

As used herein, the term "5- to 10-membered heteroaryl group" refers to an aromatic cyclic group having 5 to 10 ring member atoms, 1 to 5 of which are heteroatoms. Specific examples include a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a pyrimidinyl group, a triazinyl group, a purinyl group, a pteridinyl group, a quinolyl group, an isoquinolyl group, a naphthylizinyl group, a quinoxalinyl group, a cinnolinyl group, a quinazolinyl group, a phthalazinyl group, an imidazopyridyl group, an imidazothiazolyl group, an imidazooxazolyl group, a benzothiazolyl group, a benzoxazolyl group, a benzimidazolyl group, an indolyl group, an isoindolyl group, an indazolyl group, a pyrrolopyridyl group, a thienopyridyl group, a furopyridyl group, a benzothiadiazolyl group, a benzooxadiazolyl group, a pyridopyrimidinyl group, a benzofuryl group, a benzothienyl group, and a thienofuryl group.

Preferred examples of the "5- to 10-membered heteroaryl group" may include a furyl group, a thienyl group, a pyrrolyl group, an imidazolyl group, a thiazolyl group, a pyrazolyl group, an oxazolyl group, an isoxazolyl group, an isothiazolyl group, a pyridyl group, and a pyrimidinyl group.

As used herein, the term "3- to 10-membered non-aromatic heterocyclic group" refers to a non-aromatic cyclic group characterized by:
(1) having 3 to 10 ring member atoms;
(2) containing 1 or 2 heteroatoms as the ring member atoms;
(3) optionally containing 1 or 2 double bonds in the ring;
(4) optionally containing 1 to 3 carbonyl groups, sulfinyl groups or sulfonyl groups in the ring; and
(5) being monocyclic or bicyclic. In the case of containing a nitrogen atom as a ring member, the nitrogen atom may have a binding hand. Specific examples include an aziridinyl group, an azetidinyl group, a pyrrolidinyl group, a piperidinyl group, an azepanyl group, an azocanyl group, a piperazinyl group, a diazepanyl group, a diazocanyl group, a diazabicyclo[2.2.1]heptyl group, a morpholinyl group, a thiomorpholinyl group, a 1,1-dioxothiomorpholinyl group, an oxilanyl group, an oxetanyl group, a tetrahydrofuryl group, a dioxolanyl group, a tetrahydropyranyl group, a dioxanyl group, a tetrahydrothienyl group, a tetrahydrothiopyranyl group, an oxazolidinyl group, and a thiazolidinyl group.

Preferred examples of the "3- to 10-membered non-aromatic heterocyclic group" may include an aziridinyl group, an azetidinyl group, a pyrrolidinyl group, a piperidinyl group, an azepanyl group, a piperazinyl group, a diazepanyl group, a morpholinyl group, a thiomorpholinyl group, a 1,1-dioxothiomorpholinyl group, a tetrahydrofuryl group, and a tetrahydropyranyl group.

As used herein, the term "$C_{1-6}$ alkoxy group" refers to a group having an oxygen atom attached to the end of the "$C_{1-6}$ alkyl group" defined above. Specific examples include a methoxy group, an ethoxy group, a 1-propoxy group (i.e., a n-propoxy group), a 2-propoxy group (i.e., an i-propoxy group), a 2-methyl-1-propoxy group (i.e., an i-butoxy group), a 2-methyl-2-propoxy group (i.e., a t-butoxy group), a 1-butoxy group (i.e., a n-butoxy group), a 2-butoxy group (i.e., a s-butoxy group), a 1-pentyloxy group, a 2-pentyloxy group, a 3-pentyloxy group, a 2-methyl-1-butoxy group, a 3-methyl-1-butoxy group, a 2-methyl-2-butoxy group, a 3-methyl-2-butoxy group, a 2,2-dimethyl-1-propoxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butoxy group, a 3,3-dimethyl-1-butoxy group, a 2,2-dimethyl-1-butoxy group, a 2-ethyl-1-butoxy group, a 3,3-dimethyl-2-butoxy group, and a 2,3-dimethyl-2-butoxy group.

Preferred examples of the "$C_{1-6}$ alkoxy group" may include "$C_{1-4}$ alkoxy groups," as exemplified by a methoxy group, an ethoxy group, a 1-propoxy group, a 2-propoxy group, a 2-methyl-1-propoxy group, a 2-methyl-2-propoxy group, a 1-butoxy group, and a 2-butoxy group.

As used herein, the term "$C_{1-6}$ alkylthio group" refers to a group having a sulfur atom attached to the end of the "$C_{1-6}$ alkyl group" defined above. Specific examples include a methylthio group, an ethylthio group, a 1-propylthio group (i.e., a n-propylthio group), a 2-propylthio group (i.e., an i-propylthio group or an isopropylthio group), a 2-methyl-1-propylthio group (i.e., an i-butylthio group or an isobutylthio group), a 2-methyl-2-propylthio group (i.e., a t(tert)-butylthio group), a 1-butylthio group (i.e., a n-butylthio group), a 2-butylthio group (i.e., a s(sec)-butylthio group), a 1-pentylthio group, a 2-pentylthio group, a 3-pentylthio group, a 2-methyl-1-butylthio group, a 3-methyl-1-butylthio group, a 2-methyl-2-butylthio group, a 3-methyl-2-butylthio group, a 2,2-dimethyl-1-propylthio group, a 1-hexylthio group, a 2-hexylthio group, a 3-hexylthio group, a 2-methyl-1-pentylthio group, a 3-methyl-1-pentylthio group, a 4-methyl-1-pentylthio group, a 2-methyl-2-pentylthio group, a 3-methyl-2-pentylthio group, a 4-methyl-2-pentylthio group, a 2-methyl-3-pentylthio group, a 3-methyl-3-pentylthio group, a 2,3-dimethyl-1-butylthio group, a 3,3-dimethyl-1-butylthio group, a 2,2-dimethyl-1-butylthio group, a 2-ethyl-1-butylthio group, a 3,3-dimethyl-2-butylthio group, and a 2,3-dimethyl-2-butylthio group.

Preferred examples of the "$C_{1-6}$ alkylthio group" may include "$C_{1-4}$ alkylthio groups," as exemplified by a methylthio group, an ethylthio group, a 1-propylthio group, a 2-propylthio group, a 2-methyl-1-propylthio group, a 2-methyl-2-propylthio group, a 1-butylthio group, and a 2-butylthio group.

As used herein, the term "$C_{3-8}$ cycloalkoxy group" refers to a group having an oxygen atom attached to the end of the "$C_{3-8}$ cycloalkyl group" defined above. Specific examples include a cyclopropoxy group, a cyclobutoxy group, a cyclopentyloxy group, a cyclohexyloxy group, a cycloheptyloxy group, a cyclooctyloxy group, a bicyclo[2.1.0]pentyloxy group, a bicyclo[3.1.0]hexyloxy group, a bicyclo[2.1.1]hexyloxy group, a bicyclo[4.1.0]heptyloxy group, a bicyclo[2.2.1] heptyloxy group (i.e., a norbornyloxy group), a bicyclo[3.3.0] octyloxy group, a bicyclo[3.2.1]octyloxy group, and a bicyclo[2.2.2]octyloxy group.

Preferred examples of the "$C_{3-8}$ cycloalkoxy group" may include a cyclopropoxy group, a cyclobutoxy group, and a cyclopentyloxy group.

As used herein, the term "mono-$C_{1-6}$ alkylamino group" refers to an amino group whose one hydrogen atom is replaced by the "$C_{1-6}$ alkyl group" defined above. Specific examples include a methylamino group, an ethyl amino group, a 1-propylamino group (i.e., a n-propylamino group), a 2-propylamino group (i.e., an i-propylamino group), a 2-methyl-1-propylamino group (i.e., an i-butylamino group), a 2-methyl-2-propylamino group (i.e., a t-butylamino group), a 1-butylamino group (i.e., a n-butylamino group), a 2-butylamino group (i.e., a s-butylamino group), a 1-pentylamino group, a 2-pentylamino group, a 3-pentylamino group, a 2-methyl-1-butylamino group, a 3-methyl-1-butylamino group, a 2-methyl-2-butylamino group, a 3-methyl-2-butylamino group, a 2,2-dimethyl-1-propylamino group, a 1-hexylamino group, a 2-hexylamino group, a 3-hexylamino group, a 2-methyl-1-pentylamino group, a 3-methyl-1-pentylamino group, a 4-methyl-1-pentylamino group, a 2-methyl-2-pentylamino group, a 3-methyl-2-pentylamino group, a 4-methyl-2-pentylamino group, a 2-methyl-3-pentylamino group, a 3-methyl-3-pentylamino group, a 2,3-dimethyl-1-butylamino group, a 3,3-dimethyl-1-butylamino group, a 2,2-dimethyl-1-butylamino group, a 2-ethyl-1-butylamino group, a 3,3-dimethyl-2-butylamino group, and a 2,3-dimethyl-2-butylamino group.

As used herein, the term "di-$C_{1-6}$ alkylamino group" refers to an amino group whose two hydrogen atoms are replaced by the same or different "$C_{1-6}$ alkyl groups" defined above. Specific examples include an N,N-dimethylamino group, an N,N-diethylamino group, an N,N-di-n-propylamino group, an N,N-di-i-propylamino group, an N,N-di-n-butylamino group, an N,N-di-i-butylamino group, an N,N-di-s-butylamino group, an N,N-di-t-butylamino group, an N-ethyl-N-methylamino group, an N-n-propyl-N-methylamino group, an N-i-propyl-N-methylamino group, an N-n-butyl-N-methylamino group, an N-i-butyl-N-methylamino group, an N-s-butyl-N-methylamino group, and an N-t-butyl-N-methylamino group.

As used herein, the term "$C_{2-7}$ acyl group" refers to a carbonyl group, to which the "$C_{1-6}$ alkyl group" defined above is attached. Specific examples include, for example, an acetyl group, a propionyl group, an isopropionyl group, a butyryl group, an isobutyryl group, a valeryl group, an isovaleryl group, and a pivaloyl group.

As used herein, the term "$C_{2-7}$ alkoxycarbonyl group" refers to a carbonyl group, to which the "$C_{1-6}$ alkoxy group" defined above is attached. Specific examples include, for example, a methoxycarbonyl group, an ethoxycarbonyl group, a 1-propyloxycarbonyl group, a 2-propyloxycarbonyl group, and a 2-methyl-2-propoxy group (i.e., a t-butoxycarbonyl group).

As used herein, the term "$C_{2-5}$ alkoxycarbonyl group" refers to a carbonyl group, to which the "$C_{1-4}$ alkoxy group" defined above is attached. Specific examples include, for example, a methoxycarbonyl group, an ethoxycarbonyl group, a 1-propyloxycarbonyl group, a 2-propyloxycarbonyl group, and a 2-methyl-2-propoxy group.

As used herein, the phrase "optionally substituted" or "substituted" means "optionally having one or more substituents in any combination at a substitutable site(s)" or "having one or more substituents in any combination at a substitutable site(s)." As used herein, specific examples of substituents include, for example, a halogen atom, a hydroxyl group, a thiol group, a nitro group, a cyano group, a formyl group, a carboxyl group, an amino group, a silyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heteroaryl group, a 3- to 10-membered non-aromatic heterocyclic group, a $C_{1-6}$ alkoxy group, a $C_{1-6}$ alkylthio group, a $C_{3-8}$ cycloalkoxy group, a mono-$C_{1-6}$ alkylamino group, a di-$C_{1-6}$ alkylamino group, a $C_{2-7}$ acyl group or a $C_{2-7}$ alkoxycarbonyl group (provided that the amino group, the $C_{1-6}$ alkyl group, the $C_{2-6}$ alkenyl group, the $C_{2-6}$ alkynyl group, the $C_{3-8}$ cycloalkyl group, the $C_{6-10}$ aryl group, the 5- to 10-membered heteroaryl group, the 3- to 10-membered non-aromatic heterocyclic group, the $C_{1-6}$ alkoxy group, the $C_{1-6}$ alkylthio group, the $C_{3-8}$ cycloalkoxy group, the mono-$C_{1-6}$ alkylamino group, the di-$C_{1-6}$ alkylamino group, the $C_{2-7}$ acyl group and the $C_{2-7}$ alkoxycarbonyl group may each independently have 1 to 3 groups selected from the group consisting of the following substituent group). In the present invention, substituents other than those listed above may be intended in some cases.

<Substituent Group>

A halogen atom, a hydroxyl group, a thiol group, a nitro group, a cyano group, a silyl group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 3- to 10-membered non-aromatic heterocyclic group, a $C_{1-6}$ alkoxy group and a $C_{1-6}$ alkylthio group.

1. Sulfonamide-Including Compounds

In the present invention, the sulfonamide-including compound includes compounds of the following Formula (I):

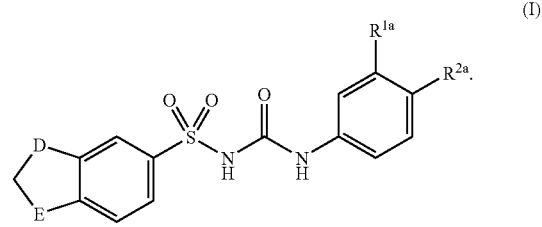

(I)

In the above Formula (I), E represents —O—, —N(CH$_3$)—, —CH$_2$—, —CH$_2$CH$_2$— or —CH$_2$O—, D represents —CH$_2$— or —O—, $R^{1a}$ represents a hydrogen atom or a halogen atom, and $R^{2a}$ represents a halogen atom or a trifluoromethyl group.

The compounds of Formula (I) according to the present invention can be prepared in a known manner, for example as described in European Patent Publication No. 0222475A1, which is hereby incorporated by reference.

In Formula (I), a preferred compound is LY186641 or LY295501.

LY186641 refers to N-[[(4-chlorophenyl)amino]carbonyl]-2,3-dihydro-1H-indene-5-sulfonamide and its structural formula is shown in the following Formula (VII):

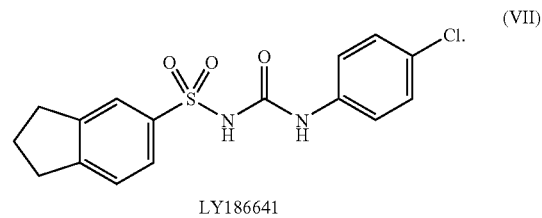 [SMILES: O=C(Nc1ccc(Cl)cc1)NS(=O)(=O)c1ccc2c(c1)CCC2]

LY186641

(VII)

LY186641 can be prepared in a known manner, for example as described in European Patent Publication No. 0222475A1, which is hereby incorporated by reference.

In the present invention, LY295501 refers to N-[[(3,4-dichlorophenyl)amino]-carbonyl]-2,3-dihydrobenzofuran-5-sulfonamide and its structural formula is shown in the following Formula (VIII):

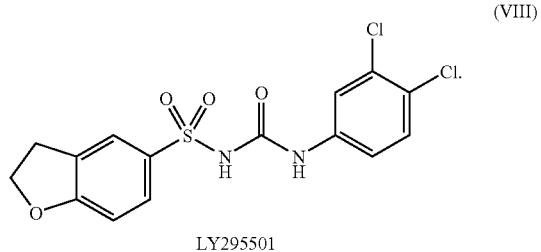 [SMILES: O=C(Nc1ccc(Cl)c(Cl)c1)NS(=O)(=O)c1ccc2c(c1)CCO2]

LY295501

(VIII)

LY295501 can be prepared in a known manner, for example as described in European Patent Publication No. 0222475A1 and/or European Patent Publication No. 0555036A2, both of which are hereby incorporated by reference.

In the present invention, the sulfonamide-including compound also includes compounds of the following Formula (II):

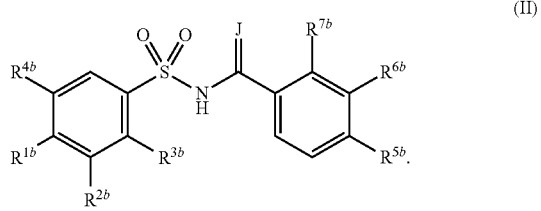

(II)

In Formula (II), J represents —O— or —NH—, $R^{1b}$ represents a hydrogen atom, a halogen atom, an optionally substituted $C_{1-6}$ alkyl group, an optionally substituted $C_{1-4}$ alkoxy group, an optionally substituted $C_{1-4}$ alkylthio group, an optionally substituted C2-5 alkoxycarbonyl group, a nitro group, an azido group, —O(SO$_2$)CH$_3$, —N(CH$_3$)$_2$, a hydroxyl group, a phenyl group, a substituted phenyl group, a pyridinyl group, a thienyl group, a furyl group, a quinolinyl group or a triazole group, $R^{2b}$ represents a hydrogen atom, a halogen atom, a cyano group, an optionally substituted $C_{1-6}$ alkyl group, an optionally substituted $C_{2-5}$ alkoxycarbonyl group, an optionally substituted $C_{1-4}$ alkoxy group, an optionally substituted phenyl group or an optionally substituted quinolinyl group, $R^{3b}$ represents a hydrogen atom or an optionally substituted $C_{1-4}$ alkoxy group, $R^{4b}$ represents a hydrogen atom or an optionally substituted $C_{1-6}$ alkyl group (provided that at least one of $R^{3b}$ and $R^{4b}$ is a hydrogen atom), $R^{5b}$ represents a hydrogen atom, a halogen atom, an optionally substituted $C_{1-6}$ alkyl group or a nitro group, $R^{6b}$ represents a hydrogen atom, a halogen atom or an optionally substituted $C_{1-6}$ alkyl group (provided that when $R^{6b}$ is an optionally substituted $C_{1-6}$ alkyl group, $R^{5b}$ is a hydrogen atom and $R^{7b}$ is a halogen atom), and $R^{7b}$ represents a halogen atom or an optionally substituted $C_{1-6}$ alkyl group (provided that when either $R^{5b}$ or $R^{7b}$ is an optionally substituted $C_{1-6}$ alkyl group or when $R^{7b}$ is a halogen atom or an optionally substituted $C_{1-6}$ alkyl group, either $R^{5b}$ or $R^{6b}$ is a hydrogen atom).

In Formula (II), the "$C_{1-6}$ alkyl group" may preferably include a methyl group, an ethyl group, a 1-propyl group, a 2-propyl group, a 2-methyl-1-propyl group, a 2-methyl-2-propyl group, a 1-butyl group, and a 2-butyl group. Among them, most preferred are a methyl group, an ethyl group, a 1-propyl group, and a 2-propyl group.

Likewise, in Formula (II), the optionally substituted $C_{1-6}$ alkyl group may be, for example, a trifluoromethyl group.

In Formula (II), the "$C_{1-4}$ alkoxy group" may preferably include a methoxy group, an ethoxy group, a 1-propoxy group, a 2-propoxy group, and a 1-butoxy group.

Likewise, in Formula (II), the optionally substituted $C_{1-4}$ alkoxy group may be, for example, —OCF$_3$.

In Formula (II), the "$C_{1-4}$ alkylthio group" may preferably include a methylthio group, an ethylthio group, a 1-propylthio group, a 2-propylthio group, a 2-methyl-1-propylthio group, a 2-methyl-2-propyl group, a 1-butylthio group, and a 2-butylthio group.

Likewise, in Formula (II), the optionally substituted $C_{1-4}$ alkylthio group may be, for example, —SCF$_3$.

In Formula (II), the "$C_{2-5}$ alkoxycarbonyl group" may preferably include a methoxycarbonyl group, an ethoxycarbonyl group, a 1-propyloxycarbonyl group, a 2-propyloxycarbonyl group, and a t-butoxycarbonyl group.

In Formula (II), examples of substituents to be introduced may include those exemplified by a $C_{1-6}$ alkyl group, a $C_{1-4}$ alkoxy group, an amino group, a hydroxyl group, a halogen atom or a silyl group.

The compounds of Formula (II) according to the present invention can be prepared in a known manner, for example as described in International Publication No. WO02/098848, which is hereby incorporated by reference.

In Formula (II), a preferred compound is LY-ASAP.

LY-ASAP refers to N-(2,4-dichlorobenzoyl)-4-chlorophenylsulfonamide and its structural formula is shown in the following Formula (XI):

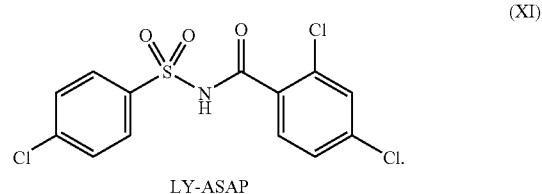 [SMILES: O=C(NS(=O)(=O)c1ccc(Cl)cc1)c1ccc(Cl)cc1Cl]

LY-ASAP (XI)

LY-ASAP can be prepared in a known manner, for example as described in International Publication No. WO02/098848, which is hereby incorporated by reference.

In the present invention, the sulfonamide-including compound may also include LY573636. In the present invention, LY573636 refers to N-(2,4-dichlorobenzoyl)-5-bromothiophene-2-sulfonamide and its structural formula is shown in the following Formula (III):

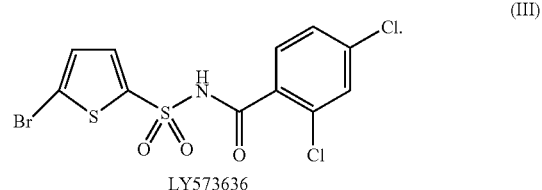 [SMILES: O=C(NS(=O)(=O)c1ccc(Br)s1)c1ccc(Cl)cc1Cl]

LY573636

(III)

LY573636 is preferably in sodium salt form.

LY573636 can be prepared in a known manner, for example, in the same manner as described in International Publication No. WO02/098848, which is hereby incorporated by reference, starting with commercially available 5-bromothiophene-2-sulfonyl chloride and 2,4-dichlorobenzoic acid.

In the present invention, the sulfonamide-including compound may also include CQS. In the present invention, CQS refers to 2-sulfanylamido-5-chloroquinoxaline and its structural formula is shown in the following Formula (IV):

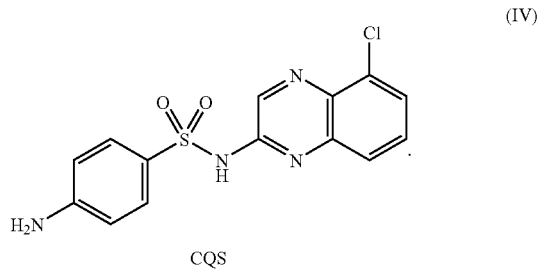 [SMILES: Nc1ccc(S(=O)(=O)Nc2cnc3c(Cl)cccc3n2)cc1]

CQS

CQS can be prepared in a known manner, for example as described in J. Am. Chem. Soc., 1947, 71, 6-10, which is hereby incorporated by reference.

Moreover, in the present invention, the sulfonamide-including compound may also include E7070. E7070 refers to N-(3-chloro-1H-indol-7-yl)-4-sulfamoylbenzenesulfonamide and its structural formula is shown in the following Formula (IX):

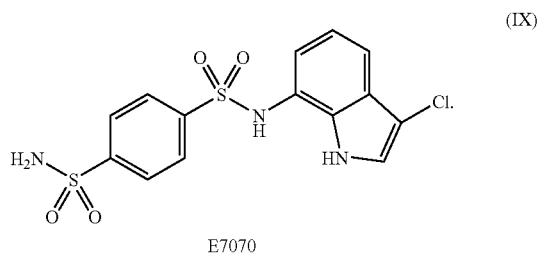 [SMILES: NS(=O)(=O)c1ccc(S(=O)(=O)Nc2cccc3c(Cl)c[nH]c23)cc1]

E7070

E7070 can be prepared in a known manner, for example as described in International Publication No. WO95/07276 or in Example 19 of JP 7-165708 A, which is hereby incorporated by reference.

In the present invention, the sulfonamide-including compound also includes compounds of the following Formula (XIV).

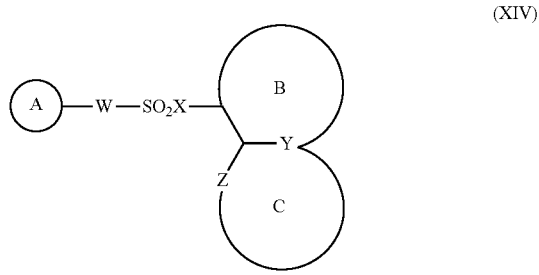

In the above Formula (XIV),
the ring A represents an optionally substituted monocyclic or bicyclic aromatic ring,
the ring B represents an optionally substituted 6-membered cyclic unsaturated hydrocarbon or an optionally substituted unsaturated 6-membered heterocyclic ring containing one nitrogen atom as a heteroatom,
the ring C represents an optionally substituted 5-membered heterocyclic ring containing one or two nitrogen atoms,
W represents a single bond or —CH=CH—,
X represents —N($R^1$)— or an oxygen atom,
Y represents:

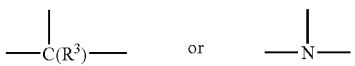

and
Z represents —N($R^2$)—.

In these formulae, $R^1$, $R^2$ and $R^3$, which may be the same or different, each independently represents a hydrogen atom or a lower alkyl group.

The "optionally substituted monocyclic or bicyclic aromatic ring" defined for the ring A refers to an aromatic hydrocarbon or an aromatic heterocyclic ring containing at least one of a nitrogen atom, an oxygen atom and a sulfur atom. Such a ring may have 1 to 3 substituents. Examples of major aromatic rings encompassed by the ring A may include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthylizine, quinoxaline, quinazoline, cinnoline, indole, isoindole, indolizine, indazole, benzofuran, benzothiophene, benzoxazole, benzimidazole, benzopyrazole, and benzothiazole. These aromatic rings may have 1 to 3 substituents, which may be the same or different. Examples of substituents may include an optionally lower alkyl- or lower cycloalkyl-substituted amino group, a lower alkyl group, a lower alkoxy group, a hydroxyl group, a nitro group, a mercapto group, a cyano group, a lower alkylthio group, a halogen atom, a group represented by the formula -a-b [wherein a represents a single bond, —($CH_2$)$_k$—, —O—($CH_2$)$_k$—, —S—($CH_2$)$_k$— or —N($R^3$)—($CH_2$)$_k$—, k represents an integer of 1 to 5, $R^3$ represents a hydrogen atom or a lower alkyl group, and b represents —$CH_2$-d (wherein d represents an optionally lower alkyl-substituted amino group, a halogen atom, a hydroxyl group, a lower alkylthio group, a cyano group or a lower alkoxy group)], a group represented by the formula -a-e-f [wherein a is as defined above, e represents —S(O)— or —S(O)$_2$—, and f represents an optionally lower alkyl- or lower alkoxy-substituted amino group, a lower alkyl group, a trifluoromethyl group, —($CH_2$)$_m$-b or —N($R^4$)—($CH_2$)$_m$-b (wherein b is as defined above, $R^4$ represents a hydrogen atom or a lower alkyl group, and m represents an integer of 1 to 5)], a group represented by the formula -a-g-h [wherein a is as defined above, g represents —C(O)— or —C(S)—, and h represents an optionally lower alkyl-substituted amino group, a hydroxyl group, a lower alkyl group, a lower alkoxy group, —($CH_2$)$_n$-b or —N($R^5$)—($CH_2$)$_n$-b (wherein b is as defined above, $R^5$ represents a hydrogen atom or a lower alkyl group, and n represents an integer of 1 to 5)], a group represented by the formula -a-N($R^6$)-g-i [wherein a and g are as defined above, $R^6$ represents a hydrogen atom or a lower alkyl group, and i represents a hydrogen atom, a lower alkoxy group or f (wherein f is as defined above)], a group represented by the formula -a-N($R^7$)-e-f (wherein a, e and f are as defined above, and R[7] represents a hydrogen atom or a lower alkyl group), or a group represented by the formula —(CH$_2$)$_p$-j-(CH$_2$)$_q$-b (wherein j represents an oxygen atom or a sulfur atom, b is as defined above, and p and q, which may be the same or different, each represent an integer of 1 to 5).

In the above examples of substituents, in the case of an amino group substituted with two alkyl groups, these alkyl groups may together form a 5- or 6-membered ring. Likewise, in a case where the ring A is a nitrogen-containing heterocyclic ring having a hydroxyl group or a mercapto group, these groups may form an oxo group or a thioxo group by taking the resonance structure.

In Formula (XIV), the "optionally substituted 6-membered cyclic unsaturated hydrocarbon" or the "optionally substituted unsaturated 6-membered heterocyclic ring containing one nitrogen atom as a heteroatom" defined for the ring B refers to, for example, benzene or pyridine whose unsaturated bonds may be partially hydrogenated. Such a ring may have one or more substituents, which may be the same or different.

The "optionally substituted 5-membered heterocyclic ring containing one or two nitrogen atoms" defined for the ring C refers to pyrrole, pyrazole or imidazole whose unsaturated bonds may be partially hydrogenated. Such a ring may have one or two substituents, which may be the same or different.

In Formula (XIV), Z represents —N(R$^2$)—. R$^2$ may be the same as or different from R$^1$ described later and represents a hydrogen atom or a lower alkyl group.

Examples of substituents which may be on the rings B and C include a halogen atom, a cyano group, a lower alkyl group, a lower alkoxy group, a hydroxyl group, an oxo group, a group represented by the formula —C(O)-r (wherein r represents a hydrogen atom, an optionally lower alkyl-substituted amino group, a lower alkyl group, a lower alkoxy group or a hydroxyl group), an optionally lower alkyl-substituted amino group, and a trifluoromethyl group.

In Formula (XIV), Y represents:

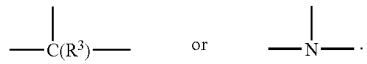

In the above formula, R$^3$ represents a hydrogen atom or a lower alkyl group.

In Formula (XIV), W represents a single bond or —CH=CH—, and X represents —N(R$^1$)— or an oxygen atom. R$^1$ may be the same as or different from R$^2$ and represents a hydrogen atom or a lower alkyl group.

In the above Formula (XIV), the "lower alkyl (group)" found in the definition of substituents which may be on R$^1$, R$^2$ and R$^3$ as well as the rings A, B and C refers to a linear or branched alkyl group containing 1 to 6 carbon atoms and has the same meaning as the "C$_{1-6}$ alkyl group" mentioned above.

The "lower cycloalkyl (group)" found in the definition of substituents which may be on the ring A refers to a cycloalkyl group containing 3 to 8 carbon atoms and has the same meaning as the "C$_{3-8}$ cycloalkyl group" mentioned above. Examples of such a lower cycloalkyl group include a cyclopropyl group, a cyclopentyl group, and a cyclohexyl group. Likewise, the "lower alkylthio (group)" refers to an alkylthio group derived from the above lower alkyl group and has the same meaning as the "C$_{1-6}$ alkylthio group" mentioned above.

The "lower alkoxy (group)" found in the definition of substituents which may be on the rings A, B and C refers to, for example, a lower alkoxy group derived from the above lower alkyl group, as exemplified by a methoxy group, an ethoxy group, a n-propoxy group, an isopropoxy group, a n-butoxy group, an isobutoxy group, and a tert-butoxy group. Among them, most preferred are a methoxy group and an ethoxy group. Likewise, examples of the "halogen atom" include a fluorine atom, a chlorine atom, a bromine atom, and an iodine atom.

The compounds of Formula (XIV) according to the present invention can be prepared in a known manner, for example as described in International Publication No. WO95/07276 and/or JP 7-165708 A.

In Formula (I), a preferred compound is the E7070 mentioned above or E7820.

E7820 refers to N-(3-cyano-4-methyl-1H-indol-7-yl)-3-cyanobenzenesulfonamide and its structural formula is shown in the following Formula (X):

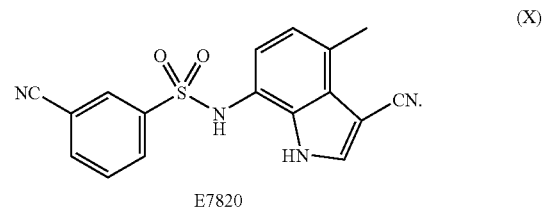

E7820 can be prepared in a known manner, for example as described in International Publication No. WO00/50395, which is hereby incorporated by reference.

These sulfonamide-including compounds may form pharmacologically acceptable salts with acids or bases. The compounds according to the present invention also encompass these pharmacologically acceptable salts. Examples of salts with acids include inorganic acid salts (e.g., hydrochloride salt, hydrobromide salt, sulfate salt, phosphate salt), as well as salts with organic acids such as formic acid, acetic acid, lactic acid, succinic acid, fumaric acid, maleic acid, citric acid, tartaric acid, benzoic acid, methanesulfonic acid, benzenesulfonic acid, p-toluenesulfonic acid and trifluoroacetic acid. Likewise, examples of salts with bases include alkali metal salts (e.g., sodium salt, potassium salt), alkaline earth metal salts (e.g., calcium salt, magnesium salt), salts with organic bases such as trimethylamine, triethylamine, pyridine, picoline, dicyclohexylamine, N,N'-dibenzylethylenediamine, arginine and lysine (organic amine salts), as well as ammonium salts.

Alternatively, these sulfonamide-including compounds may be in anhydride form or may form solvates such as hydrates. Solvates may be either hydrates or anhydrates, preferably hydrates. Solvents available for use include water, alcohols (e.g., methanol, ethanol, n-propanol) and dimethylformamide.

In a case where these compounds are present in solvate form and/or have optical isomers, the compounds according to the present invention also encompass their solvates and/or optical isomers. The compounds according to the present invention further encompass sulfonamide-including compounds that are metabolized in vivo by oxidation, reduction, hydrolysis, conjugation, etc. Furthermore, the compounds according to the present invention encompass compounds that produce sulfonamide-including compounds when metabolized in vivo by oxidation, reduction, hydrolysis, etc.

2. Angiogenesis Inhibitors

As a result of combining a sulfonamide-including compound with an angiogenesis inhibitor, the present invention provides pharmaceutical compositions and kits showing excellent angiogenesis inhibitory activity and/or anti-tumor activity.

For convenience purposes, the angiogenesis inhibitor is also referred to as an angiogenesis inhibitory agent in the following explanation.

In the present invention, the angiogenesis inhibitor is not limited in any way as long as it has an inhibitory activity on angiogenesis. Examples of such an angiogenesis inhibitor include VEGF (vascular endothelial growth factor) inhibitors (e.g., VEGF receptor kinase inhibitors, anti-VEGF antibodies (Cancer Research., 55, 5296-5301, 1995)), FGF (fibroblast growth factor) inhibitors (e.g., FGF receptor kinase inhibitors, anti-FGF antibodies (Cancer Research., 51, 61804, 1991)), PDGF (platelet-derived growth factor) inhibitors (e.g., PDGF receptor kinase inhibitors (J. Clinical Investigation., 111, 1287-95)), integrin inhibitors (e.g., αvβ3 integrin inhibitors, αvβ5 integrin inhibitors (Clinical Cancer Research., 6, 3056-61, 2000)), endogenous inhibitors (e.g., IL-12, Trombospondin-1, Endostatin, Angiostatin (International J. Cancer., 78, 361-5, 1998), COX-2 inhibitors (Annuals of N.Y. Acad. Science., 84-6, 1999)), matrix metalloprotein inhibitors (International J. Pancreatol., 21, 1-12, 1997), as well as other inhibitors (e.g., farnesyltransferase inhibitors, nitric oxide inhibitors, angiotensin converting enzyme inhibitors, HMG-CoA reductase inhibitors, Vascular Target inhibitors, methionine aminopeptidase inhibitors (Science., 282, 1324-1327, 1998)). Preferred examples are VEGF receptor kinase inhibitors, anti-VEGF antibodies, FGF receptor kinase inhibitors and anti-FGF antibodies, and more preferred examples are VEGF receptor kinase inhibitors and anti-VEGF antibodies.

(1) VEGF Receptor Kinase Inhibitors

In the present invention, the VEGF receptor kinase inhibitor may include, for example, compounds of Formula (XXIV):

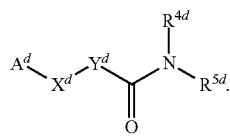
(XXIV)

(i) $A^d$ $A^d$ represents a group represented by the following formula:

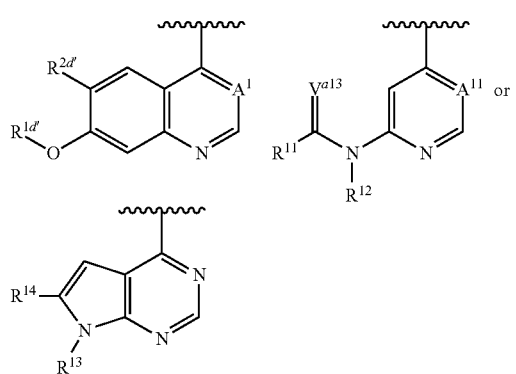

or (wherein $R^{1d'}$ represents a group represented by the formula $-V^1-V^2-V^3$ (wherein $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by the formula $-CONR^{6d}-$, a group represented by the formula $-SO_2NR^{6d}-$, a group represented by the formula $-NR^{6d}SO_2-$, a group represented by the formula $-NR^{6d}CO-$ or a group represented by the formula $-NR^{6d}-$ (wherein $R^{6d}$ represents a hydrogen atom, an optionally substituted $C_{1-6}$ alkyl group or an optionally substituted $C_{3-8}$ cycloalkyl group); and $V^3$ represents a hydrogen atom, an optionally substituted $C_{1-4}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group);

$R^{2d'}$ represents a cyano group, an optionally substituted $C_{1-6}$ alkoxy group, a carboxyl group, an optionally substituted $C_{2-7}$ alkoxycarbonyl group or a group represented by the formula $-CONV^{a11}V^{a12}$ (wherein $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group; and $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered non-aromatic heterocyclic group, a hydroxyl group, an optionally substituted $C_{1-6}$ alkoxy group or an optionally substituted $C_{3-8}$ cycloalkoxy group);

$A^1$ represents an optionally substituted carbon atom or a nitrogen atom;

$R^{11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered non-aromatic heterocyclic group or an optionally substituted mono-$C_{1-6}$ alkylamino group;

$R^{12}$ represents a hydrogen atom or an optionally substituted $C_{1-6}$ alkyl group;

$V^{a13}$ represents an oxygen atom or a sulfur atom;

$A^{11}$ represents an optionally substituted carbon atom or a nitrogen atom;

$R^{13}$ represents a hydrogen atom, an optionally substituted $C_{1-6}$ alkyl group or an optionally substituted $C_{3-8}$ cycloalkyl group; and $R^{14}$ represents a group represented by the formula $-V^{a14}-V^{a15}$ (wherein $V^{a14}$ represents a single bond or a carbonyl group; and $V^{a15}$ represents a hydrogen atom, a hydroxyl group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered non-aromatic heterocyclic group, an amino group, an optionally substituted mono-$C_{1-6}$ alkylamino group, an optionally substituted di-$C_{1-6}$ alkylamino group, a formyl group, a carboxyl group or an optionally substituted $C_{2-7}$ alkoxycarbonyl group)).

(ii) $X^d$ $X^d$ represents an oxygen atom or a sulfur atom.

(iii) $Y^d$ $Y^d$ represents a group represented by the following formula:

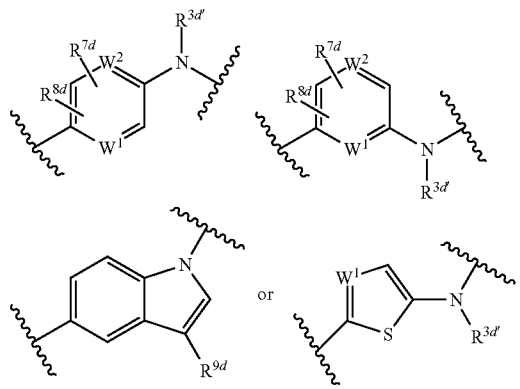

(wherein $R^{3d'}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group;

$R^{7d}$ and $R^{8d}$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by the formula —$CONV^{d1}V^{d2}$ (wherein $V^{d1}$ and $V^{d2}$ each independently represent a hydrogen atom or an optionally substituted $C_{1-6}$ alkyl group);

$R^{9d}$ represents a hydrogen atom, a halogen atom or a $C_{1-6}$ alkyl group; and $W^1$ and $W^2$ each independently represent an optionally substituted carbon atom or a nitrogen atom).

(iv) $R^{4d}$ $R^{4d}$ represents a hydrogen atom, an optionally substituted $C_{1-4}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group.

(v) $R^{5d}$ $R^{5d}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group.

The compounds of Formula (XXIV) can be prepared in a known manner, for example as described in International Publication No. WO02/032872, International Publication No. WO2004/020434, and/or International Publication No. WO2005/063713. Each of these publications are hereby incorporated by reference In the present invention, the VEGF receptor kinase inhibitor may preferably include compounds of Formula (XXV):

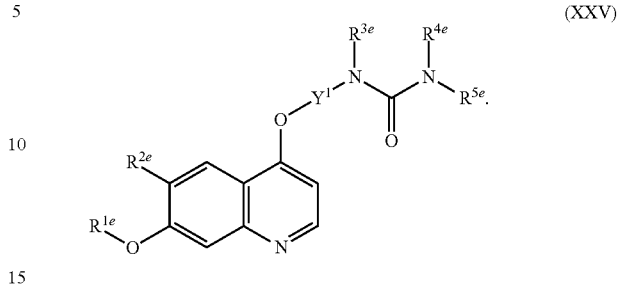

Formula (XXV) is a preferred example of the compounds of Formula (XXIV).

(i) $R^{1e}$ $R^{1e}$ represents a group represented by the formula —$V^{1e}$—$V^{2e}$—$V^{3e}$ (wherein $V^{1e}$ represents an optionally substituted $C_{1-6}$ alkylene group; $V^{2e}$ represents a single bond, an oxygen atom, a sulfur atom, a carbonyl group, a sulfinyl group, a sulfonyl group, a group represented by the formula —$CONR^{6e}$—, a group represented by the formula —$SO_2NR^{6e}$—, a group represented by the formula —$NR^{6e}SO_2$—, a group represented by the formula —$NR^{6e}CO$— or a group represented by the formula —$NR^{6e}$— (wherein $R^{6e}$ represents a hydrogen atom, an optionally substituted $C_{1-6}$ alkyl group or an optionally substituted $C_3$-8 cycloalkyl group); and $V^{3e}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group).

Preferred examples of $R^{1e}$ include a $C_{1-6}$ alkyl group. In this case, however, $R^{1e}$ may have one or more substituents selected from a 3- to 10-membered non-aromatic heterocyclic group which may have a $C_{1-6}$ alkyl group, a hydroxyl group, a $C_{1-6}$ alkoxy group, an amino group, a mono-$C_{1-6}$ alkylamino group and a di-$C_{1-6}$ alkylamino group.

More preferred examples of $R^{1e}$ include a methyl group or a group represented by any of the following formulae:

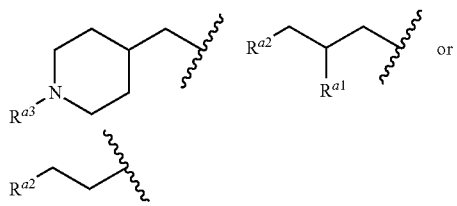

(wherein $R^{a3}$ represents a methyl group; $R^{a1}$ represents a hydrogen atom or a hydroxyl group; and $R^{a2}$ represents a methoxy group, an ethoxy group, a 1-pyrrolidinyl group, a 1-piperidinyl group, a 4-morpholinyl group, a dimethylamino group or a diethylamino group).

Even more preferred examples of $R^{1e}$ include a methyl group or a 2-methoxyethyl group.

(ii) $R^{2e}$ $R^{2e}$ represents a cyano group, an optionally substituted $C_{1-6}$ alkoxy group, a carboxyl group, an optionally substituted $C_{2-7}$ alkoxycarbonyl group or a group represented by the formula —CONV$^{e11}$V$^{e12}$ (wherein V$^{e11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group; and V$^{e12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered non-aromatic heterocyclic group, a hydroxyl group, an optionally substituted $C_{1-6}$ alkoxy group or an optionally substituted $C_{3-8}$ cycloalkoxy group).

Preferred examples of R$^{2e}$ include a cyano group or a group represented by the formula —CONV$^{e11}$V$^{e12}$ (wherein V$^{e11}$ and V$^{e12}$ are as defined above).

More preferred examples of R$^{2e}$ include a cyano group or a group represented by the formula —CONHV$^{e16}$ (wherein V$^{e16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that V$^{e16}$ may have one or more substituents selected from a halogen atom, a cyano group, a hydroxyl group and a $C_{1-6}$ alkoxy group).

Even more preferred examples of R$^{2e}$ include a group represented by the formula —CONHV$^{e17}$ (wherein V$^{e17}$ represents a hydrogen atom, a $C_{1-6}$ alkyl group or a $C_{1-6}$ alkoxy group).

Most preferred examples of R$^{2e}$ include a group represented by the formula —CONHV$^{e18}$ (wherein V$^{e18}$ represents a hydrogen atom, a methyl group or a methoxy group).

(iii) Y$^1$

Y$^1$ represents a group represented by the following formula:

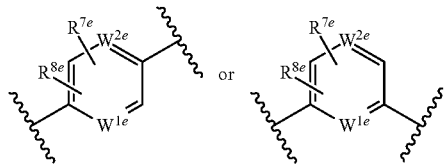

(wherein R$^{7e}$ and R$^{8e}$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, a formyl group, an optionally substituted $C_{2-7}$ acyl group, an optionally substituted $C_{2-7}$ alkoxycarbonyl group or a group represented by the formula —CONV$^{e1}$V$^{e2}$ (wherein V$^{e1}$ and V$^{e2}$ each independently represent a hydrogen atom or an optionally substituted $C_{1-6}$ alkyl group); and W$^{1e}$ and W$^{2e}$ each independently represent an optionally substituted carbon atom or a nitrogen atom).

Preferred examples of Y$^1$ include a group represented by the following formula:

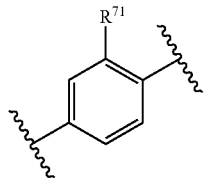

(wherein R$^{71}$ represents a hydrogen atom or a halogen atom).

(iv) R$^{3e}$ and R$^{4e}$

R$^{3e}$ and R$^{4e}$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group.

Preferred examples of R$^{3e}$ and R$^{4e}$ include a hydrogen atom.

(v) R$^{5e}$

R$^{5e}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group.

Preferred examples of R$^{5e}$ include a hydrogen atom, a $C_{1-6}$ alkyl group, a $C_{3-8}$ cycloalkyl group or a $C_{6-10}$ aryl group (provided that R$^{5e}$ may have one or more substituents selected from a halogen atom and a methanesulfonyl group).

More preferred examples of R$^{5e}$ include a methyl group, an ethyl group or a cyclopropyl group.

Moreover, preferred examples of the compounds of Formula (XXV) may include compounds of Formula (V):

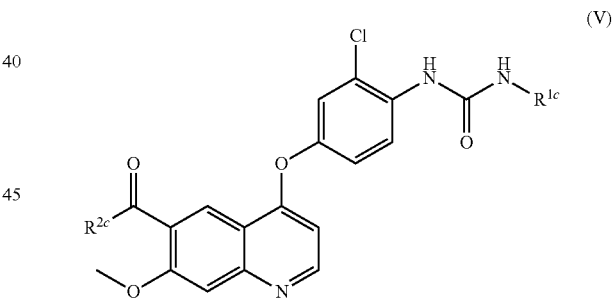

(V)

[wherein R$^{1c}$ represents a hydrogen atom, a methyl group, an ethyl group, a n-propyl group or a cyclopropyl group, and R$^{2c}$ represents —NH$_2$ or —NHOCH$_3$].

R$^{1c}$ may have a substituent such as an alkyl group (e.g., a methyl group, an ethyl group, a propyl group, a butyl group), an alkoxy group (e.g., a methoxy group, an ethoxy group, a propoxy group, a butoxy group), an amino group, a hydroxyl group, a halogen atom or a silyl group.

Preferred examples of the compounds of Formula (XXV) may also include:

N-(4-(6-cyano-7-(2-methoxyethoxy)-4-quinolyl)oxy-2-fluorophenyl)-N'-(4-fluorophenyl)urea, N-(2-chloro-4-((6-cyano-7-((1-methyl-4-piperidyl)methoxy)-4-quinolyl)oxy)phenyl)-N'-cyclopropylurea, N-(4-((6-cyano-7-(((2R)-3-(diethylamino)-2-hydroxypropyl)oxy)-4-quinolyl)oxy)phenyl)-N'-(4-fluorophenyl)urea, N-(4-(((6-cyano-7-(((2R)-2-hydroxy-3-(1-pyrrolidino)propyl)oxy)-4-quinolyl)oxy)phenyl)-N'-(4-fluorophenyl)urea,
4-(3-chloro-4-(cyclopropylaminocarbonyl)aminophenoxy)-7-methoxy-6-quinolinecarboxamide,
4-(3-chloro-4-(cyclopropylaminocarbonyl)aminophenoxy)-7-(2-methoxyethoxy)-6-quinolinecarboxamide,
N6-cyclopropyl-4-(3-chloro-4-(((cyclopropylamino)carbonyl)amino)phenoxy)-7-methoxy-6-quinolinecarboxamide,
N6-(2-methoxyethyl)-4-(3-chloro-4-(((cyclopropylamino)carbonyl)amino)phenoxy)-7-methoxy-6-quinolinecarboxamide,
N6-(2-fluoroethyl)-4-(3-chloro-4-(((cyclopropylamino)carbonyl)amino)phenoxy)-7-methoxy-6-quinolinecarboxamide,
N6-methoxy-4-(3-chloro-4-(((cyclopropylamino)carbonyl)amino)phenoxy)-7-methoxy-6-quinolinecarboxamide,
N6-methyl-4-(3-chloro-4-(((cyclopropylamino)carbonyl)amino)phenoxy)-7-methoxy-6-quinolinecarboxamide,
N6-ethyl-4-(3-chloro-4-(((cyclopropylamino)carbonyl)amino)phenoxy)-7-methoxy-6-quinolinecarboxamide,
4-(3-fluoro-4-(cyclopropylaminocarbonyl)aminophenoxy)-7-(2-methoxyethoxy)-6-quinolinecarboxamide,
4-(3-chloro-4-(cyclopropylaminocarbonyl)aminophenoxy)-7-(2-hydroxyethoxy)-6-quinolinecarboxamide,
4-(3-chloro-4-(cyclopropylaminocarbonyl)aminophenoxy)-7-((2S)-2,3-dihydroxypropyl)oxy-6-quinolinecarboxamide,
4-(3-chloro-4-(methylaminocarbonyl)aminophenoxy)-7-methoxy-6-quinolinecarboxamide,
4-(3-chloro-4-(ethylaminocarbonyl)aminophenoxy)-7-methoxy-6-quinolinecarboxamide,
N6-methoxy-4-(3-chloro-4-(((ethylamino)carbonyl)amino)phenoxy)-7-methoxy-6-quinolinecarboxamide,
4-(3-chloro-4-(cyclopropylaminocarbonyl)aminophenoxy)-7-(2-ethoxyethoxy)-6-quinolinecarboxamide,
4-(4-((cyclopropylamino)carbonyl)aminophenoxy)-7-(2-methoxyethoxy)-6-quinolinecarboxamide,
N-(2-fluoro-4-((6-carbamoyl-7-methoxy-4-quinolyl)oxy)phenyl)-N'-cyclopropylurea,
N6-(2-hydroxyethyl)-4-(3-chloro-4-(((cyclopropylamino)carbonyl)amino)phenoxy)-7-methoxy-6-quinolinecarboxamide,
4-(3-chloro-4-(1-propylaminocarbonyl)aminophenoxy)-7-methoxy-6-quinolinecarboxamide,
4-(3-chloro-4-(cis-2-fluoro-cyclopropylaminocarbonyl)aminophenoxy)-7-methoxy-6-quinolinecarboxamide,
N6-methyl-4-(3-chloro-4-(((cyclopropylamino)carbonyl)amino)phenoxy)-7-(2-methoxyethoxy)-6-quinolinecarboxamide,
N6-methyl-4-(3-chloro-4-(((ethylamino)carbonyl)amino)phenoxy)-7-methoxy-6-quinolinecarboxamide,
4-(3-chloro-4-(cyclopropylaminocarbonyl)aminophenoxy)-7-(2-(4-morpholino)ethoxy)-6-quinolinecarboxamide,
4-(3-chloro-4-(2-fluoroethylaminocarbonyl)aminophenoxy)-7-methoxy-6-quinolinecarboxamide,
N6-((2R)tetrahydro-2-furanylmethyl)-4-(3-chloro-4-(((methylamino)carbonyl)amino)phenoxy)-7-methoxy-6-quinolinecarboxamide,
4-(3-fluoro-4-(ethylaminocarbonyl)aminophenoxy)-7-methoxy-6-quinolinecarboxamide,
4-(3-chloro-4-(((cyclopropylamino)carbonyl)amino)phenoxy)-7-((2R)-2-hydroxy-3-(1-pyrrolidino)propoxy)-6-quinolinecarboxamide,
N6-methyl-4-(3-chloro-4-(((methylamino)carbonyl)amino)phenoxy)-7-((2R)-3-diethylamino-2-hydroxypropoxy)-6-quinolinecarboxamide,
N6-methyl-4-(3-chloro-4-(((ethylamino)carbonyl)amino)phenoxy)-7-((2R)-3-diethylamino-2-hydroxypropoxy)-6-quinolinecarboxamide,
N6-methyl-4-(3-chloro-4-(((methylamino)carbonyl)amino)phenoxy)-7-((2R)-2-hydroxy-3-(1-pyrrolidino)propoxy)-6-quinolinecarboxamide,
N6-methyl-4-(3-chloro-4-(((ethylamino)carbonyl)amino)phenoxy)-7-((2R)-2-hydroxy-3-(1-pyrrolidino)propoxy)-6-quinolinecarboxamide,
N6-methyl-4-(3-chloro-4-(((methylamino)carbonyl)amino)phenoxy)-7-((1-methyl-4-piperidyl)methoxy)-6-quinolinecarboxamide,
N6-methyl-4-(3-chloro-4-(((ethylamino)carbonyl)amino)phenoxy)-7-((1-methyl-4-piperidyl)methoxy)-6-quinolinecarboxamide,
N-(4-(6-cyano-7-(2-methoxyethoxy)-4-quinolyl)oxy-2-fluorophenyl)-N'-cyclopropylurea,
N-(4-(6-cyano-7-(3-(4-morpholino)propoxy)-4-quinolyl)oxyphenyl)-N'-(3-(methylsulfonyl)phenyl)urea,
4-(4-(((cyclopropylamino)carbonyl)aminophenoxy)-7-methoxy-6-quinolinecarboxamide,
4-(3-fluoro-4-((2-fluoroethylamino)carbonyl)aminophenoxy)-7-methoxy-6-quinolinecarboxamide,
N6-(2-ethoxyethyl)-4-(3-chloro-4-(((methylamino)carbonyl)amino)phenoxy)-7-methoxy-6-quinolinecarboxamide,
4-(4-(3-ethylureido)-3-fluoro-phenoxy)-7-methoxyquinoline-6-carboxylic acid (2-cyanoethyl)amide, and
N-(4-(6-(2-cyanoethyl)carbamoyl-7-methoxy-4-quinolyl)oxy-2-fluorophenyl)-N'-cyclopropylurea.

More preferred examples of the compounds of Formula (XXV) may include:
4-(3-chloro-4-(cyclopropylaminocarbonyl)aminophenoxy)-7-methoxy-6-quinolinecarboxamide,
4-(3-chloro-4-(ethylaminocarbonyl)aminophenoxy)-7-methoxy-6-quinolinecarboxamide,
N6-methoxy-4-(3-chloro-4-(((cyclopropylamino)carbonyl)amino)phenoxy)-7-methoxy-6-quinolinecarboxamide,
4-(3-chloro-4-(methylaminocarbonyl)aminophenoxy)-7-methoxy-6-quinolinecarboxamide, and
N6-methoxy-4-(3-chloro-4-(((ethylamino)carbonyl)amino)phenoxy)-7-methoxy-6-quinolinecarboxamide.

Even more preferred examples of the compounds of Formula (XXV) may include 4-(3-chloro-4-(cyclopropylaminocarbonyl)aminophenoxy)-7-methoxy-6-quinolinecarboxamide (see Formula (XV)), and the most preferred example may be a methanesulfonate salt of 4-(3-chloro-4-(cyclopropylaminocarbonyl)aminophenoxy)-7-methoxy-6-quinolinecarboxamide.

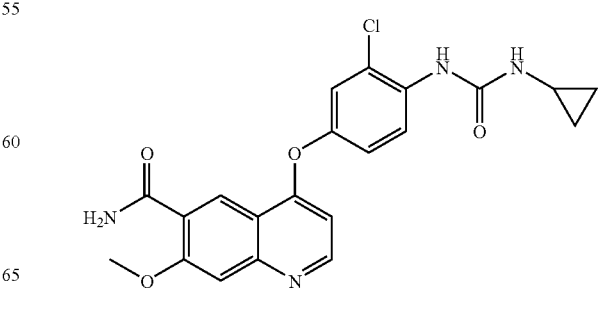

(XV)

The compounds of Formula (XXV) can be prepared in a known manner, for example as described in International Publication No. WO02/032872 and/or International Publication No. WO2005/063713, each of which are hereby incorporated by reference.

In the present invention, the VEGF receptor kinase inhibitor may also preferably include compounds of Formula (XXVI):

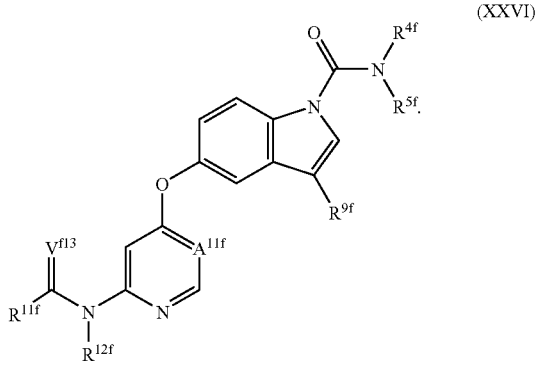

Formula (XXVI) is a preferred example of the compounds of Formula (XXIV).

(i) $R^{11f}$ $R^{11f}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered non-aromatic heterocyclic group or an optionally substituted mono-$C_{1-6}$ alkylamino group.

Preferred examples of $R^{11f}$ include an optionally substituted 3- to 10-membered non-aromatic heterocyclic group or an optionally substituted mono-$C_{1-6}$ alkylamino group.

More preferred examples of $R^{11f}$ include any one group selected from those represented by the following formulae:

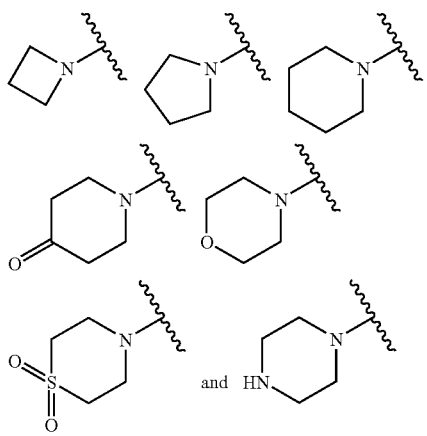

which may have one or more substituents selected from the following substituent group:

[Substituent Group]

a hydroxyl group, a $C_{1-6}$ alkyl group, a $C_{3-8}$ cycloalkyl group, and groups represented by the following formulae:

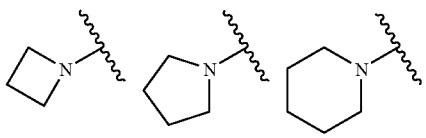

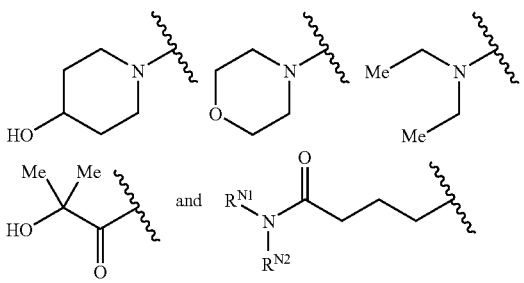

(wherein $R^{N1}$ and $R^{N2}$ each independently represent a hydrogen atom or an optionally substituted $C_{1-6}$ alkyl group; and Me denotes a methyl group).

Even more preferred examples of $R^{11f}$ include any one group selected from those represented by the following formulae:

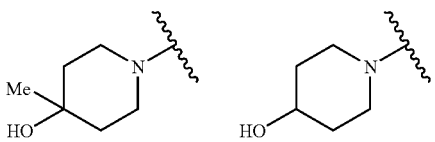

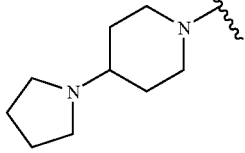

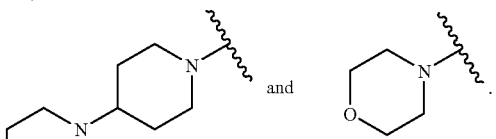

(ii) $R^{12f}$ $R^{12f}$ represents a hydrogen atom or an optionally substituted $C_{1-6}$ alkyl group.

Preferred examples of $R^{12f}$ include a hydrogen atom.

(iii) $V^{f13}$ $V^{f13}$ represents an oxygen atom or a sulfur atom.

Preferred examples of $V^{f13}$ include an oxygen atom.

(iv) $A^{11f}$ $A^{11f}$ represents an optionally substituted carbon atom or a nitrogen atom.

Preferred examples of $A^{11f}$ include a carbon atom.

(v) $R^{4f}$ $R^{4f}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group.

Preferred examples of $R^{4f}$ include a hydrogen atom.

(vi) $R^{5f}$ $R^{5f}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group or an optionally substituted 3- to 10-membered non-aromatic heterocyclic group.

Preferred examples of $R^{5f}$ include a $C_{1-6}$ alkyl group or a $C_{3-8}$ cycloalkyl group.

More preferred examples of $R^{5f}$ include a methyl group.

(vii) $R^{9f}$ $R^{9f}$ represents a hydrogen atom, a halogen atom or an optionally substituted $C_{1-6}$ alkyl group.

Preferred examples of $R^{9f}$ include a hydrogen atom.

Moreover, preferred examples of the compounds of Formula (XXVI) may include compounds of Formula (VI):

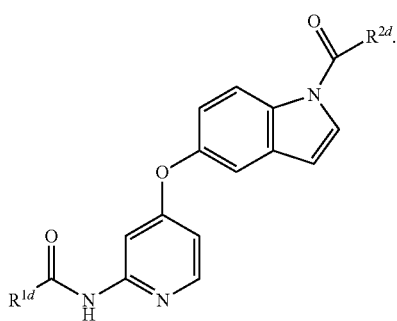

(VI)

In Formula (VI), $R^{1d}$ represents any one group selected from the group consisting of those represented by the following formulae:

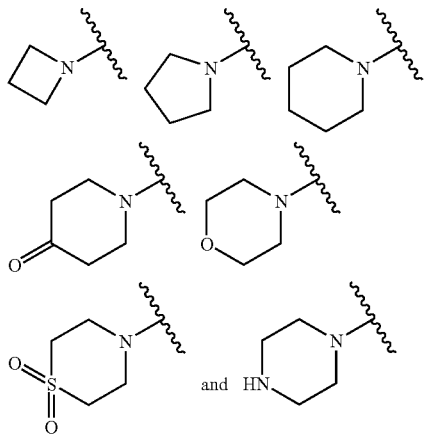

which may have one or more substituents selected from the substituent group α, and $R^{2d}$ represents —NHR$^{3d}$ (wherein $R^{3d}$ represents a methyl group, an ethyl group or a cyclopropyl group), provided that the substituent group α denotes a group consisting of a hydroxyl group, a $C_{1-6}$ alkyl group, a $C_{3-8}$ cycloalkyl group, and groups represented by the following formulae:

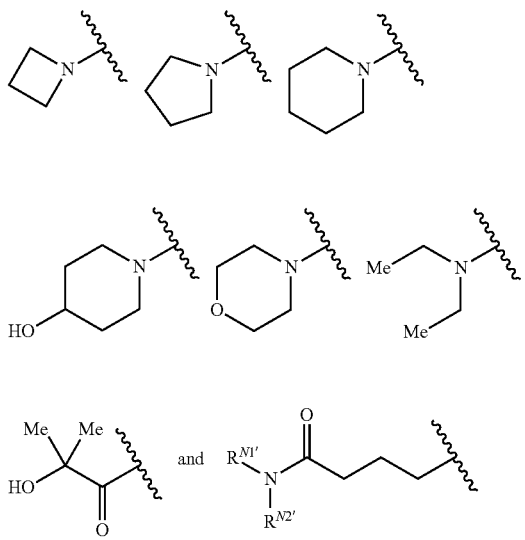

(wherein $R^{N1'}$ and $R^{N2'}$ each independently represent a hydrogen atom or a $C_{1-6}$ alkyl group).

$R^{3d}$ may have a substituent such as an alkyl group (e.g., a methyl group, an ethyl group, a propyl group, a butyl group), an alkoxy group (e.g., a methoxy group, an ethoxy group, a propoxy group, a butoxy group), an amino group, a hydroxyl group, a halogen atom (e.g., fluorine, chlorine, bromine, iodine) or a silyl group. Examples of substituents introduced into $R^{N1'}$ or $R^{N2'}$ may include the same substituents as mentioned above.

Preferred examples of the compounds of Formula (XXVI) may also include:

5-(2-(((4-hydroxy-4-methylpiperidin-1-yl)carbonyl)amino) pyridin-4-yloxy)-1H-indole-1-carboxylic acid methylamide, N1-methyl-5-(2-((4-hydroxypiperidino)carbonyl)amino-4-pyridyl)oxy-1H-1-indolecarboxamide, N1-methyl-5-(2-(((4-(pyrrolidin-1-yl)piperidin-1-yl)carbonyl)amino)pyridin-4-yloxy)-1H-1-indolecarboxamide, N1-methyl-5-(2-(((4-(piperidin-1-yl)piperidin-1-yl)carbonyl)amino)pyridin-4-yloxy)-1H-1-indolecarboxamide, and N4-(4-(1-(methylamino)carbonyl-1H-5-indolyl)oxy-2-pyridyl)-4-morpholinecarboxamide.

The compounds of Formula (XXVI) can be prepared in a known manner, for example as described in International Publication No. WO2004/020434.

In the present invention, the VEGF receptor kinase inhibitor may include, for example:

(1) N-(4-bromo-2-fluorophenyl)-6-methoxy-7-[2-(1H-1,2,3-triazol-1-yl)ethoxy]quinazoline-4-amine (hereinafter also referred to as "ZD4190"; Cancer Research., 60, 970-975, 2000, Journal of Medicinal Chemistry., 42: 5369-5389, 1999), (2) N-(4-bromo-2-fluorophenyl)-6-methoxy-7-[(1-methylpiperidin-4-yl)methoxy]quinazoline-4-amine (hereinafter also referred to as "ZD6474"; Proc. Am. Assoc. Cancer Res., 42, 583, 2001, Journal of Medicinal Chemistry., 45: 1300-1312, 2002), (3) 3-[(2,4-dimethylpyrrol-5-yl)methylene]-2-indolinone (hereinafter also referred to as "SU5416"; Cancer Res., 59, 99-106, 1999, Journal of Medicinal Chemistry., 41: 2588-2603, 1998, U.S. Pat. No. 5,792,783), (4) (Z)-3-(2,4-dimethyl-5-(2-oxo-1,2-dihydroindol-3-ylidenemethyl)-1H-pyrrol-3-yl)-propionic acid (hereinafter also referred to as "SU6668"; Cancer Res., 60, 4152-4160, 2000, Journal of Medicinal Chemistry., 42: 5120-5130, 1999), (5) 5-(5-fluoro-2-oxo-1,2-dihydroindol-3-ylidenemethyl)-2,4-dimethyl-1H-pyrrole-3-carboxylic acid (2-diethylaminoethyl)amide (hereinafter also referred to as "SU11248"; Clinical Cancer Research, 9, 327-337, 2003, Journal of Medicinal Chemistry., 46: 1116-9, 2003), (6) N,N-dimethylglycine 3-{5,6,7,13-tetrahydro-9-[(1-methylethoxy)methyl]-5-oxo-12H-indeno(2,1-a)pyrrolo(3,4-c)carbazol-12-yl}propyl ester (hereinafter also referred to as "CEP-7055"; Pro. Am. Assoc. Cancer Research, 43, 1080, 2002, Journal of Medicinal Chemistry., 46: 5375-88, 2003), (7) 3-(4-bromo-2,6-difluoro-benzyloxy)-5-[3-(4-pyrrolidin-1-yl-butyl)-ureido]-isothiazole-4-carboxylic acid amide (hereinafter also referred to as "CP-547,632"; Proc. Am. Soc. Clin. Oncology, 21, (Abstract 16), 2002, Cancer Research. 63:7301-9, 2003, WO 99/62890), (8) N-{2-chloro-4-[(6,7-dimethoxy-4-quinazolinyl)oxy]phenyl}-N'-propylurea (hereinafter also referred to as "KRN633"; Pro. Am. Assoc. Cancer Research, 43, 175, 2002, Molecular Cancer Therapeutics., 3:1639-49, 2004), (9) 1-(4-chloroanilino)-4-(4-pyridylmethyl)phthalazine (hereinafter also referred to as "PTK787"; Cancer Research, 60, 2179-2189, 2000, Journal of Medicinal Chemistry., 43:2310-23, 2000, WO98/35958) (see Formula (XII) for (1) to (9)),

(10) N-{2-chloro-4-[(6,7-dimethoxy-4-quinolyl)oxy]phenyl}-N'-(5-methyl-3-isoxazolyl)urea (hereinafter also referred to as "KRN951"; Proceedings of the American Association for Cancer Research, 45, 594, (Abstract 2571), 2004, Proceedings of the American Association for Cancer Research, 45, 595, (Abstract 2575), 2004),

(11) 4-[(4-fluoro-2-methylindol-5-yl)oxy]-6-methoxy-7-[3-(pyrrolidin-1-yl)propoxy]quinazoline (hereinafter also referred to as "AZD2171"; Cancer Research. 65:4389-400, 2005, WO00/47212), and

(12) 6-[2-(methylcarbamoyl)phenylsulfanyl]-3-E-[2-(pyridin-2-yl)ethenyl]indazole (hereinafter also referred to as "AG013736"; American Journal of Pathology. 165:35-52, 2004) (see Formula (XIII) for (10) to (12)).

ZD4190 (Cancer Research., 60, 970-975, 2000, Journal of Medicinal Chemistry., 42: 5369-5389, 1999), ZD6474 (Proc. Am. Assoc. Cancer Res., 42, 583, 2001, Journal of Medicinal Chemistry., 45: 1300-1312, 2002), SU5416 (Cancer Res., 59, 99-106, 1999, Journal of Medicinal Chemistry., 41: 2588-2603, 1998), SU6668 (Cancer Res., 60, 4152-4160, 2000, Journal of Medicinal Chemistry., 42: 5120-5130, 1999), SU11248 (Clinical Cancer Research, 9, 327-337, 2003, Journal of Medicinal Chemistry., 46: 1116-9, 2003), CEP-7055 (Pro. Am. Assoc. Cancer Research, 43, 1080, 2002, Journal of Medicinal Chemistry., 46: 5375-88, 2003), CP-547,632 (Proc. Am. Soc. Clin. Oncology, 21, (Abstract 16), 2002, Cancer Research. 63:7301-9, 2003, WO 99/62890), KRN633 (Pro. Am. Assoc. Cancer Research, 43, 175, 2002, Molecular Cancer Therapeutics., 3:1639-49, 2004), PTK787 (ZK222584) (Cancer Research, 60, 2179-2189, 2000, Journal of Medicinal Chemistry., 43:2310-23, 2000), KRN951, AZD2171 (Cancer Research. 65:4389-400, 2005, WO00/47212) and AG013736 (American Journal of Pathology. 165: 35-52, 2004) can be prepared in a known manner, for example as described in the respective documents.

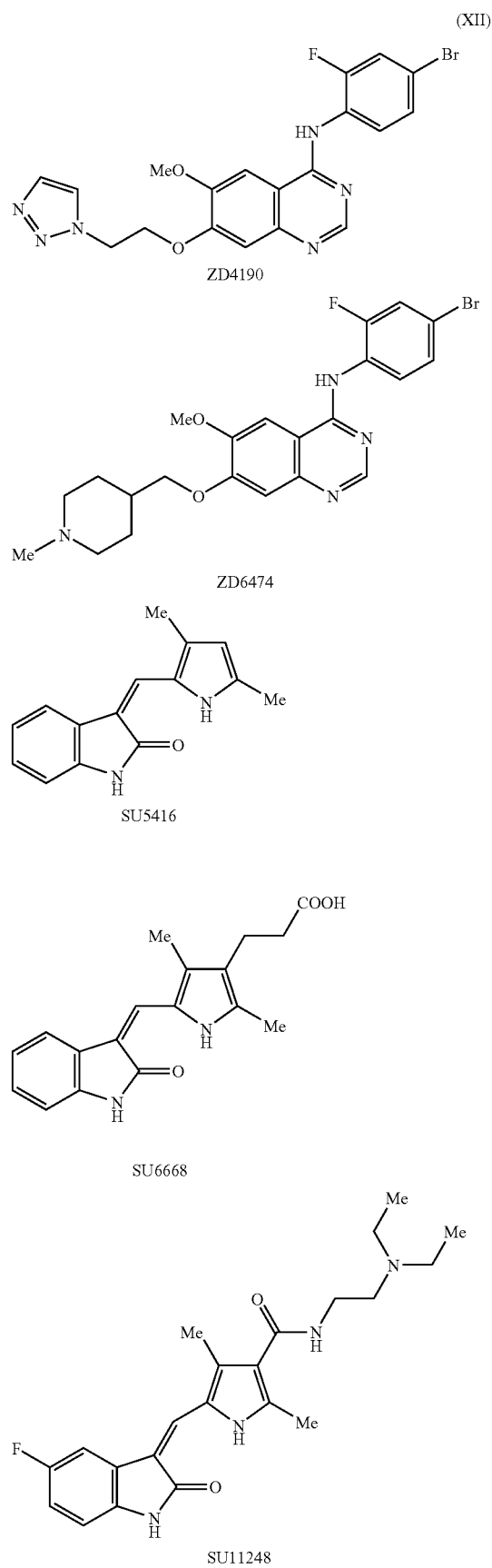

-continued

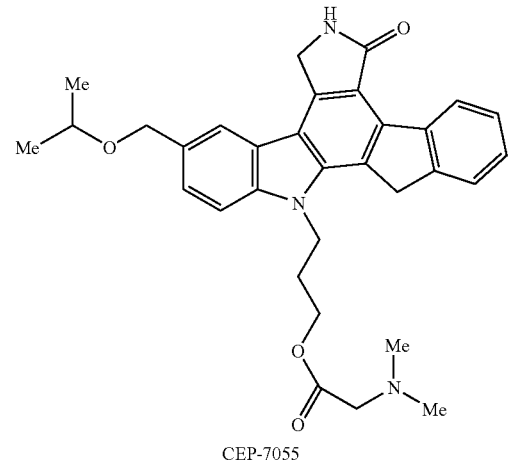
CEP-7055

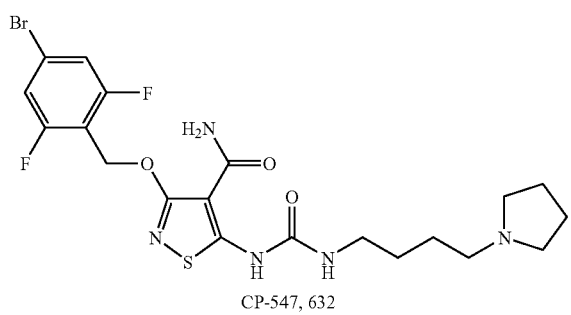
CP-547,632

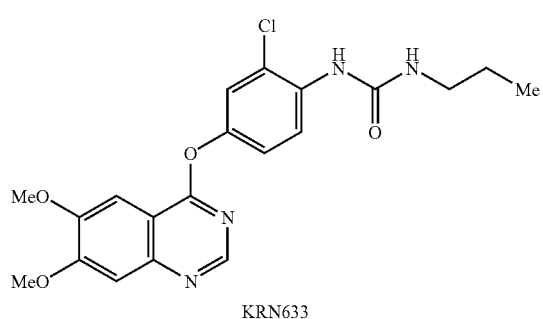
KRN633

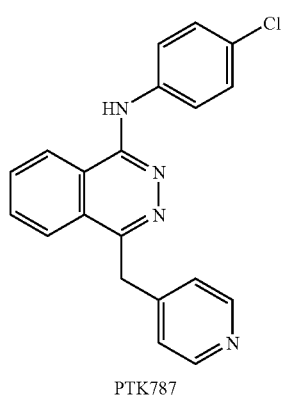
PTK787

-continued

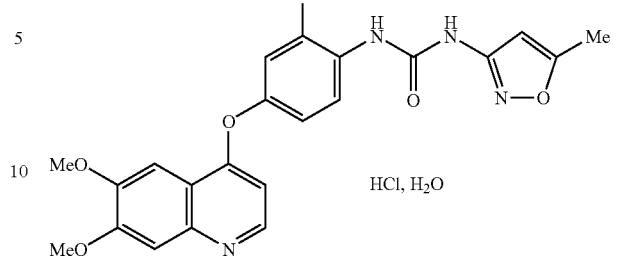
KRN951

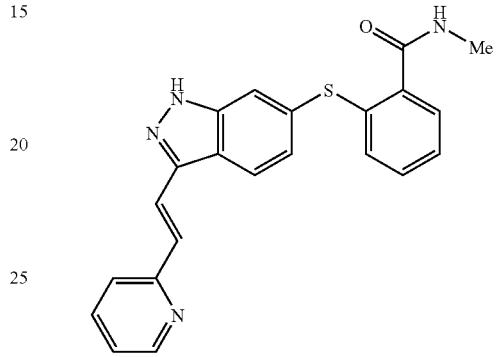
AG013736

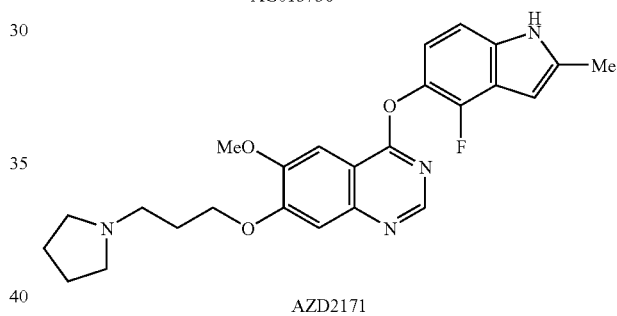
AZD2171

In the present invention, the VEGF receptor kinase inhibitor may also include:

(13) 5-((Z)-(5-fluoro-2-oxo-1,2-dihydro-3H-indol-3-ylidene)methyl)-N-((2S)-2-hydroxy-3-morpholin-4-yl-propyl)-2,4-dimethyl-1H-pyrrole-3-carboxamide (hereinafter also referred to as "SU14813"; Proceedings of the American Association for Cancer Research, 46, (Abstract 2031), 2005) (see Formula (XVI)):

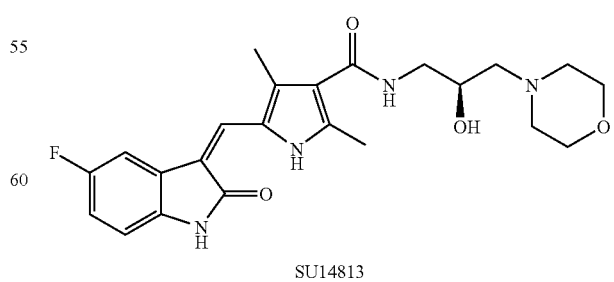
SU14813

(14) 3-((quinolin-4-ylmethyl)amino)-N-(4-(trifluoromethoxy)phenyl)thiophene-2-carboxamide (hereinafter also referred to as "OSI930"; Molecular Cancer Therapeutics., 4:1186-1197, 2005) (see Formula (XVII)):

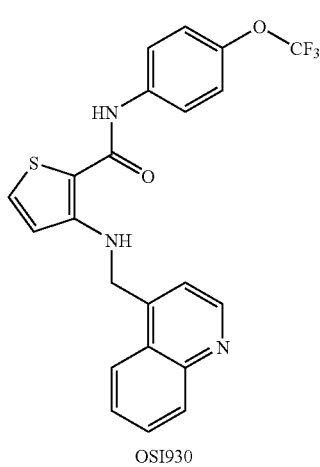

OSI930

(15) 6-(2,6-dichlorophenyl)-8-methyl-2-phenylamino-8H-pyrido[2,3-d]pyrimidin-7-one (hereinafter also referred to as "TKI-28"; Cancer Biol Ther., 4, 2005) (see Formula (XVIII)):

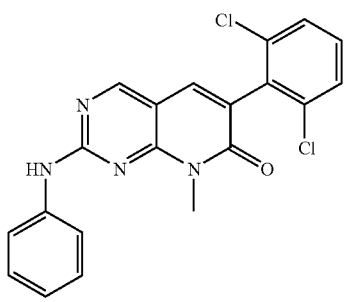

TKI-28

(16) 2-((1,6-dihydro-6-oxo-pyridin-3-ylmethyl)amino)-N-(3-(trifluoromethyl)phenyl)-3-pyridine-carboxamide (hereinafter also referred to as "ABP309"; EORTC-NCI-AACR Symp Mol Targets Cancer Ther., 2, (Abstract 172), 2004) (see Formula (XIX)):

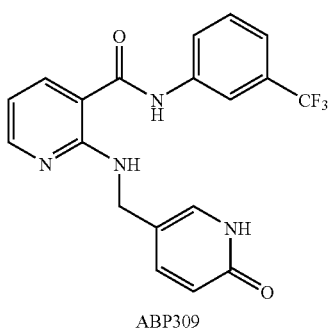

ABP309

(17) 4-(4-(4-chloro-phenylamino)-furo[2,3-d]pyridazin-7-yloxymethyl)-pyridine-2-carboxylic acid methylamide (hereinafter also referred to as "BAY 57-9352"; International Publication No. WO01/23375) (see Formula (XX)):

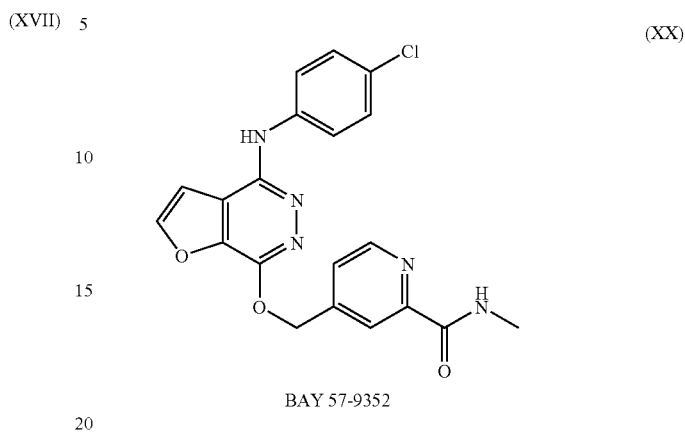

BAY 57-9352

(18) N-(3-trifluoromethyl-4-chlorophenyl)-N'-(4-(2-methyl-carbamoylpyridin-4-yl)oxyphenyl)urea (hereinafter also referred to as "BAY 43-9006"; Cancer Research., 64, 7099-7109, 2004, Organic Process Res Dev., 6, 777-81, 2002) (see Formula (XXI)):

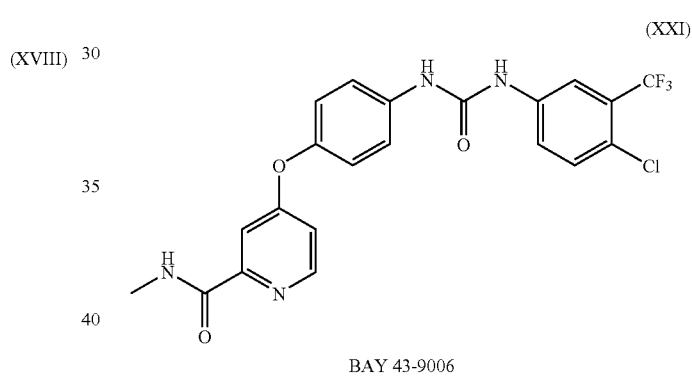

BAY 43-9006

(19) 4-amino-5-fluoro-3-(6-(4-methyl-piperazin-1-yl)-1H-benzimidazol-2-yl)-1H-quinolin-2-one (hereinafter also referred to as "CHIR258"; Clinical Cancer Research., 11, 3633-3641, 2005) (see Formula (XXII)):

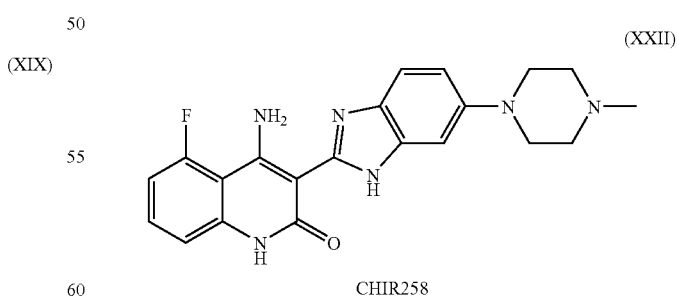

CHIR258

(20) 4-(4-(1-amino-1-methyl-ethyl)-phenyl)-2-(4-(2-morpholin-4-yl-ethyl)-phenylamino)-pyrimidine-5-carbonitrile (hereinafter also referred to as "JNJ17029259"; Molecular Pharmacology., 66, 635-647, 2004) (see Formula (XXIII)):

(XXIII)

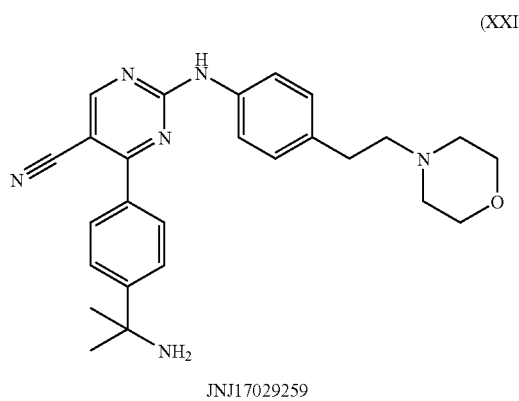

JNJ17029259

(21) [6-[4-[(4-ethylpiperazin-1-yl)methyl]phenyl]-7H-pyrrolo[2,3-d]pyrimidin-4-yl]-((R)-1-phenylethyl)amine (hereinafter also referred to as "AEE-788"; Cancer Research., 64, 4931-4941, 2004., Cancer Research., 64, 7977-7984, 2004) (see Formula (XXVII):

(XXVII)

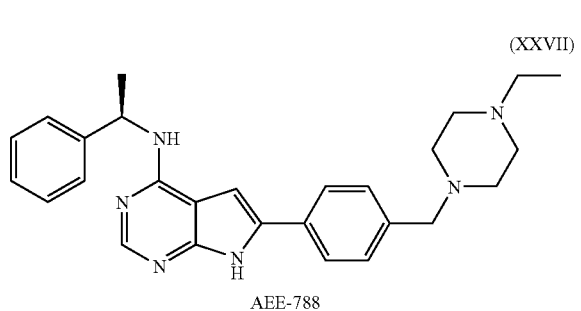 [SMILES: CCN1CCN(Cc2ccc(-c3cc4c(N[C@H](C)c5ccccc5)ncnc4[nH]3)cc2)CC1]

AEE-788

(22) 9-(1-methylethoxy)methyl-12-(3-hydroxypropyl)-6H, 7H, 13H-indeno[2,1-a]pyrrolo[3,4-c]carbazol-5-one (hereinafter also referred to as "CEP-5214"; Journal of Medicinal Chemistry., 46, 5375-5388, 2003., Cancer Research., 63, 5978-5991, 2003) (see Formula (XXVIII)):

(XXVIII)

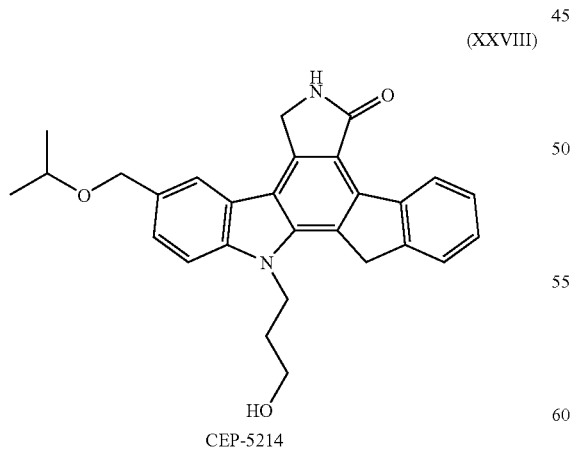

CEP-5214

(23) N-{2,4-difluorophenyl)-N'-(4-[(6,7-dimethoxy-4-quinolyl)-oxy]-2-fluorophenyl}urea (hereinafter also referred to as "KI-8751"; Journal of Medicinal Chemistry., 48, 1359-1366, 2005) (see Formula (XXIX)):

(XXIX)

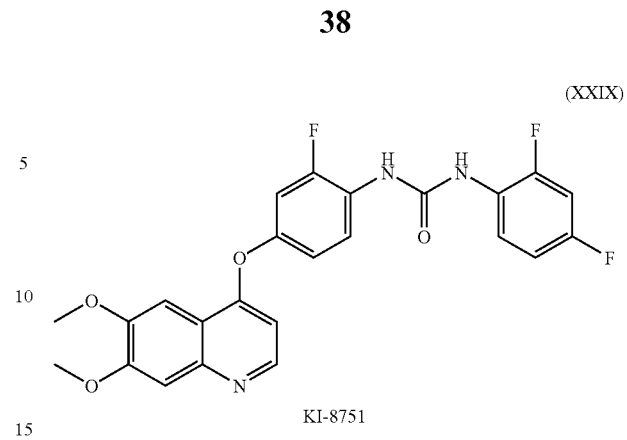

KI-8751

(24) 5-[N-methyl-N-(4-octadecyloxyphenyl)acetyl]amino-2-methylthiobenzoic acid (hereinafter also referred to as "VGA-1155"; Anticancer Research., 24, 3009-3017, 2004) (see Formula (XXX)):

(XXX)

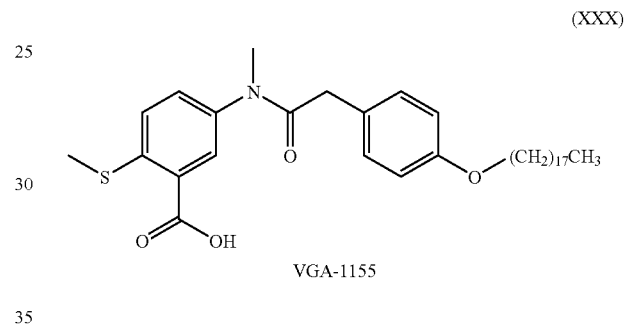

VGA-1155

(25) N-[4-(3-amino-1H-indazol-4-yl)phenyl]-N'-(2-fluoro-5-methylphenyl)urea (hereinafter also referred to as "ABT-869"; Proceedings of the American Association for Cancer Research., 46, 1407, (Abstract 5981), 2005) (see Formula (XXXI)):

(XXXI)

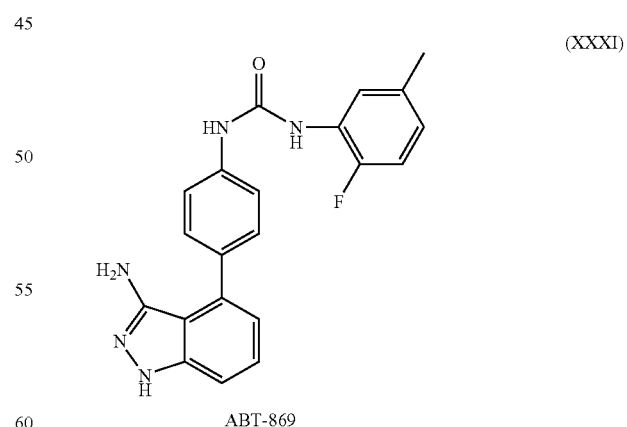

ABT-869

(26) 2-methyl-6-[2-(1-methyl-1H-imidazol-2-yl)-thieno[3,2-b]pyridin-7-yloxy]-benzo[b]thiophene-3-carboxylic acid methylamide (hereinafter also referred to as "AG-028262"; WO03/06462, U.S. 2004/009965) (see Formula (XXXII)):

(XXXII)

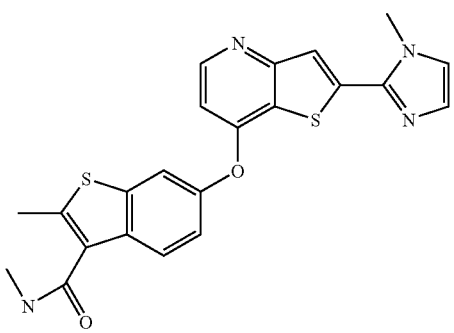

AG-028262

(27) (R)-1-(4-(4-fluoro-2-methyl-1H-indol-5-yloxy)-5-methylpyrrolo[1,2-f][1,2,4]triazin-6-yloxy)propan-2-ol (hereinafter also referred to as "BMS-540215"; Proceedings of the American Association for Cancer Research., 46, (Abstract 3033), 2005) (see Formula (XXXIII)):

(XXXIII)

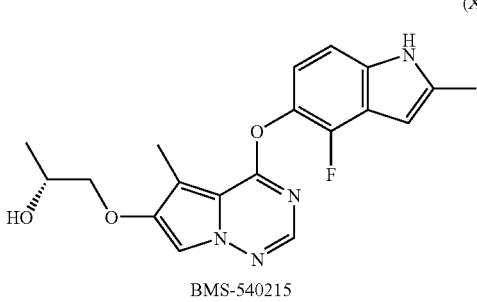

BMS-540215 and
(28) (S)—((R)-1-(4-(4-fluoro-2-methyl-1H-indol-5-yloxy)-5-methylpyrrolo[1,2-f][1,2,4]triazin-6-yloxy)propan-2-ol) 2-aminopropanonate (hereinafter also referred to as "BMS-582664"; Proceedings of the American Association for Cancer Research., 46, (Abstract 3033), 2005) (see Formula (XXXIV)):

(XXXIV)

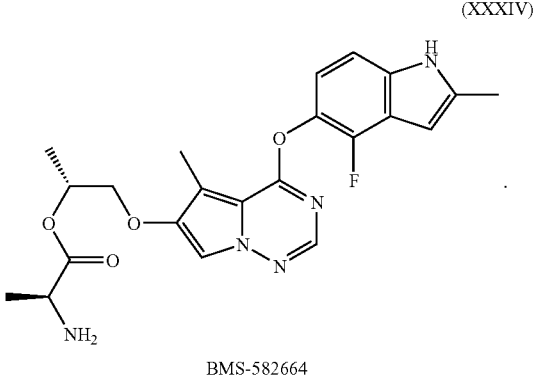 [SMILES: Cc1cc2c(F)c(Oc3ncnn4cc(OC[C@@H](C)OC(=O)[C@H](C)N)c(C)c34)ccc2[nH]1]

BMS-582664

SU14813, OSI930, TKI-28, ABP309, BAY 57-9352, BAY 43-9006, CHIR258, JNJ17029259, AEE-788, CEP-5214, KI-8751, VGA-1155, ABT-869, AG-028262, BMS-540215 and BMS-582664 can be prepared in a known manner, for example as described in the respective documents.

In the present invention, the VEGF receptor kinase inhibitor may also include, for example, BIBF1120 (WO01/27081), ZK304709 (Proceedings of the American Association for Cancer Research, 46, (Abstract 5842), 2005), Exel7647 (EORTC-NCI-AACR Symp Mol Targets Cancer Ther., (Abstract 134), 2004), AMG706 (EORTC-NCI-AACR Symp Mol Targets Cancer Ther., 2, (Abstract 151), 2004), GW-654652 (Blood., 103, 3474-3479, 2004, Proceedings of the American Association for Cancer Research, 44, 9, (Abstract 39), 2003, Proceedings of the American Association for Cancer Research, 44, 9, (Abstract 40), 2003), and GW-786034 (Proc. Am. Soc. Clin. Oncology, (Abstract 3054), 2004). BIBF1120, ZK304709, Exel7647, AMG706, GW-654652 and GW-786034 can be prepared in a known manner.

In the present invention, the VEGF receptor kinase inhibitor may further include, for example, anti-VEGF receptor antibodies. Anti-VEGF receptor antibodies are those having affinity for the VEGF receptor or a fragment thereof Such anti-VEGF receptor antibodies are preferably neutralizing antibodies that recognize and bind to the VEGF receptor to inhibit the vascular endothelial cell growth activity of VEGF. The anti-VEGF receptor antibodies may be either polyclonal or monoclonal. Also, there is no particularly limitation on the isotypes of the antibodies. The anti-VEGF receptor antibodies may also be either antibody fragments or single chain antibodies (see the section about anti-VEGF antibodies and anti-FGF antibodies described later).

The anti-VEGF receptor antibodies may preferably include 2C3 antibody (U.S. Pat. No. 6,524,583, U.S. Pat. No. 6,676,941), IMC-1121b (U.S. Pat. No. 6,811,779), IMC-18F1 (Proceedings of the American Association for Cancer Research, 45, 694, (Abstract 3005), 2004), IMC-1C11 (U.S. Pat. No. 5,747,651), and IMC-2C6 (Proceedings of the American Association for Cancer Research, 44, 1479, (Abstract 6454), 2003). These 2C3 antibody, IMC-1121b, IMC-18F1, IMC-1C11 and IMC-2C6 can be prepared in a known manner, for example as described in the respective documents.

(2) FGF Receptor Kinase Inhibitors

In the present invention, preferred FGF receptor kinase inhibitors are 1-[2-amino-6-(3,5-dimethoxyphenyl)-pyrido (2,3-d)pyrimidin-7-yl]-3-tert-butylurea (hereinafter also referred to as "PD166866"; J. M. C., 40, 2296-2303, 1997) and 1-tert-butyl-3-[2-(3-dimethylamino)propylamino-6-(3, 5-dimethoxyphenyl)-pyrido(2,3-d)pyrimidin-7-yl]urea (hereinafter also referred to as "PD173074"; EMBO J., 17, 5896-5904, 1998).

PD166866 (J. M. C., 40, 2296-2303, 1997) and PD173074 (EMBO J., 17, 5896-5904, 1998) can be prepared in a known manner.

Compounds serving as VEGF receptor kinase inhibitors and compounds serving as FGF receptor kinase inhibitors may form pharmacologically acceptable salts with acids or bases. The above receptor kinase inhibitors of the present invention also encompass these pharmacologically acceptable salts. Examples of salts with acids include inorganic acid salts (e.g., hydrochloride salt, hydrobromide salt, sulfate salt, phosphate salt), as well as salts with organic acids such as formic acid, acetic acid, lactic acid, succinic acid, fumaric acid, maleic acid, citric acid, tartaric acid, benzoic acid, methanesulfonic acid, benzenesulfonic acid, p-toluenesulfonic acid and trifluoroacetic acid. Likewise, examples of salts with bases include alkali metal salts (e.g., sodium salt, potassium salt), alkaline earth metal salts (e.g., calcium salt, magnesium salt), salts with organic bases such as trimethylamine, triethylamine, pyridine, picoline, dicyclohexylamine, N,N'-dibenzylethylenediamine, arginine and lysine (organic amine salts), as well as ammonium salts.

Alternatively, compounds serving as VEGF receptor kinase inhibitors and compounds serving as FGF receptor kinase inhibitors may be in anhydride form or may form solvates such as hydrates. Solvates may be either hydrates or anhydrates, preferably hydrates. Solvents available for use include water, alcohols (e.g., methanol, ethanol, n-propanol) and dimethylformamide.

In a case where these compounds are present in solvate form and/or have optical isomers, the VEGF receptor kinase inhibitors and FGF receptor kinase inhibitors according to the present invention also encompass their solvates and/or optical isomers. The above receptor kinase inhibitors according to the present invention further encompass VEGF receptor kinase inhibitors and FGF receptor kinase inhibitors that are metabolized in vivo by oxidation, reduction, hydrolysis, conjugation, etc. Furthermore, the above receptor kinase inhibitors according to the present invention encompass compounds that produce VEGF receptor kinase inhibitors and FGF receptor kinase inhibitors when metabolized in vivo by oxidation, reduction, hydrolysis, etc.

(3) Anti-VEGF Antibodies and Anti-FGF Antibodies

In the present invention, the anti-VEGF antibody is preferably a neutralizing antibody that recognizes and binds to VEGF to inhibit the vascular endothelial cell growth activity of VEGF. In the present invention, a preferred anti-VEGF antibody is bevacizumab. Bevacizumab is a human anti-VEGF (vascular endothelial growth factor) monoclonal antibody and can be purchased from Genentech under the name Avastin®.

Likewise, in the present invention, the anti-FGF antibody is preferably a neutralizing antibody that recognizes and binds to FGF to inhibit the fibroblast growth activity of FGF.

In the present invention, the anti-VEGF antibodies and anti-FGF antibodies may be either polyclonal or monoclonal. Also, there is no particularly limitation on the isotypes of these antibodies; the antibodies may have any isotype, for example, IgG (IgG$_1$, IgG$_2$, IgG$_3$, IgG$_4$), IgM, IgA (IgA$_1$, IgA$_2$), IgD or IgE.

Polyclonal and monoclonal antibodies can be prepared in a manner well known to those skilled in the art (Antibodies: A Laboratory Manual, E. Harlow and D. Lane, ed., Cold Spring Harbor Laboratory (Cold Spring Harbor, N.Y., 1988)).

Polyclonal antibodies can be obtained, for example, by administering an antigen to a mammal (e.g., mouse, rabbit, rat), collecting the blood from the mammal, and separating and purifying antibody molecules from the collected blood. Procedures for immunization are known to those skilled in the art and can be accomplished, e.g., by one or more administrations of an antigen. Although an antigen (including a part or all of VEGF or FGF) may be used by being dissolved in an appropriate buffer, for example, containing a commonly-used adjuvant such as complete Freund's adjuvant or aluminum hydroxide, the use of an adjuvant may be eliminated depending on the route of administration or conditions, etc.

After 1 to 2 months from the last immunization, the blood may be collected from the mammal and then separated and purified in a routine manner, e.g., by centrifugation, precipitation with ammonium sulfate or polyethylene glycol, or various chromatographic techniques to obtain polyclonal antibodies in the form of a polyclonal antiserum.

For monoclonal antibody production, for example, the hybridoma method may be used. As in the case of polyclonal antibody production, a mammal is first immunized. When the appropriate number of days have passed after the immunization, a part of the blood is preferably sampled and measured for its antibody titer in a known manner, e.g., by the ELISA method.

The spleen is then isolated from the sensitized and immunized animal to obtain B cells. The B cells are then fused with myeloma cells in a routine manner to create antibody-producing hybridomas. There is no particular limitation on the type of myeloma cells to be used and it is possible to use known types of myeloma cells. For cell fusion, any method known in the art, such as the Sendai virus method, the polyethylene glycol method or the protoplast method, may be selected and used. The resulting hybridomas are cultured in a routine manner in HAT medium (i.e., a medium containing hypoxanthine, aminopterin and thymidine) for an appropriate period of time to effect hybridoma selection. After screening to select a desired antibody-producing hybridoma, the hybridoma is cloned.

For screening, it is possible to use any method known for antibody detection, such as the ELISA method or the radioimmunoassay method. For cloning, any method known in the art may be used, including the limiting dilution method and the FACS method. The resulting hybridoma is cultured in an appropriate culture medium or is administered to a mammal (e.g., mouse peritoneal cavity) with which the hybridoma is compatible. From the culture solution or peritoneal fluid thus obtained, a desired monoclonal antibody can be isolated and purified by salting-out, ion exchange chromatography, gel filtration, affinity chromatography, etc.

Fragments and V region single chain antibodies of the above antibodies may also be used in the present invention. Such antibody fragments mean partial regions of the above polyclonal or monoclonal antibodies. Specific examples include F(ab')$_2$, Fab', Fab, Fv (variable fragment of antibody), sFv, dsFv (disulphide stabilized Fv) or dAb (single domain antibody). Moreover, the antibodies used in the present invention may also be humanized antibodies or human antibodies. Human antibodies can be created in the same manner as used for standard monoclonal antibody production, except for using a mammal whose immune system is replaced by the human immune system.

3. Pharmaceutical Compositions, Kits, Method for Cancer Prevention/Treatment, and Method for Angiogenesis Inhibition The present invention relates to pharmaceutical compositions, kits, a method for cancer prevention/treatment, and a method for angiogenesis inhibition, which are characterized in that a sulfonamide-including compound is combined with an angiogenesis inhibitor.

In the present invention, the sulfonamide-including compound is as described in "1. Sulfonamide-including compounds" and, for example, may be at least one compound selected from (1) a compound of Formula (I), preferably LY186641 or LY295501, (2) a compound of Formula (II), preferably LY-ASAP, (3) LY573636 (Formula (III)), (4) CQS (Formula (IV)), and (5) Formula (XIV), preferably E7070 or E7820. The sulfonamide-including compound is more preferably at least one compound selected from LY295501 and LY573636, and particularly preferably a sodium salt of LY573636.

Alternatively, in the present invention, the sulfonamide-including compound is preferably E7070 or E7820.

In the present invention, the angiogenesis inhibitor is as described in "2. Angiogenesis inhibitors" and, for example, may be (a) a VEGF receptor kinase inhibitor, (b) an anti-VEGF antibody, (c) a FGF receptor kinase inhibitor or (d) an anti-FGF antibody.

In the present invention, the VEGF receptor kinase inhibitor (a) may be, for example, a compound represented by at least one selected from Formula (XXIV), Formula (XI), Formula (XIII), Formulae (XVI) to (XXIII) and Formulae (XXVII) to (XXXIV). In the present invention, the VEGF receptor kinase inhibitor (a) is preferably a compound of Formula (XXV) or (XXVI), more preferably a compound of Formula (V) or (VI), even more preferably 4-(3-chloro-4-(cyclopropylaminocarbonyl)aminophenoxy)-7-methoxy-6-quinolinecarboxamide falling within the scope of Formula (V), and particularly preferably a methanesulfonate salt of 4-(3-chloro-4-(cyclopropylaminocarbonyl)aminophenoxy)-7-methoxy-6-quinolinecarboxamide. Alternatively, in the present invention, the VEGF receptor kinase inhibitor (a) is preferably a compound represented by at least one selected from Formula (XII), Formula (XIII), Formulae (XVI) to (XXIII) and Formulae (XXVII) to (XXXIV), and more preferably at least one compound selected from KRN951 (Formula (XIII)), AZD2171 (Formula (XIII)), AG013736 (Formula (XIII)), SU14813 (Formula (XVI)), OSI930 (Formula (XVII)), TKI-28 (Formula (XVIII)), ABP309 (Formula (XIX)), BAY 57-9352 (Formula (XX)), BAY 43-9006 (Formula (XXI)), CHIR258 (Formula (XXII)), JNJ17029259 (Formula (XXIII)), AEE-788 (Formula (XXXVII)), CEP-5214 (Formula (XXVIII)), KI-8751 (Formula (XXIX)), VGA-1155 (Formula (XXX)), ABT-869 (Formula (XXXI)), AG-028262 (Formula (XXXII)), BMS-540215 (Formula (XXXIII)) and BMS-582664 (Formula (XXXIV)). Alternatively, in the present invention, the VEGF receptor kinase inhibitor (a) may be, for example, an anti-VEGF receptor antibody.

In the present invention, the anti-VEGF antibody (b) is preferably bevacizumab.

In the present invention, the FGF receptor kinase inhibitor (c) is preferably PD166866 or PD173074.

In the present invention, the above compounds and angiogenesis inhibitors also encompass their pharmacologically acceptable salts or solvates (e.g., hydrates) thereof.

In the present invention, the sulfonamide compound and the angiogenesis inhibitor may be used in any combination of the above compounds and substances. Such a combination is not limited in any way and may include:

(i) a combination of a compound of Formula (I), a compound of Formula (II), LY573636, CQS or E7070 with an angiogenesis inhibitor;

(ii) a combination of a compound of Formula (XIV) with a VEGF receptor kinase inhibitor; and (iii) a combination of a compound of Formula (XIV) with an anti-VEGF antibody.

The pharmaceutical composition of the present invention comprises a sulfonamide-including compound in combination with an angiogenesis inhibitor. The pharmaceutical composition of the present invention is useful as a pharmaceutical composition for cancer treatment and as a pharmaceutical composition for angiogenesis inhibition.

Alternatively, the pharmaceutical composition of the present invention is also provided as another embodiment, i.e., a pharmaceutical composition comprising a sulfonamide-including compound, which is administered together with an angiogenesis inhibitor to a patient. The sulfonamide-including compound and the angiogenesis inhibitor may be administered simultaneously or separately. The term "simultaneously" means that these components are administered at the same timing in a single administration schedule. In this case, it is not necessary to use completely the same hour and minute for administration. The term "separately" means that these components are administered at different timings in a single administration schedule.

In the present invention, the phrase "in combination with" means a combination of compounds for combined use, and encompasses both modes in which separate compounds are administered in combination and as a mixture.

Likewise, the kit of the present invention comprises a formulation comprising a sulfonamide-including compound and a formulation comprising an angiogenesis inhibitor. The formulations contained in the kit of the present invention may be of any dosage form as long as they contain a sulfonamide-including compound or an angiogenesis inhibitor. The kit of the present invention is useful as a kit for angiogenesis inhibition or as a kit for cancer treatment.

The pharmaceutical composition and/or kit of the present invention may further be combined with one or more additional anti-cancer agents. Such additional anti-cancer agents are not limited in any way as long as they are formulations having an anti-cancer effect. Such additional anti-cancer agents include, for example, irinotecan hydrochloride (CPT-11), oxaliplatin, 5-fluorouracil (5-FU), docetaxel (Taxotere®), gemcitabine hydrochloride (Gemzar®), calcium folinate (leucovorin), gefitinib (Iressa®), erlotinib (Tarceva®), and cetuximab (Erbitux®). The above additional anti-cancer agents are particularly preferably irinotecan hydrochloride, oxaliplatin, 5-fluorouracil, calcium folinate, gefitinib, erlotinib and cetuximab in a case where the cancer type targeted by cancer therapeutic agent is colon cancer. Likewise, the above additional anti-cancer agents are particularly preferably gemcitabine hydrochloride, gefitinib, erlotinib and cetuximab for pancreas cancer, and gefitinib, erlotinib and cetuximab for renal cancer.

Moreover, in the present invention, particularly preferred combinations when using bevacizumab as an angiogenesis inhibitor are those such as shown in Table 1 in a case where the cancer type targeted by cancer therapeutic agent is colon cancer. Likewise, particularly preferred combinations are those such as shown in Table 2 for pancreas cancer and Table 3 for renal cancer.

TABLE 1

| | | Combined compounds | | | |
|---|---|---|---|---|---|
| 1 | E7070 | Bevacizumab | 5-FU | LV | Oxaliplatin | |
| 2 | E7820 | Bevacizumab | 5-FU | LV | Oxaliplatin | |
| 3 | E7070 | Bevacizumab | 5-FU | LV | Oxaliplatin | Gefitinib |
| 4 | E7820 | Bevacizumab | 5-FU | LV | Oxaliplatin | Gefitinib |
| 5 | E7070 | Bevacizumab | 5-FU | LV | Oxaliplatin | Erlotinib |
| 6 | E7820 | Bevacizumab | 5-FU | LV | Oxaliplatin | Erlotinib |
| 7 | E7070 | Bevacizumab | 5-FU | LV | Oxaliplatin | Cetuximab |
| 8 | E7820 | Bevacizumab | 5-FU | LV | Oxaliplatin | Cetuximab |
| 9 | E7070 | Bevacizumab | 5-FU | LV | CPT-11 | |
| 10 | E7820 | Bevacizumab | 5-FU | LV | CPT-11 | |
| 11 | E7070 | Bevacizumab | 5-FU | LV | CPT-11 | Gefitinib |
| 12 | E7820 | Bevacizumab | 5-FU | LV | CPT-11 | Gefitinib |
| 13 | E7070 | Bevacizumab | 5-FU | LV | CPT-11 | Erlotinib |
| 14 | E7820 | Bevacizumab | 5-FU | LV | CPT-11 | Erlotinib |
| 15 | E7070 | Bevacizumab | 5-FU | LV | CPT-11 | Cetuximab |
| 16 | E7820 | Bevacizumab | 5-FU | LV | CPT-11 | Cetuximab |
| 17 | E7070 | Bevacizumab | Gefitinib | | | |
| 18 | E7820 | Bevacizumab | Gefitinib | | | |
| 19 | E7070 | Bevacizumab | Erlotinib | | | |
| 20 | E7820 | Bevacizumab | Erlotinib | | | |
| 21 | E7070 | Bevacizumab | Cetuximab | | | |
| 22 | E7820 | Bevacizumab | Cetuximab | | | |

Table 1 shows preferred combinations in the present invention in a case where the cancer type targeted by cancer therapeutic agent is colon cancer. In the table, LV denotes calcium folinate.

TABLE 2

| | | Combined compounds | | |
|---|---|---|---|---|
| 1 | E7070 | Bevacizumab | Gemcitabine | |
| 2 | E7820 | Bevacizumab | Gemcitabine | |
| 3 | E7070 | Bevacizumab | Gemcitabine | Gefitinib |
| 4 | E7820 | Bevacizumab | Gemcitabine | Gefitinib |
| 5 | E7070 | Bevacizumab | Gemcitabine | Erlotinib |
| 6 | E7820 | Bevacizumab | Gemcitabine | Erlotinib |
| 7 | E7070 | Bevacizumab | Gemcitabine | Cetuximab |
| 8 | E7820 | Bevacizumab | Gemcitabine | Cetuximab |

Table 2 shows preferred combinations in the present invention in a case where the cancer type targeted by cancer therapeutic agent is pancreas cancer. In the table, Gemcitabine denotes gemcitabine hydrochloride.

TABLE 3

| | | Combined compounds | |
|---|---|---|---|
| 1 | E7070 | Bevacizumab | Gefitinib |
| 2 | E7820 | Bevacizumab | Gefitinib |
| 3 | E7070 | Bevacizumab | Erlotinib |
| 4 | E7820 | Bevacizumab | Erlotinib |
| 5 | E7070 | Bevacizumab | Cetuximab |
| 6 | E7820 | Bevacizumab | Cetuximab |

Table 3 shows preferred combinations in the present invention in a case where the cancer type targeted by cancer therapeutic agent is renal cancer.

The pharmaceutical composition and/or kit of the present invention can be used as an angiogenesis inhibitory agent or as a cancer therapeutic agent.

In the present invention, the term "cancer therapeutic agent" is used to mean an anti-tumor agent, a cancer prognosis improver, a cancer recurrence inhibitor, a cancer metastasis inhibitor, etc.

The effect of cancer treatment may be confirmed by findings such as roentgenogram or CT analysis or histopathological diagnosis of biopsy specimens, or alternatively, by tumor marker levels.

The pharmaceutical composition and/or kit of the present invention may be administered to mammals (e.g., human, rat, rabbit, sheep, pig, cattle, cat, dog, monkey).

The cancer type targeted by cancer therapeutic agent is not limited in any way, and examples include at least one selected from the group consisting of brain tumor, cervical cancer, esophageal cancer, tongue cancer, lung cancer, breast cancer, pancreas cancer, gastric cancer, large intestine cancer, small intestine cancer, duodenal cancer, colon cancer, rectal cancer, bladder cancer, renal cancer, liver cancer, prostate cancer, uterine cancer, ovarian cancer, thyroid gland cancer, gallbladder cancer, pharyngeal cancer, sarcoma (e.g., osteosarcoma, myosarcoma, fibrosarcoma) and melanoma. Likewise, the cancer type targeted by cancer therapeutic agent when using bevacizumab as an angiogenesis inhibitor is preferably at least one selected from pancreas cancer, renal cancer and colon cancer, and more preferably colon cancer.

In the case of using the pharmaceutical composition and/or kit of the present invention, administration may be conducted orally or parenterally.

In the case of using the pharmaceutical composition and/or kit of the present invention, the dose of the sulfonamide-including compound will vary depending on the severity of symptoms, the age, sex, body weight and differences in susceptibility of individual patients, the method of administration, the duration of administration, the interval of administration, the nature, pharmacy and type of individual pharmaceutical formulations, as well as the type of active ingredient, etc. Without being particularly limited, the daily dose for adults (body weight: 60 Kg) is usually 10 to 6000 mg, preferably 50 to 4000 mg, and more preferably 100 to 3000 mg, which may usually be given once to three times a day.

In the case of using the pharmaceutical composition and/or kit of the present invention, without being particularly limited, the daily adult dose of the VEGF receptor kinase inhibitor is usually 10 to 6000 mg, preferably 50 to 4000 mg, and more preferably 50 to 2000 mg, which may usually be given once to three times a day.

Likewise, in the case of using the pharmaceutical composition and/or kit of the present invention, without being particularly limited, the daily adult dose of the FGF receptor kinase inhibitor is usually 10 to 6000 mg, preferably 50 to 4000 mg, and more preferably 50 to 2000 mg, which may usually be given once to three times a day.

In the case of using the pharmaceutical composition and/or kit of the present invention, without being particularly limited, the dose of the anti-VEGF antibody is usually 1 to 6000 mg, preferably 10 to 2000 mg, and more preferably 10 to 1000 mg, which may usually be given once to three times a day or a week. In the case of using bevacizumab as an anti-VEGF antibody, without being particularly limited, the daily adult dose of bevacizumab is usually 10 to 6000 mg, preferably 50 to 4000 mg, and more preferably 50 to 2000 mg, which may usually be given once to three times a day.

In the case of using the pharmaceutical composition and/or kit of the present invention, without being particularly limited, the dose of the anti-FGF antibody is usually 1 to 6000 mg, preferably 10 to 2000 mg, and more preferably 10 to 1000 mg, which may usually be given once to three times a day or a week.

The amount of the sulfonamide-including compound to be used is not limited in any way and will vary depending on individual combinations with the VEGF receptor kinase inhibitor, anti-VEGF antibody, FGF receptor kinase inhibitor or anti-FGF antibody. For example, it is about a 0.01- to 100-fold excess (by weight), more preferably about a 0.1- to 10-fold excess (by weight), of the VEGF receptor kinase inhibitor, anti-VEGF antibody, FGF receptor kinase inhibitor or anti-FGF antibody.

The pharmaceutical composition of the present invention may be formulated into various dosage forms, for example, oral solid formulations or parenteral formulations including injections, suppositories, ointments and cataplasm.

Likewise, the sulfonamide-including compound and the angiogenesis inhibitor contained in the kit of the present invention may each be formulated into various dosage forms, for example, oral solid formulations or parenteral formulations including injections, suppositories, ointments and cataplasm.

To prepare oral solid formulations, these active ingredients may be supplemented with excipients and, if necessary, with binders, disintegrating agents, lubricants, coloring agents, flavoring agents and the like, followed by formulation in a routine manner into tablets, coated tablets, granules, fine granules, powders, capsules, etc. It is also possible to prepare oral non-solid formulations such as syrups, when needed.

Examples of excipients include lactose, corn starch, sucrose, glucose, sorbit, crystalline cellulose, and silicon dioxide. Examples of binders include polyvinyl alcohol, ethylcellulose, methylcellulose, gum arabic, hydroxypropylcellulose, and hydroxypropylmethylcellulose. Examples of lubricants include magnesium stearate, talc, and silica. Examples of coloring agents include those permitted for use in pharmaceutical preparations. Examples of flavoring agents include cocoa powder, menthol, aromatic acid, peppermint oil, borneol, and cinnamon powder. Of course, tablets and granules may further be coated appropriately with sugar coating, gelatin coating or other coatings, if necessary.

To prepare injections, these active ingredients may be supplemented, if necessary, with pH adjustors, buffers, suspending agents, solvent aids, stabilizing agents, isotonizing agents, preservatives and the like, followed by formulation in a routine manner into intravenous injections, subcutaneous injections, intramuscular injections, or intravenous drip infusions. In this case, it is also possible to prepare lyophilized formulations in a routine manner, if necessary.

Examples of suspending agents may include methylcellulose, Polysorbate 80, hydroxyethylcellulose, gum arabic, powdered tragacanth, sodium carboxymethylcellulose, and polyoxyethylenesorbitan monolaurate.

Examples of solvent aids may include polyoxyethylene hydrogenated castor oil, Polysorbate 80, nicotinamide, polyoxyethylenesorbitan monolaurate, Macrogol, and an ethyl ester of castor oil fatty acid.

Likewise, examples of stabilizing agents may include sodium sulfite, and sodium metasulfite. Examples of preservatives may include methyl parahydroxybenzoate, ethyl parahydroxybenzoate, sorbic acid, phenol, cresol, and chlorocresol.

Bevacizumab contained in the kit of the present invention may also be a formulation commercially available under the trade name Avastin®.

In the kit of the present invention, the formulation comprising a sulfonamide-including compound and the formulation comprising an angiogenesis inhibitor may be mixed together or may be included in separate containers and packaged in a single package. These formulations may be administered either simultaneously or sequentially.

The kit of the present invention can be used as a kit for angiogenesis inhibition or as a kit for cancer treatment and further comprises a packaging container, an instruction manual, an package insert and the like, in addition to the formulation comprising a sulfonamide-including compound and the formulation comprising an angiogenesis inhibitor. These packaging container, instruction manual and package insert may describe a combination for combined use of the formulations or may describe a dosage regimen for administration of separate formulations in combination or as a mixture, etc. Such a dosage regimen may be described by reference to the above description.

In another embodiment, the kit of the present invention may comprise (a) at least one selected from the group consisting of a packaging container, an instruction manual and an package insert, each of which describes the combined use of a sulfonamide-including compound and an angiogenesis inhibitor, and (b) a pharmaceutical composition comprising the sulfonamide-including compound. The kit is useful as a kit for cancer treatment or as a kit for angiogenesis inhibition. The above pharmaceutical composition comprising the sulfonamide-including compound is useful as a pharmaceutical composition for cancer treatment and as a pharmaceutical composition for angiogenesis inhibition. These packaging container, instruction manual and package insert may describe the combined use of the sulfonamide-including compound and the angiogenesis inhibitor or may describe a dosage regimen for administration of separate substances in combination or as a mixture, etc. Such a dosage regimen may be determined by reference to the above description about the pharmaceutical composition/kit.

Moreover, the present invention also includes the use of a sulfonamide-including compound for the manufacture of a pharmaceutical composition in combination with an angiogenesis inhibitor.

In the use of the present invention, the above pharmaceutical composition is useful as a pharmaceutical composition for cancer treatment and as a pharmaceutical composition for angiogenesis inhibition.

Moreover, the present invention also includes a method for preventing or treating cancer or a method for inhibiting angiogenesis, which comprises simultaneously or separately administering a sulfonamide-including compound and an angiogenesis inhibitor to a patient. In the method of the present invention for preventing or treating cancer, there is no particular limitation on the route and method of administration of the sulfonamide-including compound and the angiogenesis inhibitor. With respect to the route and method of administration, reference may be made to the above description about the pharmaceutical composition of the present invention.

The present invention will be further described by way of the following illustrative examples, which are not intended to limit the scope of the invention.

Example 1

DNA Microarray Analysis

1) Cell Culturing, Compound Treatment and RNA Extraction

With the aim of studying compound-induced changes in gene expression by DNA microarray analysis, the human colon cancer cell line HCT116 (American Type Culture Collection, Manassas, Va., U.S.A.) and the human leukemia cell line MOLT-4 (American Type Culture Collection, Manassas, Va., U.S.A.) were cultured in RPMI-1640 medium supplemented with 10% fetal bovine serum, 100 units/ml penicillin and 100 μg/ml streptomycin. Hereafter, culturing and compound treatment were carried out in an incubator adjusted to 5% $CO_2$ and 37° C. HCT116 cells and MOLT-4 cells were seeded at a density of $2.0 \times 10^6$ cells into cell culture dishes of 10 cm diameter and cultured for 24 hours, followed by compound treatment as shown below.

With respect to HCT116 cells, the following 12 compounds were evaluated: E7820 (0.8 μM), E7070 (0.8 μM), LY295501 (30 μM), CQS (8 μM), adriamycin (0.2 μM), daunomycin (0.2 μM), ICRF154 (80 μM), ICRF159 (80 μM), kenpaullone (10 μM), alsterpullone (10 μM), trichostatin A (0.1 μM) and rapamycin (80 μM). On the other hand, with respect to MOLT-4 cells, E7070 (0.8 μM) was evaluated. These compounds are all known compounds, among which adriamycin and daunomycin are known as DNA topoisomerase II inhibitors of DNA intercalation type, ICRF154 and ICRF159 are known as DNA topoisomerase II inhibitors of catalytic type, kenpaullone and alsterpullone are known as cyclin-dependent kinases (CDKs) inhibitors, trichostatin A is known as a histone deacetylase inhibitor, and rapamycin is known as a mTOR/FRAP inhibitor. The treatment concentration of each compound was set to a concentration three to five times higher than the 50% growth inhibitory concentration of each compound against HCT116 cells (based on 3-day cell growth inhibition assays using WST-8). After treatment for 24 hours at the set concentration in parentheses following the name of each compound, the cells were collected. Moreover, the cells cultured for 24 hours in the absence of these compounds were also collected.

Extraction of total RNA from the collected cells was performed using a TRIZOL reagent (Invitrogen Corporation) according to the instructions attached thereto.

2) Gene Expression Analysis by DNA Microarrays

The resulting RNA was dissolved in 100 μt of diethyl pyrocarbonate (DEPC)-treated sterilized water and further purified using an RNeasy column (QIAGEN), followed by synthesis of double-stranded cDNA using a SuperScript Choice System (Invitrogen Corporation) and a T7-d(T)$_{24}$ primer.

First, 10 μg of RNA was supplemented with 5 μM T7-d(T)$_{24}$ primer, 1× First strand buffer, 10 mM DTT, 500 μM dNTP mix and 20 units/μl SuperScript II Reverse Transcriptase, and then reacted at 42° C. for 1 hour to synthesize single-stranded DNA. Subsequently, 1× Second strand buffer, 200 μM dNTP mix, 67 U/ml DNA ligase, 270 U/ml DNA polymerase I and 13 U/ml RNase H were added and reacted at 16° C. for 2 hours to synthesize double-stranded cDNA. Further, 67 U/ml T4 DNA polymerase I was added and reacted at 16° C. for 5 minutes, followed by addition of 10 μl of 0.5 M EDTA to stop the reaction.

The resulting cDNA was purified by phenol/chloroform and labeled with biotinylated UTP and CTP using an RNA Transcript Labeling Kit (Enzo Diagnostics) according to the instructions attached thereto. The reaction product was purified on an RNeasy column and then heated in 200 mM trisacetic acid pH 8.1, 150 mM magnesium acetate, 50 mM potassium acetate at 94° C. for 35 minutes to fragment cRNA.

The fragmented cRNA was hybridized to a GeneChip (Affymetrix) Human Focus array in 100 mM MES, 1 M sodium salt, 20 mM EDTA, 0.01% Tween 20 at 45° C. for 16 hours. After hybridization, the GeneChip was washed and stained according to the protocol Midi_euk2 attached to an Affymetrix fluidics station. The staining was accomplished by using streptavidin-phycoerythrin and a biotinylated anti-streptavidin goat antibody. The stained GeneChip was scanned with an HP argon ion laser confocal microscope (Hewlett Packard) and measured for fluorescence intensity. The measurement was performed with an excitation wavelength of 488 nm and an emission wavelength of 570 nm.

Quantitative data analyses were all conducted by using GeneChip software (Affymetrix) and Gene Spring (Silicongenetics). In the case of using GeneChip software to evaluate compound-induced changes in gene expression, if there is a 2-fold or more difference in the quantified value of RNA between two groups, i.e., compound-treated and untreated groups, it is determined that the expression of a corresponding gene has significantly "increased" or "decreased." In the case of using Gene Spring to evaluate the similarity of changes in gene expression induced by each compound, hierarchical clustering analysis was performed based on changes in the expression of all genes mounted on the Human Focus Arrays.

FIG. 1 shows the results of hierarchical clustering analysis performed on HCT116 cells.

As a result of the analysis, adriamycin and daunomycin, ICRF154 and ICRF159, as well as Kenpaullone and alsterpullone, each pair of which shared the same mechanism of action, were found to cause genetic changes similar to each other (FIG. 1). It was therefore confirmed that compounds having the same mechanism of action mutually caused similar genetic changes.

E7070, E7820, LY295501 and CQS were found to cause similar genetic changes (FIG. 1). Thus, this analysis strongly suggested that E7070, E7820, LY295501 and CQS appeared to have the same or similar mechanism of action and hence produced the same or similar genetic changes and effects.

Example 2

DNA Microarray Analysis

In this example, HCT116 cells were used to study changes in gene expression induced by treatment with the following 12 compounds: E7820 (0.16 μM), E7070 (0.26 μM), LY186641 (59 μM), LY295501 (24 μM), LY573636 (9.6 μM), CQS (4.0 μM), MST16 (100 μM), etoposide (3.6 μM), ethoxzolamide (410 μM), capsaicin (280 μM), trichostatin A (0.16 μM) and kenpaullone (7.1 μM).

These compounds are all known compounds, among which MST16 is known as a DNA topoisomerase II inhibitor of catalytic type, etoposide is known as a DNA topoisomerase 11 inhibitor inducing cleavable complex formation, ethoxzolamide is known as a carbonic anhydrase inhibitor, capsaicin is known as a tumor-specific plasma membrane NADH oxidase inhibitor, trichostatin A is known as a histone deacetylase inhibitor, and kenpaullone is known as a cyclin-dependent kinases (CDKs) inhibitor.

The treatment concentration of each compound was set to a concentration twice higher than the 50% growth inhibitory concentration of each compound against HCT116 cells (based on 3-day cell growth inhibition assays using MTT). After treatment for 24 hours at the set concentration in parentheses following the name of each compound, the cells were collected. Moreover, the cells cultured for 24 hours in the absence of these compounds were also collected.

This example was performed in duplicate for each sample (for experimental convenience, individual samples were sub-numbered Control-1, Control-2, E7820-1, E7820-2, etc., such that they could be distinguished from each other). The subsequent procedures were exactly the same as shown in Example 1. Then, a GeneChip (Affymetrix) system (Human Focus array) was used to analyze changes in gene expression induced by each compound.

Figure 2:
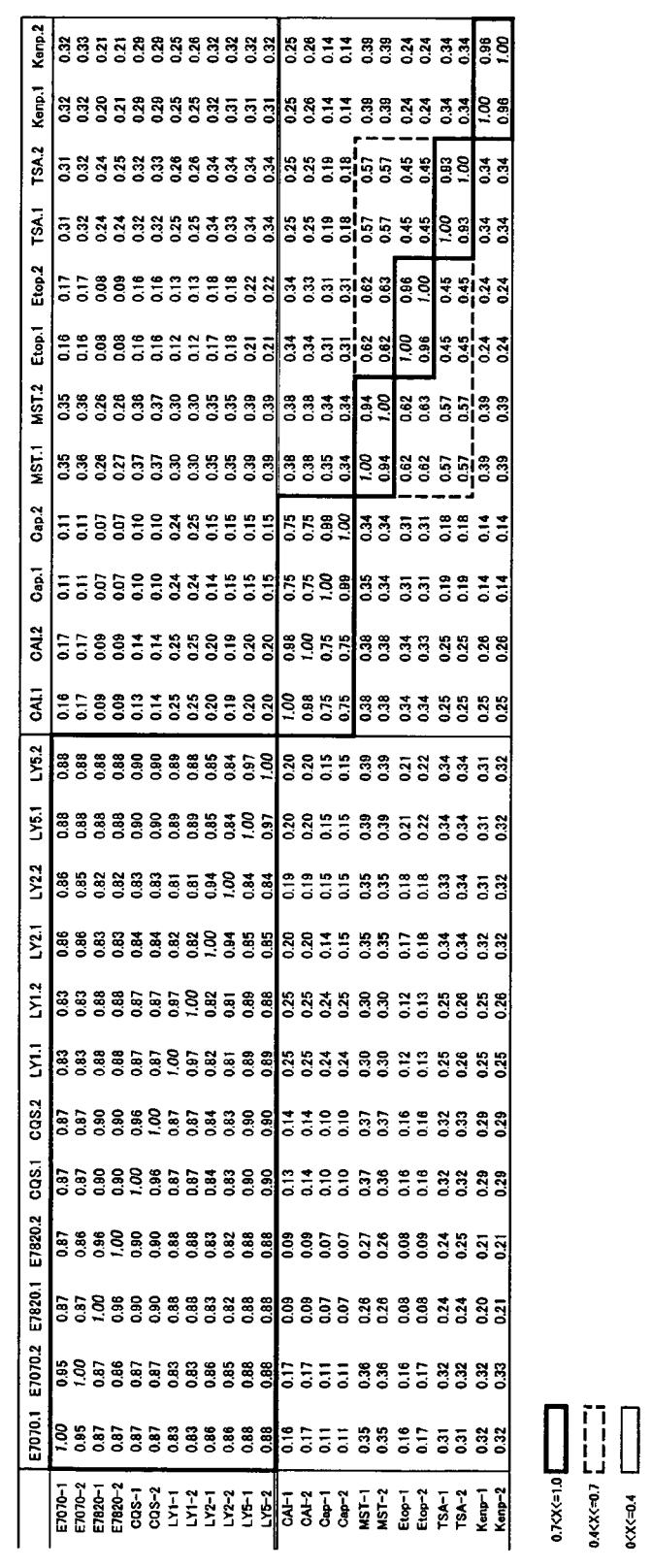
Figure 3:
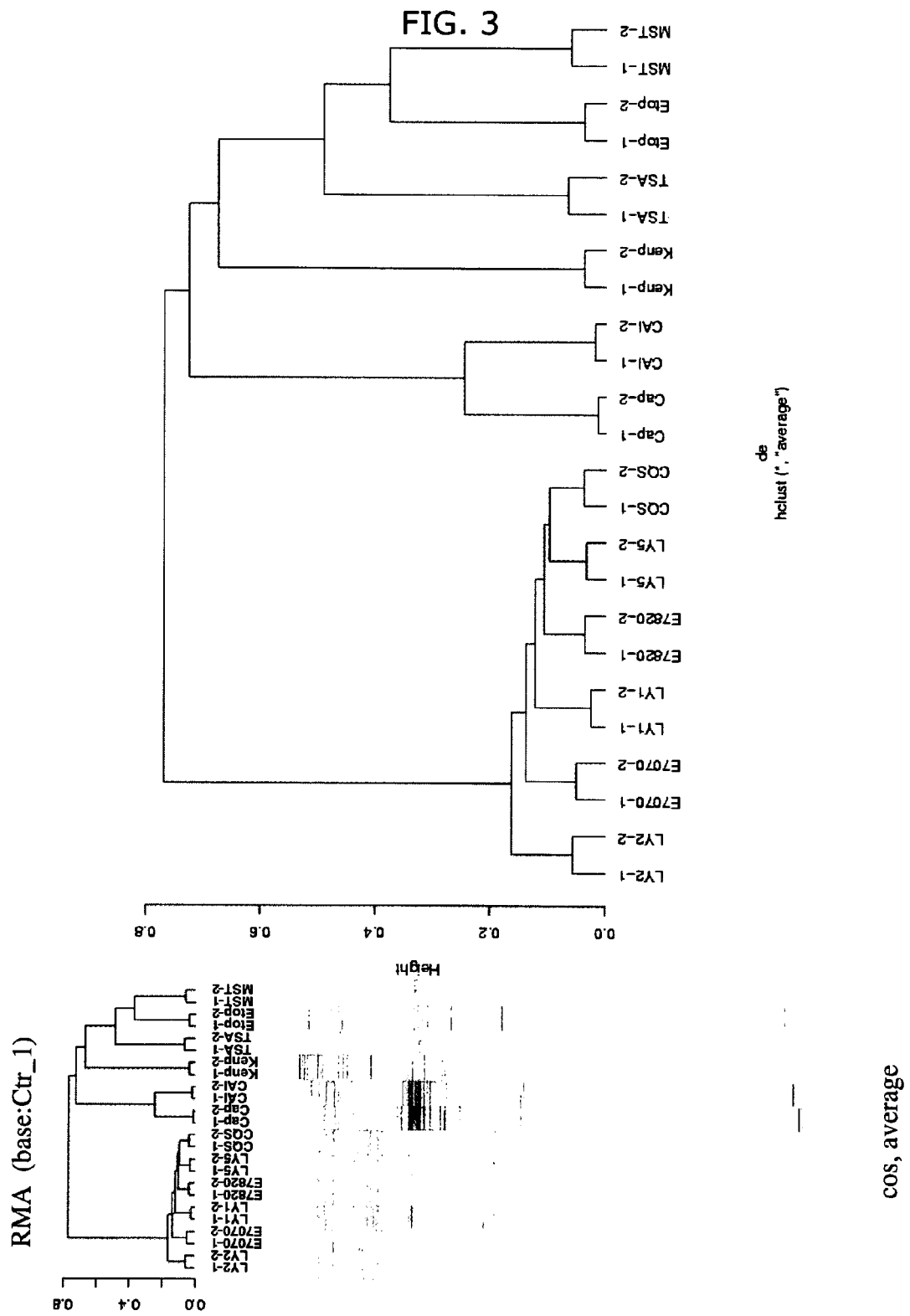
FIG. 3 shows the results of hierarchical clustering analysis in DNA microarrays in Example 2.
Figure 4:
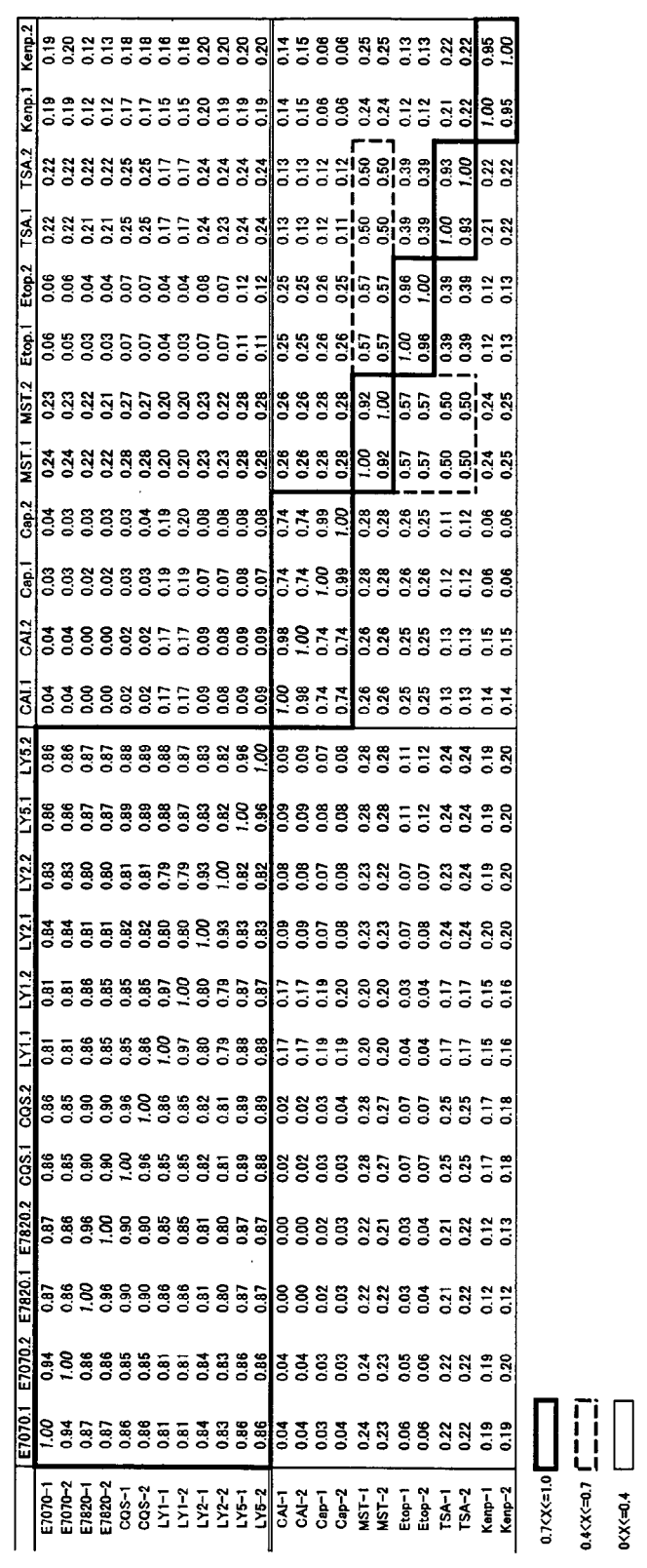
Figure 5:
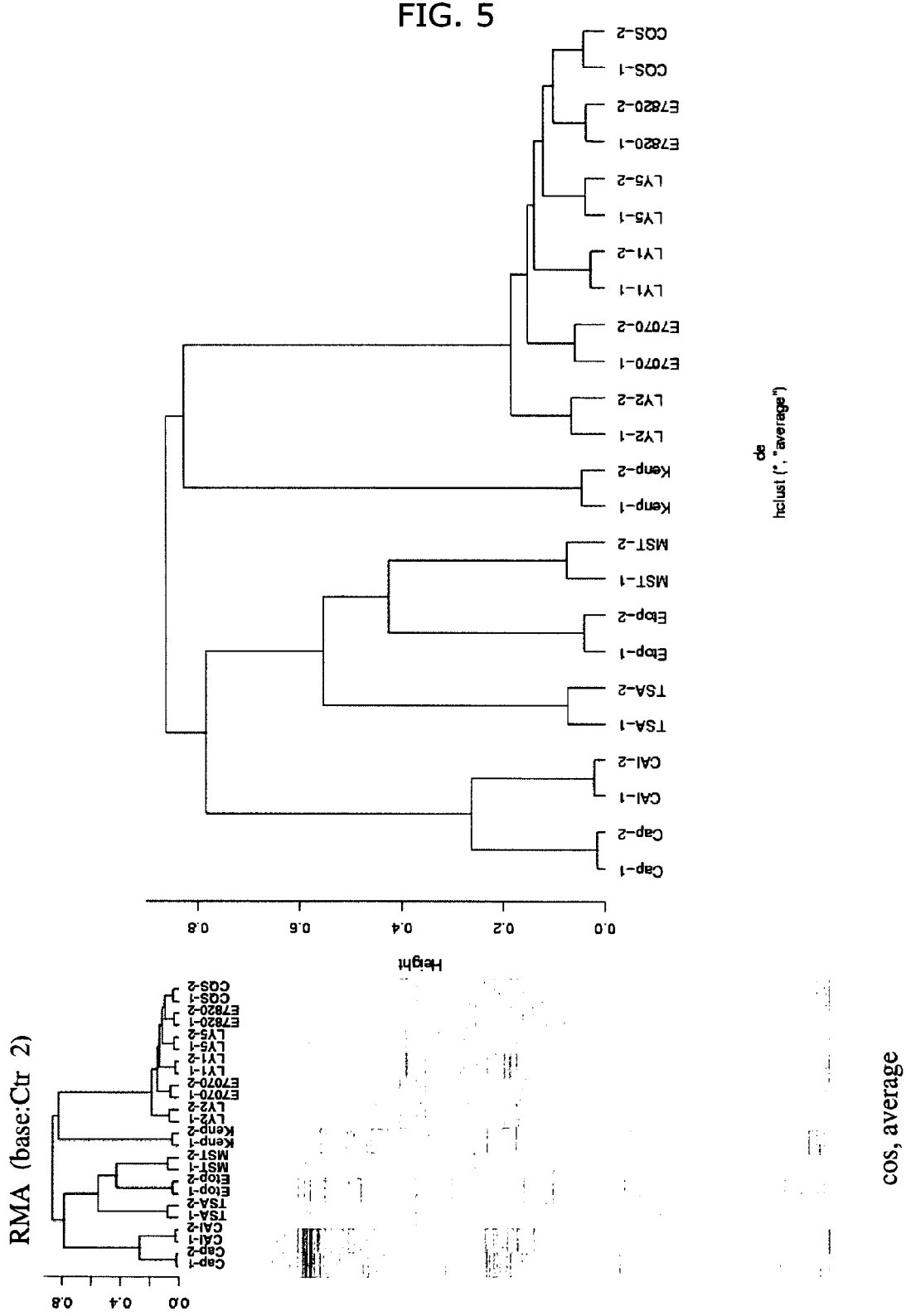
FIG. 5 shows the results of hierarchical clustering analysis in DNA microarrays in Example 2.

The 26.cel files obtained in this example for 13 samples (Control+12 compounds) in duplicate were normalized at the probe level by applying the RMA (robust multi-array average) method (Biostatistics (2003), 4, 249-264), followed by calculating the log value of signal intensity at the gene level. Subsequently, the log value of signal intensity in the untreated group (Control-1) was subtracted from the log value of signal intensity in each compound-treated group for each gene to obtain the log signal ratio of each compound-treated group to Control-1. The cosine correlation coefficient was then calculated and defined as a correlation coefficient between experiments (FIG. 2). Based on this correlation coefficient, hierarchical clustering analysis was performed by the UPGMA (Unweighted Pair Group Method with Arithmetic mean) method (FIG. 3). The same calculation was also performed on Control-2 (FIGS. 4 and 5). The software programs used were R 2.0.1 (http://www.r-project.org/) and affy package 1.5.8 (http://www.bioconductor.org).

In FIGS. 2 to 5, "LY1" denotes LY186641, "LY2" denotes LY295501, "LY5" denotes LY573636, "CAI" denotes ethoxzolamide, "Cap" denotes capsaicin, "MST" denotes MST116, "Etop" denotes etoposide, "TSA" denotes trichostatin A, and "Kenp" denotes kenpaullone. In FIGS. 3 and 5, "de hclust (*, "average")" is a command for statistical analysis and means that the average of duplicate experimental data was used for clustering analysis in R.

As a result of the analysis, E7070, E7820, LY186641, LY295501, LY573636 and CQS were found to have a very high similarity in genetic changes caused in HCT116 cells and to have different profiles than any other compounds (MST16, etoposide, ethoxzolamide, capsaicin, trichostatin A, kenpaullone) (FIGS. 2 to 5). Thus, this analysis strongly suggested that E7070, E7820, LY186641, LY295501, LY573636 and CQS appeared to have the same or similar mechanism of action and hence produced the same or similar genetic changes and effects.

Example 3

Cancer Cell Line Panel Experiment

Panels of 36 human cancer cell lines were used to study the correlation of antiproliferative activity among E7820, E7070, CQS, LY186641 and LY295501. The cancer cell lines used were the following 36 lines: DLD-1, HCT15, HCT116, HT29, SW480, SW620 and WiDr (human colon cancer cell lines), A427, A549, LX-1, NCI-H460, NCI-H522, PC-9 and PC-10 (human lung cancer cell lines), GT3TKB, HGC27, MKN1, MKN7, MKN28 and MKN74 (human stomach cancer cell lines), AsPC-1, KP-1, KP-4, MiaPaCaII, PANC-1 and SUIT-2 (human pancreas cancer cell lines), BSY-1, HBC5, MCF-7, MAD-MB-231, MDA-MB-435 and MDA-MB-468 (human breast cancer cell lines), as well as CCRF-CEM, HL60, K562 and MOLT-4 (human leukemia cell lines). All cells were cultured using RPMI-1640 medium supplemented with 10% fetal bovine serum, 100 units/ml penicillin and 100 μg/ml streptomycin under 5% $CO_2$ conditions at 37° C. (Table 4).

TABLE 4

| 36 human cancer cell lines tested in 3-day MTT assays | | |
|---|---|---|
| Colon | Stomach | Breast |
| DLD-1 (1250/well, 16.8 h) | GT3TKB (2000/well, 21.1 h) | BSY-1 (2000/well, 46.1 h) |
| HCT15 (1500/well, 14.5 h) | HGC27 (1500/well, 14.6 h) | HBC5 (2000/well, 31.8 h) |
| HCT116 (1250/well, 13.4 h) | MKN1 (4000/well, 35.9 h) | MCF-7 (3000/well, 29.5 h) |
| HT29 (2500/well, 19.8 h) | MKN7 (3000/well, 37.4 h) | MDA-MB231 (2000/well, 21.6 h) |
| SW480 (3000/well, 19.5 h) | MKN28 (2000/well, 22.7 h) | MDA-MB-435 (3000/well, 24.4 h) |
| SW620 (2500/well, 17.3 h) | MKN74 (4000/well, 24.8 h) | MDA-MB-468 (3000/well, 34.2 h) |
| WiDr (2000/well, 18.9 h) | | |
| Lung | Pancreas | Leukemia |
| A427 (2500/well, 32.4 h) | AsPC-1 (2500/well, 28.4 h) | CCRF-CEM (1500/well, 27.2 h) |
| A549 (1250/well, 18.9 h) | KP-1 (2000/well, 24.8 h) | HL60 (1500/well, 29.5 h) |
| LX-1 (2000/well, 17.2 h) | KP-4 (2000/well, 16.7 h) | K562 (1500/well, 20.6 h) |
| NCI-H460 (1000/well, 13.6 h) | MiaPaCaII (2500/well, 19.1 h) | MOLT-4 (1500/well, 22.3 h) |
| NCI-H522 (4000/well, 80.4 h) | PANC-1 (2500/well, 27.9 h) | |
| PC-9 (2000/well, 23.7 h) | SUIT-2 (2000/well, 15.6 h) | |
| PC-10 (2000/well, 24.0 h) | | |

Cell Line (Initial Cell Number, Doubling Time)

Table 4 shows the type, initial cell number and doubling time of human cancer cell lines in human cancer cell line panels.

Cells of these cell lines were seeded in 96-well microplates (flat-bottomed) (50 μl/well) at the cell numbers indicated in Table 4. After 24 hours, a 3-fold dilution series of each compound was added (50 μl/well). After 72 hours, WST-8 (10 μl/well) was further added and the absorbance at 450 nm was measured. The least squares method was used to determine the 50% growth inhibitory concentration of each compound against all 36 cancer cell lines, followed by comparing the pattern of growth inhibition between compounds. As indexes of correlation, Pearson's correlation coefficients were used (Paull, K. D. et al. Display and analysis of patterns of differential activity of drugs against human tumor cell lines: development of mean graph and COMPARE algorithm. J. Natl. Cancer Inst. 1989, 81, 1088-1092; Monks, A. et al. Feasibility of a high-flux anti-cancer drug screen using a diverse panel of cultured human tumor cell lines. J. Natl. Cancer Inst. 1991, 83, 757-766).

As a result, E7070, E7820, LY186641, LY295501 and CQS were found to show high correlation coefficients in antiproliferative activity against each cancer cell line (Table 5). Thus, this analysis strongly suggested that E7070, E7820, LY186641, LY295501 and CQS appeared to have the same or similar mechanism of action and hence produced the same or similar genetic changes and effects.

TABLE 5

|  | E7070 | E7820 | CQS | LY186641 | LY295501 |
|---|---|---|---|---|---|
| E7070 | 1.00 | 0.98 | 0.97 | 0.93 | 0.80 |
| E7820 | 0.98 | 1.00 | 0.96 | 0.95 | 0.82 |
| CQS | 0.97 | 0.96 | 1.00 | 0.92 | 0.82 |
| LY186641 | 0.93 | 0.95 | 0.92 | 1.00 | 0.81 |
| LY295501 | 0.80 | 0.82 | 0.82 | 0.81 | 1.00 |

Table 5 shows correlation coefficients between compounds (E7070, E7820, CQS, LY186641 and LY295501) in human cancer cell line panels.

Example 4

Cross Resistance in E7070-Resistant Sub-Clonal Cell Lines

E7070-resistant sub-clonal cell lines were used to evaluate the antiproliferative activity of E7820, LY186641, LY295501, LY-ASAP and CQS. HCT116-C9 was a sub-clone separated from the human colon cancer cell line HCT116 (American Type Culture Collection, Manassas, Va., U.S.A.), while HCT116-C9-C1 and HCT116-C9-C4 were E7070-resistant sub-clonal cell lines obtained by culturing this HCT116-C9 in the presence of gradually increasing concentrations of E7070 (Molecular Cancer Therapeutics, 2002, 1, 275-286).

These 3 cell lines HCT116-C9, HCT116-C9-C1 and HCT116-C9-C4 were each seeded at 3000 cells/well in 96-well microplates (flat-bottomed) (50 μl/well). After 24 hours, a 3-fold dilution series of each compound was added (50 μl/well). After 72 hours, the cell growth inhibitory activity was evaluated by the MTT method (Mossmann T., J. Immunol. Methods, 1983, 65, 55-63). The least squares method was used to determine the 50% growth inhibitory concentration of each compound against each cancer cell line.

Figure 6:
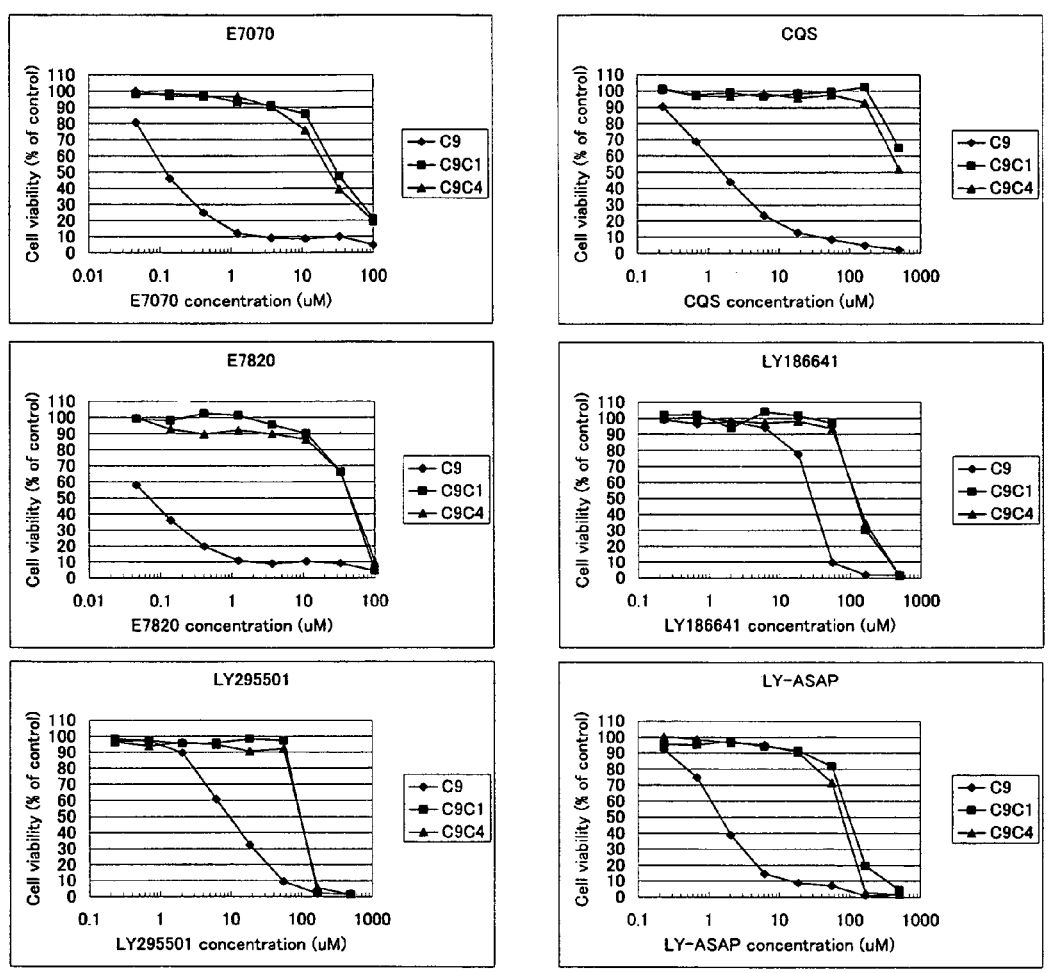
FIG. 6 shows the antiproliferative effect of E7070, E7820, CQS, LY186641, LY295501 and LY-ASAP on HCT116-C9, HCT116-C9-C1 and HCT116-C9-C4, as measured by cell growth inhibition assay.

As a result, the antiproliferative activity of E7070 against HCT116-C9 (C9) was IC50=0.127 μM, whereas the activity against HCT116-C9-C1 (C9C1) and HCT116-C9-C4 (C9C4) was IC50=31.9 μM and 26.9 μM, respectively. It was therefore confirmed that the antiproliferative activity of E7070 against C9C1 and C9C4 was greatly reduced (FIG. 6). Likewise, the antiproliferative activity of E7820, CQS, LY186641, LY295501 and LY-ASAP against HCT116-C9 was IC50=0.080 μM, 1.73 μM, 33.6 μM, 10.9 μM and 1.63 μM, respectively, whereas the activity against HCT116-C9-C1 and HCT116-C9-C4 was as follows: IC50=51.2 μM, 634 μM, 134 μM, 111 μM and 113 μM, respectively, for HCT116-C9-C1 and IC50=52.8 μM, 517 μM, 138 μM, 110 μM and 90.3 μM, respectively, for HCT116-C9-C4. Thus, with respect to the antiproliferative activity of E7820, CQS, LY186641, LY295501 and LY-ASAP, a greater reduction in the activity was observed in C9C1 and C9C4 than in C9 (FIG. 6). Thus, this strongly suggested that E7070, E7820, LY186641, LY295501, LY-ASAP and CQS appeared to have the same or similar mechanism of action and hence produced the same or similar genetic changes and effects.

Example 5

Cross Resistance in E7070-Resistant Sub-Clonal Cell Lines

Exactly the same procedure as used in Example 4 was repeated to evaluate the antiproliferative activity of both LY573636 and E7070 using E7070-resistant sub-clonal cell lines.

Figure 7:
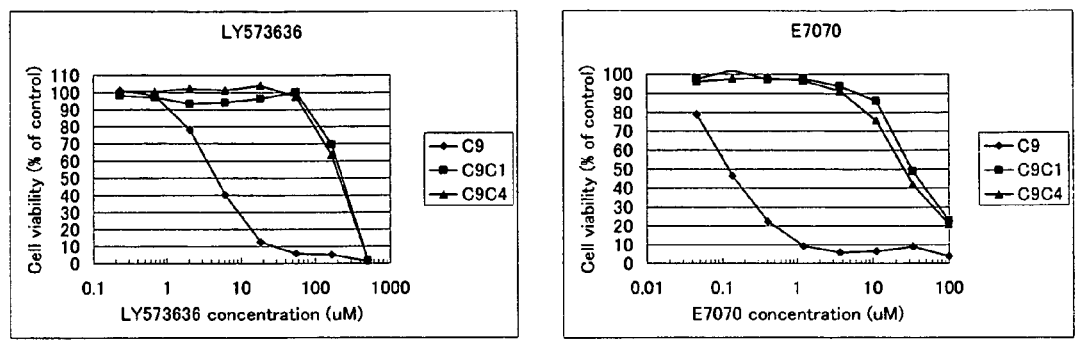
FIG. 7 shows the antiproliferative effect of E7070 and LY573636 on HCT116-C9, HCT116-C9-C1 and HCT116-C9-C4, as measured by cell growth inhibition assay.

As a result, it was confirmed again that the antiproliferative activity of E7070 was more greatly reduced in HCT116-C9-C1 and HCT116-C9-C4 (IC50=32.7 μM and 28.0 μM, respectively) than in HCT116-C9 (IC50=0.127 μM) (FIG. 7). Likewise, with respect to the antiproliferative activity of LY573636, a greater reduction in the activity was observed in HCT116-C9-C1 and HCT116-C9-C4 (IC50=264 μM and 240 μM, respectively) than in HCT116-C9 (IC50=5.11 μM) (FIG. 7). Thus, this strongly suggested that LY573636 appeared to have the same or similar mechanism of action as E7070 and hence produced the same or similar genetic changes and effects.

These results (Examples 1 to 5) indicated that E7070, E7820, LY186641, LY295501, LY-ASAP, LY573636 or CQS or combinations thereof produced the same or similar genetic changes as well as the same or similar actions and effects.

Moreover, E7820 has been found to show excellent angiogenesis inhibitory activity and anti-tumor activity when used in combination with an angiogenesis inhibitory agent (see WO03/074045).

It was therefore indicated that a sulfonamide-including compound, preferably E7070, LY186641, LY295501, LY-ASAP, LY573636 or CQS or combinations thereof, showed excellent angiogenesis inhibitory activity and anti-tumor activity when used in combination with an angiogenesis inhibitor.

Example 6

Combined Effect of E7820 and Bevacizumab on VEGF-Induced Cell Proliferation in Vascular Endothelial Cell Proliferation Assay (in vitro)

Human umbilical vein endothelial cells were suspended in 2% FBS-containing Human endothelial-SFM Basal Growth Medium (Invitrogen Corporation) and adjusted to $1 \times 10^4$ cells/ml. The resulting cell suspension was dispensed in 100 μl aliquots into each well of 96-well plates and cultured at 37° C. in a 5% carbon dioxide incubator. On the next day, a solution containing E7820, a solution containing bevacizumab (Avastin®, purchased from Genentech), and a solution containing both E7820 and bevacizumab were respectively diluted with Human endothelial-SFM Basal Growth Medium containing 20 ng/ml VEGF (Genzyme Techne Corp.) and 2% FBS. The resulting diluted solutions were then added to the individual wells of the plates in a volume of 100 μl/well, followed by further culturing.

After 3 days, 10 μl of Cell Counting Kit-8 solution (Cell Counting Kit-8, Wako Pure Chemical Industries, Ltd., Japan) was added and cultured at 37° C. for 2 to 3 hours, followed by measuring the absorbance at 450 nm with a plate reader (Corona Electric Co., Ltd., Japan). The combined effect was calculated according to the equation of Chou et al. (Adv. Enzyme Regul., 22, 27-55, 1984).

As a result, the combination of E7820 and bevacizumab was found to show a stronger antiproliferative effect than when E7820 or bevacizumab was used alone (Table 6).

TABLE 6

| Compound concentration | % of control | | |
|---|---|---|---|
| (μg/μl) | E7820 | Bevacizumab | E7820 + Bevacizumab[1] |
| 0.0000 | 100.0 | 100.0 | 100.0 |
| 0.0006 | 98.9 | 96.0 | 97.4 |
| 0.0012 | 102.2 | 94.2 | 87.4 |
| 0.0024 | 104.8 | 89.5 | 92.3 |
| 0.0049 | 99.4 | 88.3 | 92.0 |
| 0.0098 | 97.2 | 80.8 | 82.8 |
| 0.0195 | 88.9 | 78.8 | 77.5 |
| 0.0391 | 87.9 | 71.0 | 57.4 |
| 0.0781 | 72.3 | 68.5 | 46.0 |
| 0.1563 | 60.5 | 64.2 | 38.0 |
| 0.3125 | 56.2 | 62.0 | 34.8 |
| 0.6250 | 57.2 | 60.1 | 30.5 |
| 1.2500 | 47.8 | 56.1 | 25.9 |
| 2.5000 | 41.4 | 51.8 | 23.8 |
| 5.0000 | 37.4 | 54.8 | 20.9 |
| 10.0000 | 34.4 | 53.2 | 18.7 |
| 20.0000 | 33.1 | 50.4 | 22.3 |
| 40.0000 | 12.5 | 51.7 | 12.1 |

[1]"E7820 + Bevacizumab" shows the results of E7820 and bevacizumab combined at the concentrations indicated in the left column.

Table 6 shows the percentage of absorbance measured in Example 6 for the cells treated with each compound relative to the untreated cells.

In view of the fact that the combination index (CI) for the combined use of E7820 and bevacizumab was 1 or less, it was indicated that E7820 showed a synergistic effect on cell proliferation when used in combination with bevacizumab (Table 7). Likewise, CI was 0.07 or less within a wide range of Fractional inhibition (fa) between 0.05 and 0.95, indicating that E7820 and bevacizumab produced a synergistic effect independently of their concentration (Table 7). This effect was significantly higher than that usually observed by combined use and was completely unexpected to those skilled in the art.

TABLE 7

| Fractional inhibition (fa) | Combination index (CI) | Combined effect |
| --- | --- | --- |
| 0.05 | 0.07 | Synergistic |
| 0.1 | 0.06 | Synergistic |
| 0.2 | 0.05 | Synergistic |
| 0.3 | 0.05 | Synergistic |
| 0.4 | 0.04 | Synergistic |
| 0.5 | 0.04 | Synergistic |
| 0.6 | 0.04 | Synergistic |
| 0.7 | 0.04 | Synergistic |
| 0.8 | 0.04 | Synergistic |
| 0.9 | 0.03 | Synergistic |
| 0.95 | 0.03 | Synergistic |

Table 7 shows the synergistic effect of E7820 and bevacizumab on VEGF-induced cell proliferation in the vascular endothelial cell proliferation assay (in vitro).

In view of the foregoing, a combination of E7820 and bevacizumab provides pharmaceutical compositions and kits showing excellent angiogenesis inhibitory activity; the pharmaceutical compositions and kits of the present invention can be used for cancer prevention and treatment as well as for angiogenesis inhibition.

Example 7

Combined Use of E7820 and Bevacizumab in Subcutaneous Transplantation Model (in vivo) of the Human Colon Cancer Cell Line Colo320DM Human colon cancer cell line Colo320DM (purchased from Dainippon Pharmaceutical Co., Ltd., Japan) was cultured at 37° C. in RPMI1640 (containing 10% FBS) to about 80% confluency in a 5% carbon dioxide incubator, and the cells were collected by trypsin-EDTA. The cells were diluted with 50% Matrigel-containing phosphate buffer to prepare a $5 \times 10^7$ cells/mL suspension, and the resulting cell suspension was subcutaneously transplanted in 0.1 mL volumes to nude mice at the side of their body. Starting from 7 days after the transplantation, E7820 (200 mg/kg, given twice a day for 3 weeks by the oral route) and bevacizumab (25 mg/kg, given twice a week for 3 weeks by the intravenous route) were administered. Tumor long and short axes were measured with a digimatic caliper (Mitsutoyo) and used to calculate both tumor volume and relative tumor volume according to the following equations.

Tumor volume TV=tumor long axis(mm)×tumor short axis$^2$(mm$^2$)/2

Relative tumor volume RTV=tumor volume at the day of measurement/tumor volume at the first day of administration If the co-treated group shows a statistically significant interaction as analyzed by two-way ANOVA, E7820 and bevacizumab are determined to have a synergistic effect on each other.

Figure 8:
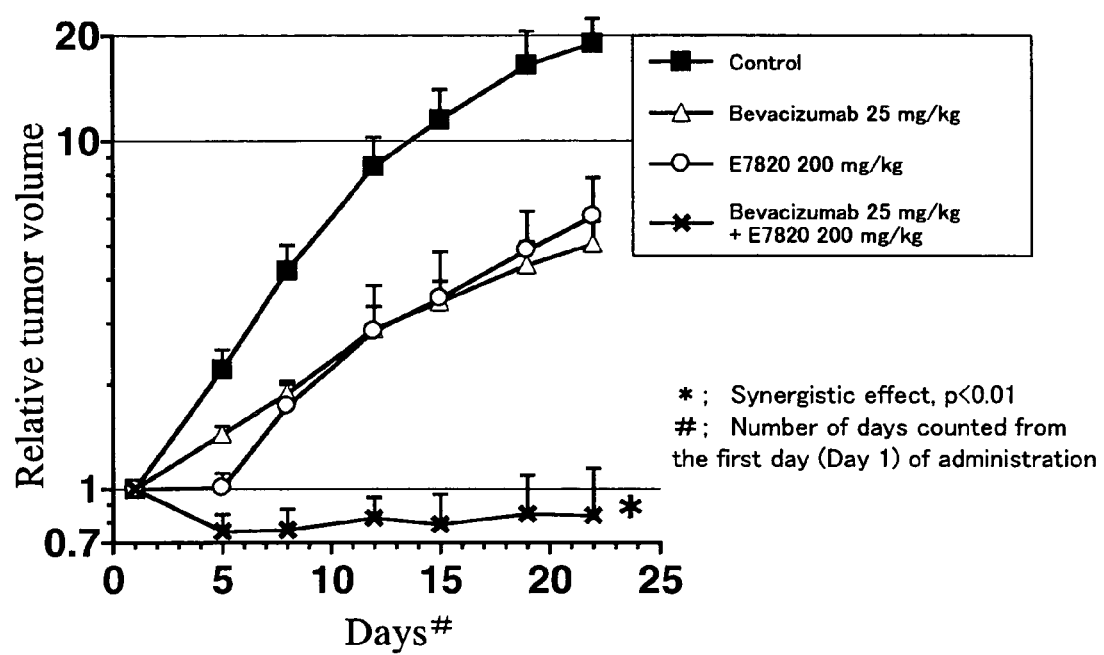
FIG. 8 shows the combined effect of E7820 and bevacizumab on tumor growth in a subcutaneous transplantation model (in vivo) of the human colon cancer cell line Colo320DM.

As a result, E7820 was found to produce a synergistic effect when used in combination with bevacizumab, and their combined use showed an excellent anti-tumor effect when compared to the effect of E7820 or bevacizumab alone (Table 8 and FIG. 8). Moreover, the combined use of E7820 and bevacizumab was found to produce an excellent anti-tumor effect that could not be produced by bevacizumab alone (Table 8 and FIG. 8).

TABLE 8

| Analyte administered | Relative tumor volume at Day 22 Mean ± SD | Two-way ANOVA |
| --- | --- | --- |
| Control (untreated) | 19.0 ± 3.4 | |
| E7820 200 mg/kg | 6.1 ± 1.8 | |
| Bevacizumab 25 mg/kg | 5.1 ± 0.8 | |
| E7820 200 mg/kg + Bevacizumab 25 mg/kg | 0.8 ± 0.3 | $p < 0.01$ Synergistic effect |

Table 8 shows the anti-tumor effect produced by either one or a combination of E7820 and bevacizumab in the nude mouse subcutaneous transplantation model of Colo320DM. The first day of administration was defined as Day 1.

In view of the foregoing, a combination of E7820 and bevacizumab provides pharmaceutical compositions and kits showing excellent anti-tumor activity; the pharmaceutical compositions and kits of the present invention can be used for cancer treatment.

Example 8

Combined Use of E7070 and Bevacizumab in Subcutaneous Transplantation Model of the Human Colon Cancer Cell Line Colo320DM Human colon cancer cell line Colo320DM (purchased from ATCC) was cultured in RPMI1640 (containing 10% FBS) to about 80% confluency in a 5% carbon dioxide incubator, and the cells were collected by trypsin-EDTA. The cells were diluted with Hanks balanced solution to prepare a $5 \times 10^7$ cells/ml suspension, and the resulting cell suspension was subcutaneously transplanted in 0.1 mL volumes to nude mice at the side of their body.

After the transplantation, from the time point when the mean tumor volume reached 259 mm$^3$, E7070 (40 mg/kg/day) and bevacizumab (25 mg/kg/day) were administered alone or in combination.

E7070 alone was administered once a day for 5 days (Day 1 to Day 5) by the intravenous route. Bevacizumab alone was administered twice a week for 2 weeks (Days 1, 5, 8 and 12) by the intravenous route.

The co-treated group was administered with E7070 at Day 1 to Day 5 by the intravenous route and with bevacizumab at Days 1, 5, 8 and 12 by the intravenous route.

After starting the administration, tumor long and short axes were measured at a frequency of twice a week with a digimatic caliper (Mitsutoyo) and used to calculate the tumor volume according to the following equation.

Tumor volume TV=tumor long axis(mm)×tumor short axis$^2$(mm$^2$)/2

For determination of the anti-tumor effect, the values of the following two parameters were used.

$T_{x4}$: Time (days) required for a tumor to grow 4-fold of the initial tumor volume RTV: Relative tumor volume (RTV) at Day 23*

* RTV=tumor volume at Day 23/initial tumor volume at Day 1

If the co-treated group produces a higher anti-tumor effect than the groups treated with either drug alone and shows a statistically significant interaction ($P<0.05$) as analyzed by two-way ANOVA, E7070 and bevacizumab are determined to have a synergistic effect on each other. Likewise, if the co-treated group produces a higher anti-tumor effect than the groups treated with either drug alone and has a significance level of 0.05<P<0.10, E7070 and bevacizumab are determined to have a synergistic tendency.

Figure 9:
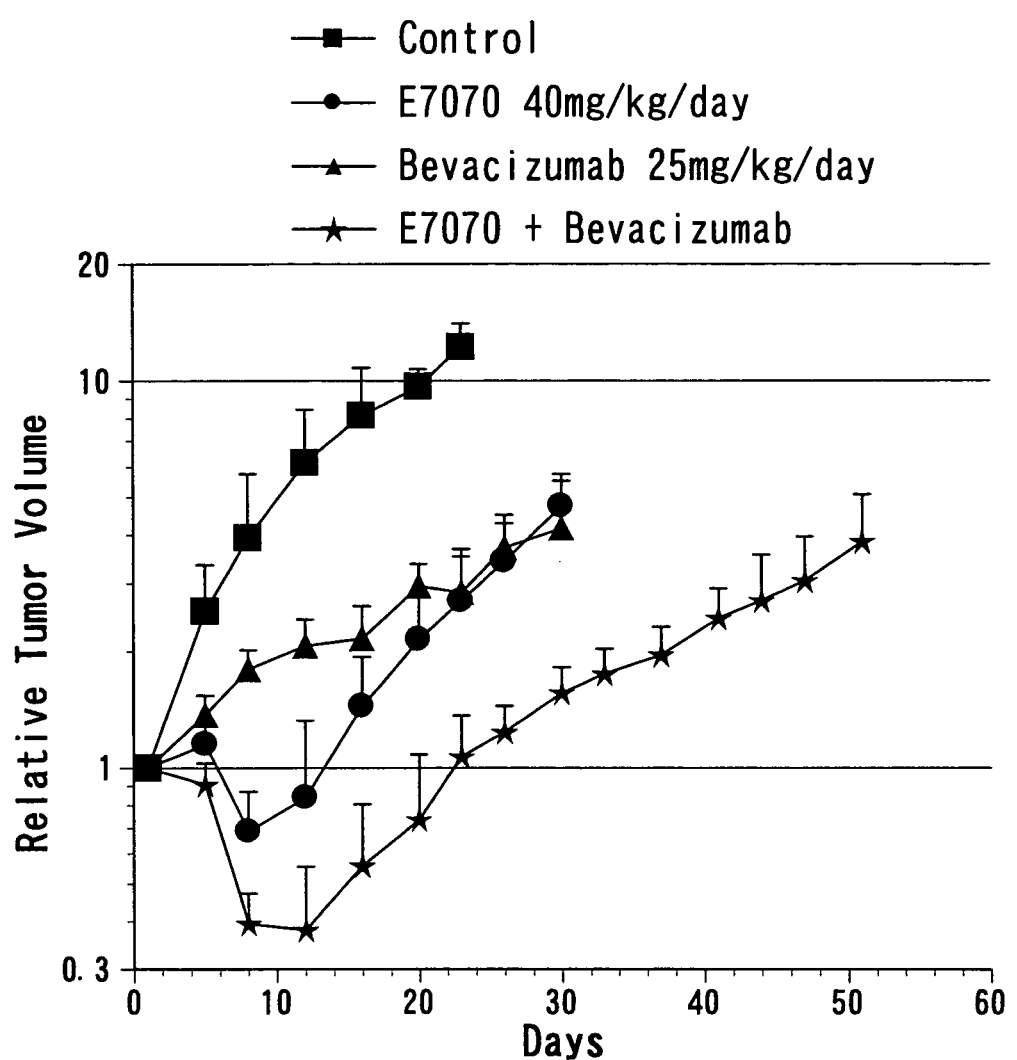
FIG. 9 shows the combined effect of E7070 and bevacizumab on tumor growth in a subcutaneous transplantation model (in vivo) of the human colon cancer cell line Colo320DM.

As a result, the combined use of E7070 and bevacizumab was found to produce an excellent anti-tumor effect when compared to the effect of E7070 or bevacizumab alone (Table 9 and FIG. 9). Moreover, the combined use of E7070 and bevacizumab was found to produce an excellent effect that could not be produced by bevacizumab alone (Table 9 and FIG. 9).

TABLE 9

| Analyte administered | $T_{x4}$ | | Relative tumor volume (RTV) | |
|---|---|---|---|---|
| | Mean ± SD (days) | Two way ANOVA | Mean ± SD | Two way ANOVA |
| Control (untreated) | 9.3 ± 1.3 | | 12.23 ± 1.80 | |
| E7070 40 mg/kg | 27.0 ± 3.4 | | 2.70 ± 0.97 | |
| Bevacizumab 25 mg/kg | 26.3 ± 2.8 | | 2.84 ± 0.68 | |
| E7070 40 mg/kg Bevacizumab 25 mg/kg (co-treated) | 52.4 ± 6.8 | P = 0.057 Synergistic tendency | 1.07 ± 0.29 | P = 0.060 Synergistic tendency |

Table 9 shows the anti-tumor effect produced by either one or a combination of E7070 and bevacizumab in the transplantation model (in vivo) of the colon cancer cell line Colo320DM. The first day of administration was defined as Day 1.

In view of the foregoing, a combination of E7070 and bevacizumab provides pharmaceutical compositions and kits showing excellent anti-tumor activity; the pharmaceutical compositions and kits of the present invention can be used for cancer treatment.

Example 9

Combined Use of E7820 and 4-(3-Chloro-4-(Cyclopropylaminocarbonyl)-Aminophenoxy)-7-Methoxy-6-Quinolinecarboxamide in Subcutaneous Transplantation Model (in Vivo) of Human Renal Cancer Cell Line 786-O Human renal cancer cell line 786-O (purchased from ATCC) was cultured in RPMI1640 (containing 10% FBS) to about 80% confluency in a 5% carbon dioxide incubator, and the cells were collected by trypsin-EDTA. The cells were diluted with 50% Matrigel-containing phosphate buffer to prepare a $1 \times 10^8$ cells/mL suspension, and the resulting cell suspension was subcutaneously transplanted in 0.1 mL volumes to nude mice at the side of their body. Starting from 7 days after the transplantation, E7820 (100 mg/kg, given twice a day for 2 weeks) and 4-(3-chloro-4-(cyclopropylaminocarbonyl)aminophenoxy)-7-methoxy-6-quinolinecarboxamide (100 mg/kg, given once a day for 2 weeks) were administered alone or in combination by the oral route. Tumor long and short axes were measured with a digimatic caliper (Mitsutoyo) and used to calculate both tumor volume and relative tumor volume according to the following equations.

Tumor volume TV=tumor long axis(mm)×tumor short axis$^2$(mm$^2$)/2

Relative tumor volume RTV=tumor volume at the day of measurement/tumor volume at the first day of administration If the co-treated group shows a statistically significant interaction as analyzed by two-way ANOVA, E7820 and 4-(3-chloro-4-(cyclopropylaminocarbonyl)aminophenoxy)-7-methoxy-6-quinolinecarboxamide are determined to have a synergistic effect on each other.

Figure 10:
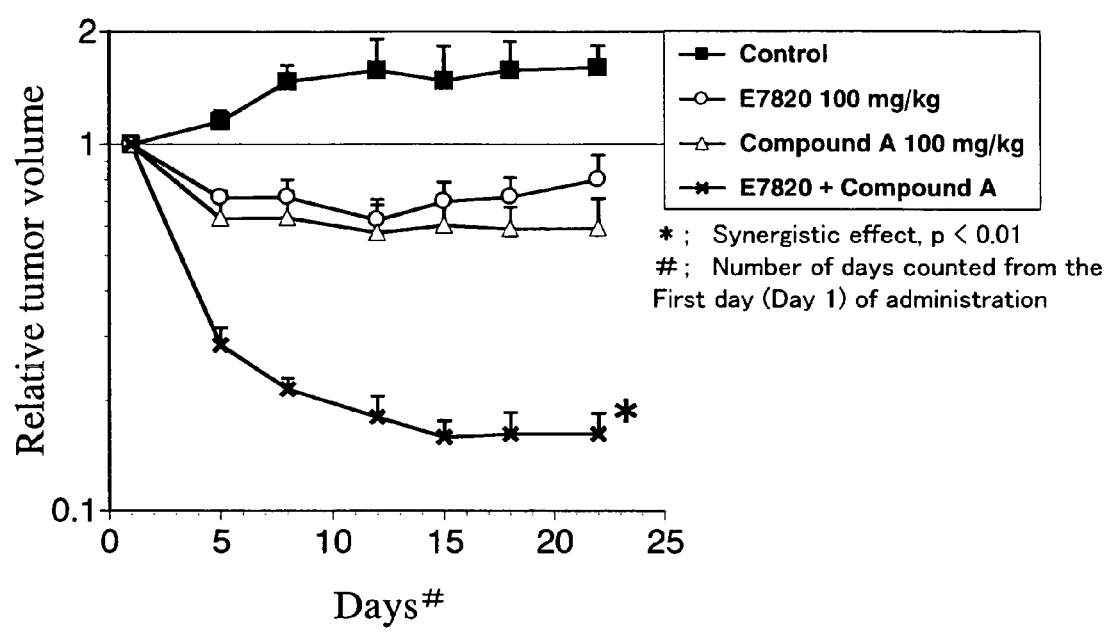
FIG. 10 shows the combined effect of E7820 and 4-(3-chloro-4-(cyclopropylaminocarbonyl)aminophenoxy)-7-methoxy-6-quinolinecarboxamide on tumor growth in a subcutaneous transplantation model (in vivo) of human renal cancer cell line 786-O.

As a result, E7820 was found to produce a synergistic effect when used in combination with 4-(3-chloro-4-(cyclopropylaminocarbonyl)aminophenoxy)-7-methoxy-6-quinolinecarboxamide, and their combined use showed an excellent anti-tumor effect when compared to the effect of E7820 or 4-(3-chloro-4-(cyclopropylaminocarbonyl)aminophenoxy)-7-methoxy-6-quinolinecarboxamide alone (Table 10 and FIG. 10).

TABLE 10

| Analyte administered | Relative tumor volume at Day 22 Mean ± SD | Two-way ANOVA |
|---|---|---|
| Control (untreated) | 1.61 ± 0.23 | |
| E7820 100 mg/kg | 0.80 ± 0.13 | |
| Compound A 100 mg/kg | 0.59 ± 0.12 | |
| E7820 100 mg/kg + Compound A 100 mg/kg | 0.16 ± 0.02 | p < 0.01 Synergistic effect |

Table 10 shows the anti-tumor effect produced by either one or a combination of E7820 and 4-(3-chloro-4-(cyclopropylaminocarbonyl)aminophenoxy)-7-methoxy-6-quinolinecarboxamide (in Table 10 and FIG. 10, Compound A denotes 4-(3-chloro-4-(cyclopropylaminocarbonyl)-aminophenoxy)-7-methoxy-6-quinolinecarboxamide) in the transplantation model (in vivo) of renal cancer cell line 786-O. The first day of administration was defined as Day 1.

In view of the foregoing, a combination of E7820 and 4-(3-chloro-4-(cyclopropylaminocarbonyl)aminophenoxy)-7-methoxy-6-quinolinecarboxamide provides pharmaceutical compositions and kits showing excellent anti-tumor activity; the pharmaceutical compositions and kits of the present invention can be used for cancer treatment.

INDUSTRIAL APPLICABILITY

The present invention provides pharmaceutical compositions and kits showing excellent angiogenesis inhibitory activity and/or anti-tumor activity.

More specifically, as a result of combining sulfonamide-including compounds, preferably E7070, LY186641, LY295501, LY-ASAP, LY573636 or CQS or combinations thereof, with angiogenesis inhibitors, the present invention provides pharmaceutical compositions and kits showing excellent angiogenesis inhibitory activity and/or anti-tumor activity. The pharmaceutical compositions and kits of the present invention are useful for cancer treatment or angiogenesis inhibition. Likewise, when combining sulfonamide-including compounds, preferably E7820, with VEGF receptor kinase inhibitors, the present invention provides pharmaceutical compositions and kits showing excellent angiogenesis inhibitory activity and/or anti-tumor activity. The pharmaceutical compositions and kits of the present invention are useful for cancer treatment or angiogenesis inhibition.

All of the above-mentioned patents, applications, test methods, and publications are hereby incorporated by reference in their entirety.

The invention claimed is:

1. A pharmaceutical composition comprising a sulfonamide-including compound in combination with a VEGF receptor kinase inhibitor,
wherein the sulfonamide-including compound is N-(3-cyano-4-methyl-1H-indol-7-yl)-3-cyanobenzenesulfonamide
or a pharmacologically acceptable salt thereof or a solvate thereof, and
wherein the VEGF receptor kinase inhibitor is 4-(3-chloro-4-(cyclopropyl-aminocarbonyl)aminophenoxy)-7-methoxy-6-quinolinecarboxamide, or a pharmacologically acceptable salt thereof or a solvate thereof.

2. The pharmaceutical composition according to claim 1, wherein the VEGF receptor kinase inhibitor is a methanesulfonate salt of 4-(3-chloro-4-(cyclopropylamino-carbonyl)aminophenoxy)-7-methoxy-6-quinolinecarboxamide.

3. The pharmaceutical composition according to any one of claims 1 and 2, which is a pharmaceutical composition for cancer treatment.

4. The pharmaceutical composition according to any one of claims 1 and 2, which is a pharmaceutical composition for angiogenesis inhibition.

5. A method for treating cancer and/or a method for inhibiting angiogenesis, which comprises administering a sulfonamide-including compound and a VEGF receptor kinase inhibitor to a patient,
wherein the sulfonamide-including compound is N-(3-cyano-4-methyl-1H-indol-7-yl)-3-cyanobenzenesulfonamide, or a pharmacologically acceptable salt thereof or a solvate thereof, and
wherein the VEGF receptor kinase inhibitor is 4-(3-chloro-4-(cyclopropylaminocarbonyl)aminophenoxy)-7-methoxy-6-quinolinecarboxamide, or a pharmacologically acceptable salt thereof or a solvate thereof.

6. The method according to claim 5, wherein the VEGF receptor kinase inhibitor is a methanesulfonate salt of 4-(3-chloro-4-(cyclopropylaminocarbonyl)aminophenoxy)-7-methoxy-6-quinolinecarboxamide.

* * * * *